United States Patent [19]
Elrod et al.

[11] Patent Number: 6,100,057
[45] Date of Patent: Aug. 8, 2000

[54] METHOD FOR INCREASING HEMOPROTEIN PRODUCTION IN FILAMENTOUS FUNGI

[75] Inventors: Susan L. Elrod; Joel R. Cherry, both of Davis; Aubrey Jones, Woodland, all of Calif.

[73] Assignee: Novo Nordisk Biotech, Inc., Davis, Calif.

[21] Appl. No.: 08/871,267

[22] Filed: Jun. 9, 1997

Related U.S. Application Data

[63] Continuation-in-part of application No. 08/662,752, Jun. 10, 1996, abandoned.
[60] Provisional application No. 60/041,158, Mar. 17, 1997.

[51] Int. Cl.[7] .............................. C12P 21/06; C12N 1/14; C07K 14/805
[52] U.S. Cl. .................................. 435/69.1; 435/254.11; 435/254.3; 530/385; 514/6
[58] Field of Search .............................. 435/69.1, 254.11, 435/254.3, 254.4; 530/385; 514/6

[56] References Cited

U.S. PATENT DOCUMENTS 5,824,511  10/1998  Mattoon et al. ........................ 435/69.6

FOREIGN PATENT DOCUMENTS

| 0 505 311 | of 0000 | European Pat. Off. |
|---|---|---|
| WO 89/03883 | of 0000 | WIPO . |
| WO 93/25697 | of 0000 | WIPO . |

OTHER PUBLICATIONS

Drygas et al., J. Biol. Chem., vol. 264, No. 30, pp. 17897–17906 (1989).

Myers et al., J. Biol. Chem., vol. 262, No. 35, pp. 16822–16829 (1987).

Verdiere et al., Mol. Gen. Genet., vol. 228, pp. 300–306 (1991).

Amillet et al., Yeast, vol. 11, pp. 419–424 (1995).

Schauer et al., Curr. Genet., vol. 17, No. 1, pp. 1–6 (1990).

Gellerfors et al., J. Biochem., vol. 240, No. 3, pp. 673–677 (1986).

Labbe–Bois, J. Biol. Chem, vol. 265, No. 13, pp. 7278–7283 (1990).

Dailey et al., J. Biol. Chem., vol. 269, No. 2, pp. 813–815 (1994).

Kumar et al., J. Biol. Chem., vol. 255, No. 23, pp. 11130–11134 (1980).

Fowler et al., Mol. Microbiol, vol. 9, No. 5, pp. 989–998 (Sep. 1993).

*Primary Examiner*—Karen Cochrane Carlson
*Attorney, Agent, or Firm*—Steve Zelson, Esq.; Robert L. Starnes; Elias Lambiris, Esq.

[57] ABSTRACT

The present invention relates to methods of producing hemoproteins comprising (a) introducing into a filamentous fungal cell, which is capable of producing the hemoprotein, (i) one or more first control sequences capable of directing the expression of a heme biosynthetic enzyme encoded by a first nucleic acid sequence endogenous to the filamentous fungal cell, wherein the one or more of the first control sequences are operably linked to the first nucleic acid sequence; and/or (ii) one or more copies of one or more second nucleic acid sequences encoding a heme biosynthetic enzyme; (b) cultivating the filamentous fungal cell in a nutrient medium suitable for production of the hemoprotein and the heme biosynthetic enzymes; and (c) recovering the hemoprotein from the nutrient medium of the filamentous fungal cell.

39 Claims, 29 Drawing Sheets

ACCATTGACTCTCAAGCTATGGATCGTGCTCACCGTCTCGGCCAGACAAGACAGGTCACG 60
GTGTATCGCCTGATTACTCGCGGCACCATTGAGGAGCGTATTCGCAAGCGAGCTTTGCAG 120
AAGGAGGAAGTGCAGCGTGTCGTCATCTCAGGTGGCGCAGCTGGTGGGGTTGACTTCAAT 180
ACTCGCAACCGCGAGAGCCGAACCAAGGACATCGCCATGTGGCTGGCAGATGATGAACAG 240
GCGGAGCTTATTGAGCAAAAGGAGAAGGAAGCGCTGGACCGAGGCGAAGTGTTTGGCGCT 300
AGTAAAGGCGGGAAGAAGGCTGCTCAGAAGAGAAAGAGAGATATCACGCTGGATGATATG 360
TATCATGAAGGTATGTGAATCTGATCAAAGCTCTTCGTTCCGGGGAGGCTTCTGGAAATA 420
GTACTAACCGCGTCAATCTATAGGCGAAGGGAACTTTGACGATGCCAGTGCAAAGCCATC 480
AGGAGCGGCCACTCCTGTGTCGACTGCAGAGAATTTAGGCACCCCATCCTCCACGCCAGT 540
TCCTAAACGAGGACGTGGAAGGGGGACAGGAAAGGGCACGTCTAAAAGAGCCAAAACTAC 600
CAAGGAGAGATTACGTCTCATTGATGGCGACGGAGGCTTAGGGCCTAGTTGATTTAATCG 660
ATCTGTGCCTCAATAATGGACACGGCTGGTTATGGTCATGGCGTTCAGAGATTGCATTTC 720
TTTCCCACCCTTTATCTTTCTTTCTTTCCTCTTAAACCCCTCTTTTTTGTTTTTCTTTTT 780
ATCGGACTTTACTTGTGGGCAGCTTACGTTCTGCCTTGTATTAACAGCATATATTCCTGA 840
TTCCTGATGTACGAAGCGATTTAAGAGTCATTGAAGACGAAGGATGAAACCCGTGGTAAT 900
CAGCCGATAATGGCAAAGAGAAGGAGAAGAAAAAAATCAAGTGCGAGTTTTGAAATTGAT 960
GGCAAGATAGACATTGTATCCTGTACCTGTTCTTGGGCTGTGACGGGGGGGGTGAAATTG 1020
ACGGTCATCACCCGGCTATTATTACTATTGTTGTACTGTACATCCGGATCCTGCTGGTCT 1080
GTATCTAGTTAGGGCAATATTCCCCGTCGCCAGGCCTCTTGGGTTATGAATGATTTCATA 1140
GGTGAAGTTTCGTATCCGTACGCACCGAGAGATTTCTTAGTATTACTTGTATTATGAAAA 1200
TGCACTTGCCCGAGTTAAGTCCGCCGGCCAATCACGGCGGAGGATATGGTAAGCCGAAAAG 1260
TCTCGCCGAAGTCCCCGACTTACTCTTACTGGAAGTGGCTTAGTGCCCTCAGCGCCCCCT 1320
CGCCCTCAGTCCATCAGCCAGATTGACTCTTATTTCTCTCTCCTCTTCGCCGCGGGTGAC 1380
ATATCCCTCTCCTTCTCCCTCTCCCTCTTGACAACATTTCATCTTCGCTTCCTTTTGTGA 1440
TATAGTCAGTTTCGCTATCCATTGAAGCATCACTCATGGAGTCTCTTCTCCAGCAGTCCC 1500
                                                                           M  E  S  L  L  Q  S
GGGCGATGTGCCCGTTCCTTAAGCGCACATCTCCATCTTCTCTGCGTACGCTGGCAACCG 1560
 R  A   M  C  P  F  L   K  R  T  S  P  S  S  L  R  T  L  A  T
CGACTCGACCTAGCACTAGTTCCGGTGGAGGCACTATGTCTAATCTCCAGGTCATTGCCC 1620
 R  L  D  L  A  L  V  P  V  E  A  L  C  L  I  S  R  S  L  P
GTCGCTGCCCTGTCATGAGCAAGGCTCTGGCCGTGCAGAGCGCTCGCATGGCCGGTACCA 1680
 R   R  C  P  V  M   S  K  A  L  A  V  Q  S  A  R  M  A  G  T
AAAGATTCACCTCATGTGCTGCCGGCATCACCGGTCTCGGCAACAAGCATTGCCGTGCTC 1740
 K  R  F  T  S  C  A  A  G  I  T  G  L  G  N  K  H  C  R  A
CTACTGGGAAGAGAACCCTGCACTCCACCTCCGGTAACGGCGCCAATGTGAGCGCAGAGA 1800
 P  T  G  K  R  T  L  H  S  T  S  G  N  G  A  N  V  S  A  E
TCTACAAGAACACCCAGCGAGATCCCGCCGGTTTCTCGAAGATCAAGACCCCTGCCAATG 1860
 I  Y  K  N  T  Q  R  D  P  A  G  F  S  K  I  K  T  P  A  N
CTACCGCCGCTGCCGCTACGTCTGGCCCTCGTCCAGAGGCTCCCGTGGCGAAGCCTTTCA 1920
 A  T  A  A  A  A  T  S  G  P  R  P  E  A  P  V  A  K  P  F
ACTACAATTCTTTCTACAACACCGAATTGGAAAAGAAACACAAGGACAAGTCGTATCGCT 1980
 N  Y  N  S  F  Y  N  T  E  L  E  K  K  H  K  D  K  S  Y  R
ATTTCAACAACATCAATCGTCTCGCTCAGGAGTTTCCCCGGGCTCACACCACATCTGCCG 2040
 Y  F  N  N  I  N  R  L  A  Q  E  F  P  R  A  H  T  T  S  A
AGGAACGTGTGACGGTCTGGTGCTCGAACGATTATCTCGGCATGGGCCGCAACCCCGAGG 2100
 E  E  R  V  T  V  W  C  S  N  D  Y  L  G  M  G  R  N  P  E
TTCTGGCCACCATGCATAAGACATTGGACACCTACGGAGCCGGTGCGGGAGGTACTCGCA 2160
 V  L  A  T  M  H  K  T  L  D  T   Y  G  A  G  A  G  G  T  R
ACATTTCAGGTCACAATCAACATGCCGTGAGCCTGGAGAACACCCTGGCCAAATTGCACG 2220
 N  I   S  G  H  N  Q  H  A  V  S  L  E  N  T  L  A  K  L  H
GCAAGGAGGCGGCATTAGTCTTCAGCTCATGCTTCGTGGCTAACGATGCCACCCTCGCAA 2280
 G  K  E  A  A  L  V  F  S  S  C  F  V  A  N  D  A  T  L  A
CCCTGGGTAGCAAGTTGCCCGACTGTGTTATTCTGTCCGATAGCCTGAATCATGCATCGA 2340
 T  L  G  S  K  L  P  D  C  V  I  L  S  D  S  L  N  H  A  S
TGATTCAGGGTATTCGCCATTCAGGCGCCAAGAAAATGGTTTTCAAGCATAATGATCTGG 2400
 M  I  Q  G  I  R  H  S  G  A  K  K  M  V  F  K  H  N  D  L

FIG. 3A

```
TCGACCTTGAGGCCAAGTTGGCAGCTCTACCTCTTCATGTCCCCAAGATTATTGCATTCG 2460
 V  D  L  E  A  K  L  A  A  L  P  L  H  V  P  K  I  I  A  F
AATCAGTTTATAGCATGTGCGGATCTATTGCCCCAATTGAGAAGATCTGTGATCTTGCAG 2520
 E  S  V  Y  S  M  C  G  S  I  A  P  I  E  K  I  C  D  L  A
ACAAGTACGGTGCCATTACTTTCCTGGATGAAGTCCACGCTGTGGGAATGTACGGACCTC 2580
 D  K  Y  G  A  I  T  F  L  D  E  V  H  A  V  G  M  Y  G  P
ACGGAGCAGGTGTGGCAGAGCACCTTGACTATGACATCTATGCTTCCCAAGATACGGTCA 2640
 H  G  A  G  V  A  E  H  L  D  Y  D  I  Y  A  S  Q  D  T  V
ACCCGCGCAGTACTAAGGGAACCGTGATGGACCGAATCGATATTATCACCGGTACTCTGG 2700
 N  P  R  S  T  K  G  T  V  M  D  R  I  D  I  I  T  G  T  L
GCAAGGCCTACGGATGTGTCGGGGGCTACATTGCTGGATCCGCTGCGATGGTTGACACCA 2760
 G  K* A  Y  G  C  V  G  G  Y  I  A  G  S  A  A  M  V  D  T
TCCGCTCCCTCGCCCCTGGCTTCATCTTCACCACGTCCTTGCCGCCCGCCACCATGGCTG 2820
 I  R  S  L  A  P  G  F  I  F  T  T  S  L  P  P  A  T  M  A
GTGCAGACACTGCTATCCAGTACCAGGCTCGTCACCAGGGCGACCGCGTCCTGCAGCAGT 2880
 G  A  D  T  A  I  Q  Y  Q  A  R  H  Q  G  D  R  V  L  Q  Q
TGCACACCCGCGCGGTCAAAGCAGCTTTCAAGGAGTTGGATATTCCTGTAATTCCCAACC 2940
 L  H  T  R  A  V  K  A  A  F  K  E  L  D  I  P  V  I  P  N
CCTCCCATATCATTCCGCTCCTGGTTGGGGATGCCGAGGTTGCTAAGAAGGCCTCGGACA 3000
 P  S  H  I  I  P  L  L  V  G  D  A  E  V  A  K  K  A  S  D
AGCTTCTGGAGGAGCATGGAATTTATGTACAAGCCATCAACTACCCAACCGTGCCTCGGG 3060
 K  L  L  E  E  H  G  I  Y  V  Q  A  I  N  Y  P  T  V  P  R
GTGAAGAGCGGCTTCGTATCACGCCCACCCCGGGACATATCAAGGAGCACCGCGACCACC 3120
 G  E  E  R  L  R  I  T  P  T  P  G  H  I  K  E  H  R  D  H
TGGTGCAAGCCGTCCAAACAGTCTGGAACGAACTGGGCATCAAACGCACCAGCGATTGGG 3180
 L  V  Q  A  V  Q  T  V  W  N  E  L  G  I  K  R  T  S  D  W
AAGCGCAAGGCGGCTTCGTCGGCGTGGGTGTCGATGGCGCCGAGGCTGAGAACCAGCCGA 3240
 E  A  Q  G  G  F  V  G  V  G  V  D  G  A  E  A  E  N  Q  P
TTTGGAATGATGTGCAGCTGGGGCTGAAGGAAAACGAAGCCATTGAGGCTGCTGTGGAAC 3300
 I  W  N  D  V  Q  L  G  L  K  E  N  E  A  I  E  A  A  V  E
GCGAGTTTGCCGAGGCCCCCATGCGGACCGCCACCCGTCCTGCCGCGGCTGCTGCTTCGT 3360
 R  E  F  A  E  A  P  M  R  T  A  T  R  P  A  A  A  A  S
CAATCCCGGTGGGTGTGGCTGCCTGAAGTGGCTGCCCGCATGTGAGCTGAAATCGACGTG 3420
 S  I  P  V  G  V  A  A
GAATTCTATACACACACACACACACACACACACACACACACACACACACACACACACACA 3480
CACACACACACACACACACTAACACACACTATGTTATAAATTCCACATCCACTCCTTTGT 3540
CCCTTGTTGGACGTAATTGGTATTTGGACTATTAGTTAGAACCAGTCAGTCGTTACCATG 3600
TGTTTCGGTTCGACTCGAAATCTGACATGTTGTCTGCCCCATGCCACTTCATCTCCTCC 3660
GTAACCGCAGGGCTTCAAATACACTGCCCAGTAATTGTAGTCAATATAGCAGTTAACTAA 3720
CCTTCACCAATTTCCTAATAACAATAGAAGGGGCCATACACGCAGTACCAAAGATCACCT 3780
ACCTCCGATCAATATCCGAACCTCAGGCTACATACATCAAGTCGCATTAATCGATTCCGA 3840
CCTCTGTTTATCCCTGAAAATAACTAAGATCATGATCTACGTTTGGTAAGTGGGACAECT 3900
ACCTACACTGGGAGGTATTGAATAAAGGCATCATTCATATAGTCACAAGATGCCAGGGCC 3960
AATTCATGATATGGATAGCTACTTCCAAACATAATTCAGAGGTATCATTCTGCTCTTCAG 4020
ACAGTTCTTCTCGAAGATCAGTAGGAGCCAGTTTTGACCATTAACTTGTAATGTAATTGC 4080
GATTGTAGTAGATCCGAGATCCATTCACTTTCTAAGGGTTAATTGATTCATTTTACTGAT 4140
ACCTCACCCACCATATT                                             4157
```

FIG. 3B

```
A. oryzae          M E S - - - - L L Q Q S R A M C P F L K R T S P S S L R T L   26
A. nidulans        M E A - - - - L L Q Q S R A M C P F L K R S S P N T L R S L   26
chicken erythroid  M A A - - - - F L - - - - - R C P L L A R H P P L A - R A F   20
human erythroid    M V T A A M L L Q - - - - - C C P V L A R G P T S L L G K V   25
mouse erythroid    M V A A A M L L W - - - - - S C P V L S Q G P T G L L G K V   25
chicken hepatic    M E A - - - V V R - - - - - R C P F L A R V S Q A F L Q K A   22
human hepatic      M E S - - - V V R - - - - - R C P F L S R V P Q A F L Q K A   22
rat hepatic        M E T - - - V V R - - - - - R C P F L S R V P Q A F L Q K A   22

A. oryzae          A - - - - - - - T - - - - - A T R P S T S S G G G T M S N L   44
A. nidulans        A - - - - - - - T - - - - - A T R P S T S P G G G T M T N L   44
chicken erythroid  A - - - - - - - T - - - - - G A - - - - - - - - - - - - - -   24
human erythroid    V K T H Q F L F G - - - - - I G - - - - - - - - - - - - - -   36
mouse erythroid    A K T Y Q F L F S - - - - - I G - - - - - - - - - - - - - -   36
chicken hepatic    G - - - - - - - P S L L F Y A Q - - - - - - - - - - - - - -   31
human hepatic      G - - - - - - - K S L L F Y A Q - - - - - - - - - - - - - -   31
rat hepatic        G - - - - - - - K S L L F Y A Q - - - - - - - - - - - - - -   31

A. oryzae          Q V I A R R C P V M S - - - - - - - - - - - K A L A V Q S A   63
A. nidulans        Q R I A R R C P V M S - - - - - - - - - - - K A L A V Q S A   63
chicken erythroid  - - - - - R C P F M G - - - - - - - - - - - F A - H R A A P   37
human erythroid    - - - - - R C P I L A T Q G P N C S Q I H L K A - T K A G G   60
mouse erythroid    - - - - - R C P I L A T Q G P T C S Q I H L K A - T K A G G   60
chicken hepatic    - - - - - H C P K M M - - - - - - - - - - - E A - A P P A A   44
human hepatic      - - - - - N C P K M M - - - - - - - - - - - E V - G A K P A   44
rat hepatic        - - - - - N C P K M M - - - - - - - - - - - E V - G A K P A   44

A. oryzae          - - - - - - - - - - - - - - - - - R - - M                     65
A. nidulans        - - - - - - - - - - - - - - - - - R - - M                     65
chicken erythroid  - - - - - - - - - - - - - - - - - E - - L                     39
human erythroid    D S P S W A K G H C P F M L S E - - L Q D G K S K I V Q - K   87
mouse erythroid    - - - - - - - - - - - - - - - E - - L Q D R K S K I V Q - R   72
chicken hepatic    - - - - - - - - - - - - - - - - - A R G L A T S A S R G Q Q V E   59
human hepatic      - - - - - - - - - - - - - - - - - P R A L S T A A V H Y Q Q I K   59
rat hepatic        - - - - - - - - - - - - - - - - - P R T V S T S A A Q C Q Q V K   59

A. oryzae                                                                         65
A. nidulans                                                                       65
chicken erythroid                                                                 39
human erythroid    A A P E V Q E D V K A F K T D L P S S L V S V S - - L R - -   113
mouse erythroid    A A P E V Q E D V K T F K T D L L S T M D S T T - - R S - -   98
chicken hepatic    E T P A A Q P E A K K A K E V A Q Q N T D G S Q - - P P - -   85
human hepatic      E T P P A S E K D K T A K A K V Q Q T P D G S Q - - Q S P D   87
rat hepatic        E T P P A N E K E K T A K A A V Q Q A P D E S Q M A Q T P D   89

A. oryzae                                                                         65
A. nidulans                                                                       65
chicken erythroid                                                                 39
human erythroid    - - - - - K P F S G P Q E Q E Q I S G K V T H L I Q N - N M   137
mouse erythroid    - - - - - H S F P S F Q E P E Q T E G A V P H L I Q N - N M   122
chicken hepatic    - - - - - A G H P P A A A V Q S S A T K C P F L A A Q M N H   110
human hepatic      G T Q L P S G H P L P A T S Q G T A S K C P F L A A Q M N Q   117
rat hepatic        G T Q L P P G H P S P S T S Q S S G S K C P F L A A Q L A R   119

A. oryzae                                                                         65
A. nidulans                                                                       65
chicken erythroid                                                                 39
human erythroid    P G N Y V F S Y D - - Q F F R                                 150
mouse erythroid    T G S Q A F G Y D - - Q F F R                                 135
chicken hepatic    K S S N V F C K A - - S L E L                                 123
human hepatic      R G S S V F C K A - - S L E L                                 130
rat hepatic        R A A A S S A R P V W S F R R                                 134
```

FIG. 4

```
A. nidulans    M - - E A L L Q Q S R A M C P F L K R S S P N T L R S L A T   28
A. oryzae      M - - E S L L Q Q S R A M C P F L K R T S P S S L R T L A T   28
human          M V T A A M L L Q C - - - C P V L A R G P T S L L G K V V K   27
S. cerevisae   M - - Q - - - - - - - - - - - - - - - - - - - - R S I F A    7

A. nidulans    A T R P S T S P G G G T M T N L Q R I A R R C P V M S - K A   57
A. oryzae      A T R P S T S S G G G T M S N L Q V I A R R C P V M S - K A   57
human          T H Q F L F G I G - - - - - - - - - - - - R C P I L A T Q G   45
S. cerevisae   - - - - - - - - - - - - - - - - - - - - - - - - - - - - -     7

A. nidulans    L A V Q S A R M T G T K R F T S S A A G V P G A G A G T P K   87
A. oryzae      L A V Q S A R M A G T K R F T S C A A G I T G L G N - - - K   84
human          P N C S Q I H L K A T K A G G D S P S W A K G H C P F M L S   75
S. cerevisae   - - - - - - - - - - R F G N S S A A V S T L N R L S T T       25

A. nidulans    P T R G S P G K R A L H S T G G N G A N M S T E F H K G A Q   117
A. oryzae      H C R A P T G K R T L H S T S G N G A N V S A E I Y K N T Q   114
human          E L Q D G K S K - I V Q K A A P E V Q E D V K A F K T D L P   104
S. cerevisae   A - - A P H A K N G Y A T A T G A G A A A T A - - - - - -     47

A. nidulans    Q I H P G L S N A - T R S H V G A S A T V S G P T P R - - -   143
A. oryzae      R D P A G F S K I K T P A N A T A A A A T S G P R P E - - -   141
human          S S L V S V S L R K P F S G P Q E Q E Q I S G K V T H L I Q   134
S. cerevisae   - - - - - - - - - - T A S S T H A A A A A A A A A N H - - -   64

A. nidulans    - - A P V A A P F D Y D A F Y N A E L Q K K H Q D K S Y R Y   171
A. oryzae      - - A P V A K P F N Y N S F Y N T E L E K K H K D K S Y R Y   169
human          N N M P G N Y V F S Y D Q E F R D K I M E K Q D H T Y R V     164
S. cerevisae   - - S T Q E S G F D Y E G L I D S E L Q K K R L D K S Y R Y   92

A. nidulans    F N N I N R L A Q E F P R A H T - - - - A S K D E K V T V W   197
A. oryzae      F N N I N R L A Q E F P R A H T - - - - T S A E E R V T V W   195
human          F K T V N R W A D A Y P F A Q H F F E A S V A S K D V S V W   194
S. cerevisae   F N N I N R L A K E F P L A H R - - - - Q R E A D K V T V W   118

A. nidulans    C S N D Y L G M G R N P E V L A T M H K T L D T Y G A G A G   227
A. oryzae      C S N D Y L G M G R N P E V L A T M H K T L D T Y G A G A G   225
human          C S N D Y L G M S R H P Q V L Q A T Q E T L Q R H G A G A G   224
S. cerevisae   C S N D Y L A L S K H P E V L D A M H K T I D K Y G C G A G   148

A. nidulans    G T R N I S G H N Q H A V S L E N T L A K L H G K E A A L V   257
A. oryzae      G T R N I S G H N Q H A V S L E N T L A K L H G K E A A L V   255
human          G T R N I S G T S K F H V E L E Q E L A E L H Q K D S A L L   254
S. cerevisae   G T R N I A G H N I P T L N L E A E L A T L H K K E G A L V   178
```

FIG. 5A

| | | |
|---|---|---|
| A. nidulans | F S S C F V A N D A T L A T L G S K M P D C V I L S D S L N | 287 |
| A. oryzae | F S S C F V A N D A T L A T L G S K L P D C V I L S D S L N | 285 |
| human | F S S C F V A N D S T L F T L A K I L P G C E I Y S D A G N | 284 |
| S. cerevisae | F S S C Y V A N D A V L S L L G Q K M K D L V I F S D E L N | 208 |
| | | |
| A. nidulans | H A S M I Q G I R H S G R K K M V F K H N D L V D L E T K L | 317 |
| A. oryzae | H A S M I Q G I R H S G A K K M V F K H N D L V D L E A K L | 315 |
| human | H A S M I Q G I R N S G A A K F V F R H N D P D H L K K L L | 314 |
| S. cerevisae | H A S M I V G I K H A N V K K H I F K H N D L N E L Q L L | 238 |
| | | |
| A. nidulans | A S L P L H V P K I I A F E S V Y S M C G S I A P I E A I C | 347 |
| A. oryzae | A A L P L H V P K I I A F E S V Y S M C G S I A P I E K I C | 345 |
| human | E K S N P K I P K I V A F E T V H S M D G A I C P L E E L C | 344 |
| S. cerevisae | Q S Y P K S V P K L I A F E S V Y S M A G S V A D I E K I C | 268 |
| | | |
| A. nidulans | D L A D K Y G A I T F L D E V H A V G M Y G P H G A G V A E | 377 |
| A. oryzae | D L A D K Y G A I T F L D E V H A V G M Y G P H G A G V A E | 375 |
| human | D V S H Q Y G A L T F V D E V H A V G L Y G S R G A G I G E | 374 |
| S. cerevisae | D L A D K Y G A L T F L D E V H A V G L Y G P H G A G V A E | 298 |
| | | |
| A. nidulans | H L D Y E I Y A S Q D T A N P L S T - K G - - - T V M D R I | 403 |
| A. oryzae | H L D Y D I Y A S Q D T V N P R S T - K G - - - T V M D R I | 401 |
| human | R - - - - - - - - - - - - - - - - - - - - D G I M H K I | 382 |
| S. cerevisae | H C D F E S H R A S G I A T P K T N D K G A K T V M D R V | 328 |
| | | |
| A. nidulans | N I I T G T L G K A Y G C V G G Y I A G S A A L V D T I R S | 433 |
| A. oryzae | D I I T G T L G K A Y G C V G G Y I A G S A A M V D T I R S | 431 |
| human | D I I S G T L G K A F G C V G G Y I A S T R D L V D M V R S | 412 |
| S. cerevisae | D M I T G T L G K S F G S V G G Y V A A S R K L I D W F R S | 358 |
| | | |
| A. nidulans | L A P G F I F T T S L P P A T M A G A D T A I R Y Q A R H Q | 463 |
| A. oryzae | L A P G F I F T T S L P P A T M A G A D T A I Q Y Q A R H Q | 461 |
| human | Y A A G F I F T T S L P P M V L S G A L E S V R L L K G E E | 442 |
| S. cerevisae | F A P G F I F T T T L P P S V M A G A T A A I R Y Q R C H I | 388 |
| | | |
| A. nidulans | Q D - - R I L Q Q L H T R A V K Q S F K D L D I P V I P N P | 491 |
| A. oryzae | G D - - R V L Q Q L H T R A V K A F K E L D I P V I P N P | 489 |
| human | G Q A L R R A H Q R N V K H M R Q L L M D R G L P V I P C P | 472 |
| S. cerevisae | D L - - R T S Q Q K H T M Y V K A F H E L G I P V I P N P | 416 |
| | | |
| A. nidulans | S H I V P L L V G D A E L A K Q A S D K L L E E H G I Y V Q | 521 |
| A. oryzae | S H I I P L L V G D A E V A K K A S D K L L E E H G I Y V Q | 519 |
| human | S H I I P I R V G N A A L N S K L C D L L L S K H G I Y V Q | 502 |
| S. cerevisae | S H I V P V L I G N A D L A K Q A S D I L I N K H Q I Y V Q | 446 |

FIG. 5B

```
A. nidulans   A I N Y P T V P R G E E R L R I T P T P G H T Q E L R D H L   551
A. oryzae     A I N Y P T V P R G E E R L R I T P T P G H I K E H R D H L   549
human         A I N Y P T V P R G E E L L R L A P S P H H S P Q M M E D F   532
S. cerevisae  A I N F P T V A R G T E R L R I T P T P G H T N D L S D I L   476

A. nidulans   V E A V N T V W N D L G I K R A S D W K A M G G F V G V G V   581
A. oryzae     V Q A V Q T V W N E L G I K R T S D W E A Q G G F V G V G V   579
human         V E K L L L A W T A V G L P - - - - - - - - - L Q D V S V     552
S. cerevisae  I N A V D D V F N E L Q L P R V R D W E S Q G G L L G V G -   505

A. nidulans   E A A E L E N Q P I W T D A Q L N M R P D E T L E A A V E R   611
A. oryzae     D G A E A E N Q P I W N D V Q L G L K E N E A I E A A V E R   609
human         A A C N F C R R P V - - - - H F E L M S E - - - - - - W E R   572
S. cerevisae  E S G F V E E S N L W T S S Q L S L T N D D - L N P N V - -   532

A. nidulans   E F Q A A V P G M K A G G A K A K P V G S I A A N P I G A S   641
A. oryzae     E F A E A - - - - - - - - - - P M R T A T R P A A A A S S     629
human         S Y F G N M - - - - - - - - - - - - - - - - - - - - - - G   579
S. cerevisae  - - - - - - - - - - - - - - - - - R D P I V K Q L E V S S G   545

A. nidulans   I P V A - A A A                                               648
A. oryzae     I P V G V A A .                                               637
human         P Q Y V T T Y A                                               587
S. cerevisae  I K - - - - - Q                                               548
```

Decoration 'Decoration #1': Box residues that match the Consensus exactly.

FIG. 5C

```
CTGGACCAATGGTAACCCTCCGTAATTGCCTTACAGATTTAGCCCAGGGGGGTTATGGTATCCTTGGGTA    70
TTGAGGCCTGGAAATTTTTTTAGCCACCAGTTTACAGCCAGTTTCCGTTTGTAAATATTTCACATCCCCC   140
GACCCTGTCCCAATACAATAATTTTTTCGCTATATATAACGCCCCTAGCGTTGTTTTATGATCCTTAAAT   210
CCTTACTTGTACCTGAAAATTGCAACAAATGTACTGACCTGGATCGCTGGCCATTTATATCATTGCCCTG   280
CGAAGTCGTATTCTGCCAGTGGCACAGGCGCTATTCTCTTTTCTTCCCTCCACCGCGTTTCTATCTTCCA   350
TAGCACCCCACTTGCTTGCCGCTCCTGTCATTATGTCCTTTTCTAATCTCGTCTCTGACCTCGCCTTCAG   420
                                    M  S  F  S  N  L  V  S  D  L  A  F  R
AGATTCTCATGATGACCGAAGTTCTCAGATATCTCAGGTACAATCGCAAGCCACTGCACGATCGTATACA   490
 D  S  H  D  D  R  S  S  Q  I  S  Q  V  Q  S  Q  A  T  A  R  S  Y  T
AGCACAGCTGCCACAAGCGTCAGCATATCTGGCGACATCTCAAGCCAGCTTCATTCCGGTTACAGCCATC   560
 S  T  A  A  T  S  V  S  I  S  G  D  I  S  S  Q  L  H  S  G  Y  S  H
CACTGAGCCGATCATGGCAGGCTGAAAGACAGTTGACTAAAGTCCGCATTTTCTTTTGTATTTACTGAGC   630
 P  L  S  R  S  W  Q  A  E  R  Q  L  T  K
TGCTCTAACCCCGAGATAGGAAATGCTTATTTATCCTCTCTTCATCACCGATAATCCCGATGAGGAGACT   700
                         E  M  L  I  Y  P  L  F  I  T  D  N  P  D  E  E  T
CCTATCCCGTCTCTCCCTGGACAGTATCGTCGAGGATTAAACCGTCTAGTTCCTTTCATCAAACCACTTG   770
 P  I  P  S  L  P  G  Q  Y  R  R  G  L  N  R  L  V  P  F  I  K  P  L
CCCACAAGGGGCTACGCTCAGTCATCCTGTTTGGCGTCCCACTACACCCCTCTGCGAAGGATGCACTAGG   840
 A  H  K  G  L  R  S  V  I  L  F  G  V  P  L  H  P  S  A  K  D  A  L  G
TACCGCTGCAGACGATCCATCTGGACCGGTAATTCAAGCTATTCGCTTGCTTAGGTCGCGGTTTCCTCAA   910
 T  A  A  D  D  P  S  G  P  V  I  Q  A  I  R  L  L  R  S  R  F  P  Q
CTTTATATCGTGACAGATGTGTGCCTTTGCGAGTATACTTCGCATGGCCACTGTGGGATACTGCGAGAAG   980
 L  Y  I  V  T  D  V  C  L  C  E  Y  T  S  H  G  H  C  G  I  L  R  E
ATGGGACTCTTGATAATACACAGTCTGTGGATCGGATTTCGGATGTTGCTCTGGCTTATGCTGCCGCCGG  1050
 D  G  T  L  D  N  T  Q  S  V  D  R  I  S  D  V  A  L  A  Y  A  A  A  G
AGCCCATTGTGTCGCTCCGTCTGATATGAATGATGGGCGAGTGCGTGCTATAAAACTGAAGCTTATTGAA  1120
 A  H  C  V  A  P  S  D  M  N  D  G  R  V  R  A  I  K  L  K  L  I  E
GCCGGGATGGCCCACCGTGTCCTACTGATGTCCTACAGCGCCAAATTTAGCGGTTGTTTGTACGGCCCTT  1190
 A  G  M  A  H  R  V  L  L  M  S  Y  S  A  K  F  S  G  C  L  Y  G  P
TCCGTGATGCAGCGGGGTCCTGCCCATCATTCGGGGATCGCAGATGCTACCAGTTACCACCCGGAGGCCG  1260
 F  R  D  A  A  G  S  C  P  S  F  G  D  R  R  C  Y  Q  L  P  P  G  G  R
TGGACTTGCTCGGCGCGCTATACAGAGAGATATAGGCGAAGGGGCAGACATCATAATGGTAAAGCCGGCG  1330
 G  L  A  R  R  A  I  Q  R  D  I  G  E  G  A  D  I  I  M  V  K  P  A
AGCAGCTACCTGGACATTATCAGAGACGCAAAAGAAATTGCCAAAGACATTCCCATTGCTGCTTACCAGG  1400
 S  S  Y  L  D  I  I  R  D  A  K  E  I  A  K  D  I  P  I  A  A  Y  Q
TCAGCGGTGAGTATGCTATGATACATGCTGGTGCCAAGGCGGGCGTATTTGACTTGAAATCCATGGCCTT  1470
 V  S  G  E  Y  A  M  I  H  A  G  A  K  A  G  V  F  D  L  K  S  M  A  F
TGAAAGTACTGAAGGGATTATAAGGGCTGGTGCTGGGATTATAGTAAGCTATTTCGTGCCTGATTTTCTA  1540
 E  S  T  E  G  I  I  R  A  G  A  G  I  I  V  S  Y  F  V  P  D  F  L
GATTGGCTTTCGAAATGATTTAGCTAGATGGAGCGTGATGAAAGCATCCACCAGATAAATAGCAGTGACG  1610
 D  W  L  S  K
ATCGCGTTTGAATCATACCTATTGGAGTAGAAGTCTCGGTATCTCGTTGGGGATTCTCTAGGTTGCTTAT  1680
TTAACGTAATGCCACGCCATGTGTTATATATTGCCTAAATACTTTTATAAAAGATACACCAAGCTGATGG  1750
TGCCAAGTGACCACTTCTAATAAATACAATTATACCAATTCCTCCGAAATATGCGGG    1807
```

FIG. 12

```
B. subtilis hemB   M S Q S F - - - - - - - - - - - - - - - - - - - - - - - - - - -   5
E. coli hemB       - T D L I - - - - - - - - - - - - - - - - - - - - - - - - - - -   4
human hemB         M - - - - - - - - - - - - - Q P Q - - - - - - - - - - -           4
pea hemB           - - - - - - - - - - - - - H T F V D L K S P F T L S N Y          15
rat hemB           M - - - - - - - - - - - - - H H Q - - - - - - - - - - -           4
spinach hemB       M M A S T F N I P C N A G T I K N F N N S Q R N L G F S S N      30
yeast hemB         M - - - - - - - - - - - - - H T A E F L E - - - - - - -           8
Ao hemB            M - - - - - - - - - - - - S F S N L V S D L A F R D -            14

B. subtilis hemB   - - - - - - - - - - - - - - - - - - - - - - - - - - - - - -      5
E. coli hemB       - - - - - - - - - - - - - - - - - - - - - - - - - - - - - -      4
human hemB         - - - - - - - - - - - - - - - - - - - - - - - - - - - - - -      4
pea hemB           L S F S S S K R R - - - - - - - Q P P S L F T V R A S D S        37
rat hemB           - - - - - - - - - - - - - - - - - - - - - - - - - - - - - -      4
spinach hemB       L G I N F A K T R F S N C G D S G R I P S Q L V V R A S E R      60
yeast hemB         - - - - - - - - - - - - - - - - - - - - - - - - - - - - - -      8
Ao hemB            - - - - - - - - - - - - - - - - - - - - - S H D D R             19

B. subtilis hemB   - - - - - - - - - - - - - - - - - - - - - - - - - - - - - -      5
E. coli hemB       - - - - - - - - - - - - - - - - - - - - - - - - - - - - - -      4
human hemB         - - - - - - - - - - - - - - - - - - - - - - - - - - - - - -      4
pea hemB           - - - - - - - - - - - - - - D F E A A V V A G K V P E A P P     53
rat hemB           - - - - - - - - - - - - - - - - - - - - - - - - - - - - - -      4
spinach hemB       R D N L T Q Q K T G L S I E E C E A A V V A G N A P S A P P     90
yeast hemB         - - - - - - - - - - - - - - - - - - - - - - - - - - - - - -      8
Ao hemB            S S Q I S Q V Q S Q A T A R S Y T S T - - - - - - - - - -       38

B. subtilis hemB   - - - - - - - - - - - - - - - - - - N R H R R L R T S K         15
E. coli hemB       - - - - - - - - - - - - - - - - - - Q R P R R L R K S P         14
human hemB         - - - - - - - - - - - - S V L H S G Y F H P L L R A W Q         20
pea hemB           V P P T P A S P A G T P V V P S L P I Q R P R N R R S P         83
rat hemB           - - - - - - - - - - - - S V L H S G Y F H P L L R A W Q         20
spinach hemB       V P P T P K A P S G T P S V S P L S L G R R P R R N R T S P    120
yeast hemB         - - - - - - - T E P T E I S S V L A G G Y N H P L L R Q W Q    31
Ao hemB            - - A A T S V S I S G D I S S Q L H S G Y S H P L S R S W Q    66

B. subtilis hemB   A M R E M V K E T R L H P S D F I Y P I F V V E G L E G K K     45
E. coli hemB       A L P R M F E E T T L S L N D L V L P I F V E E E I D D Y K     44
human hemB         T - - - - - A T T T L N A S N L I Y P I F V T D V P D D I Q     45
pea hemB           A L R S A F Q E T T L S P A N F V Y P L F I H E G E E D - T    112
rat hemB           T - - - - - T P S T V S A T N L I Y P I F V T D V P D D V Q     45
spinach hemB       V F R A A F Q E T T L S P A N V V Y P L F I H E G E E D - T    149
yeast hemB         - - - - - - S E R Q L T K N M L I F P L F I S D N P D D F T     55
Ao hemB            - - - - - - A E R Q L T K E M L I Y P L F I T D N P D E E T     90
```

FIG. 13A

```
B. subtilis hemB   A V P S M P D V H H V S L D L - L K D E V A E L V K L G I Q    74
E. coli hemB       A V E A M P G V M R I P E K H - L A R E I E R I A N A G I R    73
human hemB         P I T S L P G V A R Y G V K R - L E E M L R P L V E E G L R    74
pea hemB           P I G A M P G C Y R L G W R H G L L E E V A K A R D V G V N   142
rat hemB           P I A S L P G V A R Y G V N Q - L E E M L R P L V E A G L R    74
spinach hemB       P I G A M P G C Y R L G W R H G L V E E V A K A R D V V V N   179
yeast hemB         E I D S L P N I N R I G V N R - L K D Y L K P L V A K G L R    84
Ao hemB            P I P S L P G Q Y R R G L N R - L V P F I K P L A H K G L R   119

B. subtilis hemB   S V I V F G - - I P E E - K D D C G T Q A Y H D H G I V Q K   101
E. coli hemB       S V M T F G - - I S H H - T D E T G E R A W R E D G L V A R   100
human hemB         C V L I F G V P - S R V P K D E R G S A A D S E E S P A I E   103
pea hemB           S V V L F P - K I P D A L K T P T G D E A Y N E D G L V P R   171
rat hemB           C V L I F G V P - S R V P K D E Q G S A A D S E D S P T I E   103
spinach hemB       S I V V F P - K - P D A L K S P T G D E A Y N E N G L V P R   207
yeast hemB         S V I L F G V P L I P G T K D P V G T A A D D P A G P V I Q   114
Ao hemB            S V I L F G V P L H P S A K D A L G T A A D D P S G P V I Q   149

B. subtilis hemB   A I T E I K E H F P E M V V V A D T C L C E Y T D H G H C G   131
E. coli hemB       M S R I C K Q T V P E M I V M S D T C F C E Y T S H G H C G   130
human hemB         A I H L L R K T F P N L L V A C D V C L C P Y T S H G H C G   133
pea hemB           S I R L L K D K Y P D L I I Y T D V A L D P Y S S D G H D G   201
rat hemB           A V R L L R K T F P T L L V A C D V C L C P Y T S H G H C G   133
spinach hemB       T I R M L K D K F P D L I I Y T D V A L D P Y Y Y D G H D G   237
yeast hemB         G I K F I R E Y F P E L Y I I C D V C L C E Y T S H G H C G   144
Ao hemB            A I R L L R S R F P Q L Y I V T D V C L C E Y T S H G H C G   179

B. subtilis hemB   L V K D G V - I L N D E S L E L L A Q T A V S Q A K A G A D   160
E. coli hemB       V L C E H G - V D N D A T L E N L G K Q A V V A A A G A D   159
human hemB         L L S E N G A F R A E S R Q R L A E V A L A Y A K A G C Q   163
pea hemB           I V R E D G V I M N D E T V H Q L C K Q A V A Q A R A G A D   231
rat hemB           L L S E N G A F L A E S R Q R L A E V A L A Y A K A G C Q   163
spinach hemB       I V T Q H G V I M N D E T V H Q L C K Q A V A Q A R A G A D   267
yeast hemB         V L Y D D G T I N R E R S V S R L A A V A V N Y A K A G A H   174
Ao hemB            I L R E D G T L D N T Q S V D R I S D V A L A Y A A A G A H   209

B. subtilis hemB   I I A P S N M M D G F V T V I R E A L D K E G F V N - I P I   189
E. coli hemB       F I A P S A A M D G Q V Q A I R Q A L D A A G F K D - T A I   188
human hemB         V V A P S D M M D G R V E A I K E A L M A H G L G N R V S V   193
pea hemB           V V S P S D M M D G R V G A M R V A L D A E G F Q H - V S I   260
rat hemB           V V A P S D M M D G R V E A I K A A L L K H G L G N R V S V   193
spinach hemB       V V S P S D M M D G R V G A I R A A L D A E G Y S N - V S I   296
yeast hemB         C V A P S D M I D G R I R D I K R G L I N A N L A H K T F V   204
Ao hemB            C V A P S D M N D G R V R A I K L K L I E A G M A H R V L L   239
```

FIG. 13B

```
B. subtilis hemB  M S Y A V K Y S S E F Y G P F R D A A N S T P Q F G D R K T  219
E. coli hemB      M S Y S T K F A S S F Y G P F R E A A G S A L K - G D R K S  217
human hemB        M S Y S A K F A S C F Y G P F R D A A K S S P A F G D R R C  223
pea hemB          M S Y T A K Y A S S F Y G P F R E A L D S N P R F G D K K T  290
rat hemB          M S Y S A K F A S C F Y G P F R D A A Q S S P A F G D R R C  223
spinach hemB      M S Y T A K Y A S S F Y - - - - - - - - - - P R F G D K K T  316
yeast hemB        L S Y A A K F S G N L Y G P F R D A A C S A P S N G D R K C  234
Ao hemB           M S Y S A K F S G C L Y G P F R D A A G S C P S F G D R R C  269

B. subtilis hemB  Y Q M D P A N R M E A L R E A Q S D V E E G A D F L I V K P  249
E. coli hemB      Y Q M N P M N R A E G I A E Y L L D E A Q G A D C L M V K P  247
human hemB        Y Q L P P G A R G L A L R A V D R D V R E G A D M L M V K P  253
pea hemB          Y Q M N P A N Y R E A L T E M R E D E S E G A D I L L V K P  320
rat hemB          Y Q L P P G A R G L A L R A V A R D I Q E G A D I L M V K P  253
spinach hemB      Y Q M N P A N Y R E A L I E T Q E D E S E G A D I L L V K P  346
yeast hemB        Y Q L P P A G R G L A R R A L E R D M S E G A D G I I V K P  264
Ao hemB           Y Q L P P G G R G L A R R A I Q R D I G E G A D I M V K P  299

B. subtilis hemB  S L S Y M D I M R D V K N E F - T L P L V A Y N V S G E Y S  278
E. coli hemB      A G A Y L D I V R E L R E R T - E L P I G A Y Q V S G E Y A  276
human hemB        G M P Y L D I V R E V K D K H P D L P L A V Y H V S G E F A  283
pea hemB          G L P Y L D I I R L L R D N S - P L P I A A Y Q V S G E Y S  349
rat hemB          G L P Y L D M V Q E V K D K H P E L P L A V Y Q V S G E F A  283
spinach hemB      G L P Y L D I I R L L R D N S - D L P I A A Y Q V S G E Y S  375
yeast hemB        S T F Y L D I M R D A S E I C K D L P I C A Y H V S D E Y A  294
Ao hemB           A S S Y L D I I R D A K E I A K D I P I A A Y Q V S G E Y A  329

B. subtilis hemB  M V K A A Q N G W I K E K E I V L E I L T S M K R A G A D  308
E. coli hemB      M I K F A A L A G A I D E E K V V L E S L G S I K R A G A D  306
human hemB        M L W H G A Q A G A F D L K A A V L E A M T A F R R A G A D  313
pea hemB          M I K A G G A L K M I D E E K V M M E S L L C L R R A G A D  379
rat hemB          M L W H G A K A G A F D L R T A V L E S M T A F R R A G A D  313
spinach hemB      M I K A G V L K M I D E E K V M L E S L L C L R R A G A D  405
yeast hemB        M L H A A E K G V V D L K T I A F E S H Q G F L R A G A R  324
Ao hemB           M I H A G A K A G V F D L K S M A F E S T E G I I R A G A G  359

B. subtilis hemB  L I I T Y H A K D - A A K W L - - - A E                    324
E. coli hemB      L I F S Y F A L D L A E K K I - - - L R                    323
human hemB        I I I T Y Y T P Q L L - Q W L - K E E                      330
pea hemB          I I L T Y F A L Q - A A R T L C G E K R                    398
rat hemB          I I I T Y F A P Q L L - K W L - K E E                      330
spinach hemB      I I L T Y F A L Q - A A R C L C G E K R                    424
yeast hemB        L I I T Y L A P E F L - D W L - D E E N                    342
Ao hemB           I I V S Y F V P D F L - D W L - S - - K                    375
```

Decoration 'Decoration #1': Box residues that match the Consensus exactly.

FIG. 13C

METHOD FOR INCREASING HEMOPROTEIN PRODUCTION IN FILAMENTOUS FUNGI

CROSS-REFERENCE TO RELATED APPLICATIONS

This application is a continuation-in-part of application Ser. No. 08/662,752 filed Jun. 10, 1996 now abandoned and of Ser. No. 60/041,158 filed Mar. 17, 1997 now abandoned, the contents of which are fully incorporated herein by reference.

BACKGROUND OF THE INVENTION

1. Field of the Invention

The present invention relates to methods of producing hemoproteins in filamentous fungi and to filamentous fungal cells capable of producing hemoproteins.

2. Description of the Related Art

Heme, a chelate complex of protoporphyrin IX and iron, serves as a prosthetic group of hemoproteins. Protoporphyrin IX consists of a porphyrin ring, substituted with four methyl groups, two vinyl groups, and two propionic acid groups, which acquires an iron atom to form heme. The biosynthesis of heme from glycine and succinyl-CoA involves eight enzymatic steps which are catalyzed by 5-aminolevulinic acid synthase (EC 2.3.1.37), porphobilinogen synthase (EC 4.2.1.24), porphobilinogen deaminase (EC 4.3.1.8), uroporphyrinogen III synthase (EC 4.2.11.75), uroporphyrinogen III decarboxylase (EC 4.1.1.37), coproporphyrinogen III oxidase (EC 1.3.3.3), protoporphyrinogen IX oxidase (EC 1.3.3.4), and ferrochelatase (EC 4.99.1.1). 5-Aminolevulinic acid synthase catalyzes the condensation of glycine and succinyl-CoA to form 5-aminolevulinic acid. Porphobilinogen synthase (also called 5-aminolevulinic acid dehydratase or 5-aminolevulinic acid dehydrase) catalyzes the condensation of two molecules of 5-aminolevulinic acid to form porphobilinogen. Porphobilinogen deaminase (also called hydroxymethylbilane synthase or uro I synthase) catalyzes the tetrapolymerization of pyrole porphobilinogen into preuroporphyrinogen. Uroporphyrinogen III synthase (also called uro III synthase or uro III cosynthase) catalyzes a rearrangement of the fourth ring of preuroporphyrinogen followed by cyclization to produce uroporphyrinogen III. Uroporphyrinogen III decarboxylase (also called uro D or uroporphyrinogen decarboxylase) catalyzes the decarboxylation of all four acetic acid side chains of uroporphyrinogen III to methyl groups to yield coproporphyrinogen III. Coproporphyrinogen III oxidase (also called coproporphyrinogenase) catalyzes the oxidative decarboxylation of two propionate groups at positions 2 and 4 on the A and B rings of coproporphyrinogen III to vinyl groups yielding protoporphyrinogen IX. Protoporphyrinogen IX oxidase catalyzes a six electron oxidation of protoporphyrinogen IX to yield protoporphyrin IX. Ferrochelatase (also called ferrolyase, heme synthase, or protoheme ferrolyase) catalyzes the insertion of iron into the protoporphyrin to yield heme.

The conversion of an apoprotein into a hemoprotein depends on the availability of heme provided by the heme biosynthetic pathway. The apoprotein form of the hemoprotein combines with heme to produce the active hemoprotein which acquires a conformation which makes the hemoprotein more stable against proteolytic attack than the apoprotein. If the amount of heme produced by a microorganism is less relative to the amount of the apoprotein produced, the apoprotein will accumulate and undergo proteolytic degradation lowering the yield of the active hemoprotein.

In order to overcome this problem, Jensen showed that the addition of heme or a heme-containing material to a fermentation medium led to a significant increase in the yield of a peroxidase produced by *Aspergillus oryzae* (WO 93/19195). While heme supplementation of a fermentation medium results in a significant improvement in the yield of a hemoprotein, it is non-kosher, costly, and difficult to implement on a large scale.

Wu et al. (1991, *Journal of Bacteriology* 173:325–333) disclose a method for overexpression of an *E. coli* NADPH-sulfite reductase, a sirohemoprotein, comprising introducing a *Salmonella typhimurium* cysG gene, which encodes a uroporphyrinogen III methyltransferase required for the synthesis of siroheme, in a plasmid.

It is an object of the present invention to provide improved methods for increasing production of hemoproteins in filamentous fungal strains to yield commercially significant quantities.

SUMMARY OF THE INVENTION

The present invention relates to methods of producing a hemoprotein, comprising:

(a) introducing into a filamentous fungal cell, (i) one or more first control sequences capable of directing the expression of a heme biosynthetic enzyme encoded by a first nucleic acid sequence endogenous to the filamentous fungal cell, wherein the one or more of the first control sequences are operably linked to the first nucleic acid sequence; and/or (ii) one or more copies of one or more second nucleic acid sequences encoding a heme biosynthetic enzyme;

(b) cultivating the filamentous fungal cell in a nutrient medium suitable for production of the hemoprotein and the heme biosynthetic enzymes; and (c) recovering the hemoprotein from the nutrient medium of the filamentous fungal cell.

The present invention also relates to recombinant filamentous fungal cells comprising one or more first control sequences capable of directing the expression of a heme biosynthetic enzyme encoded by a first nucleic acid sequence endogenous to the filamentous fungal cell and/or one or more copies of one or more second nucleic acid sequences encoding heme biosynthetic enzymes.

BRIEF DESCRIPTION OF FIGURES

FIG. 3 shows the nucleotide and deduced amino acid sequences of an *Aspergillus oryzae* 5-aminolevulinic acid synthase gene (SEQ ID NOS: 1 and 2, respectively). Potentially important transcriptional sites, CCAAT box and TATA box are underlined. The two conserved putative HRM motifs are boxed; the glycine loop involved in pyridoxal phosphate co-factor binding is circled and the important lysine is indicated with an asterisk.

FIG. 4 shows the conserved heme regulatory motifs in various 5-aminolevulinic acid synthase genes. The pentapeptide motifs are boxed.

FIG. 5 shows the alignment of the deduced amino acid sequences for 5-aminolevulinic acid synthases from *Aspergillus oryzae, Aspergillus nidulans, Saccharomyces* cerevisiae and human erythroid (SEQ ID NOS: 2, 22, 23 and 24, respectively). Conserved amino acids are boxed.

Figure 6:
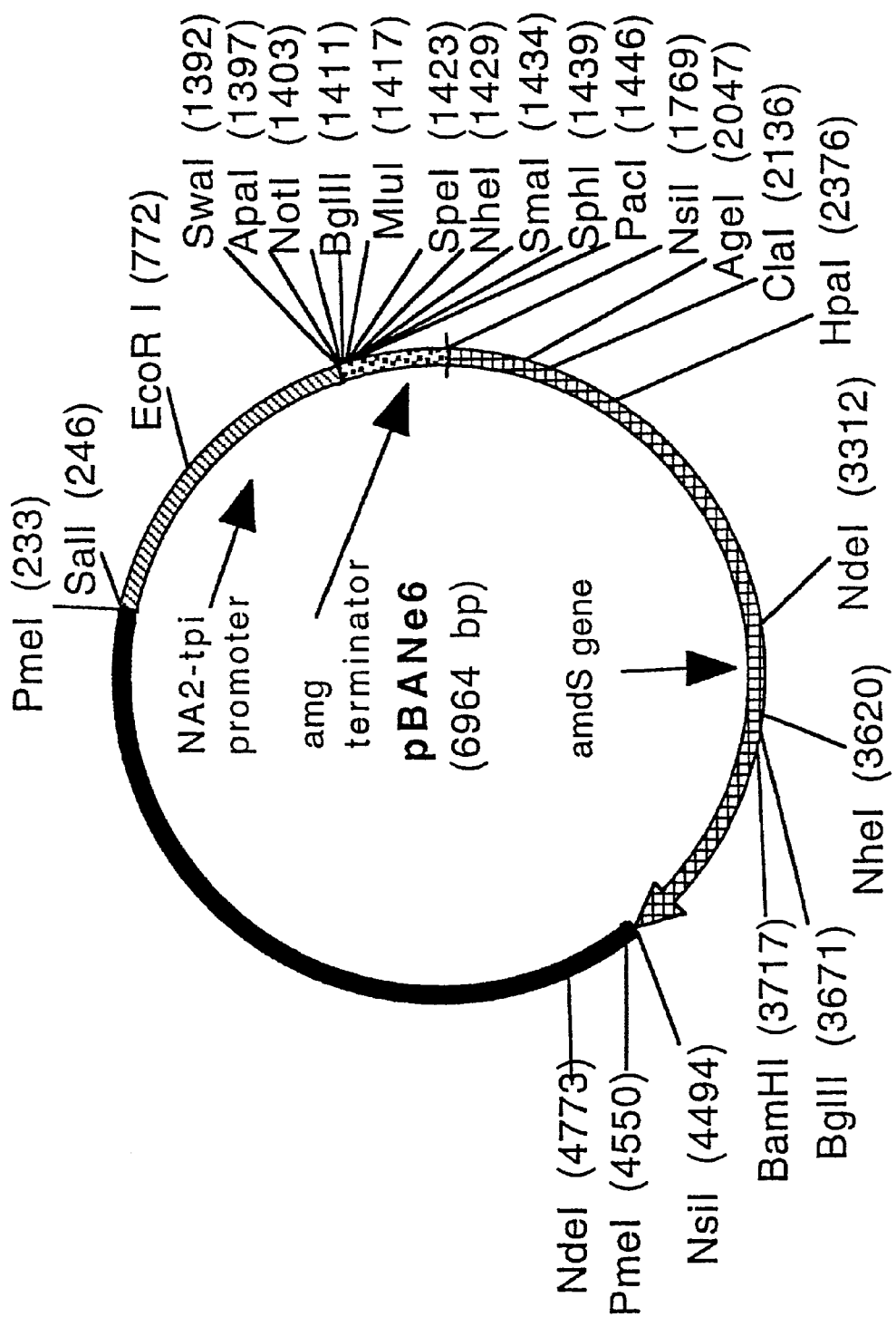

FIG. 6 shows a restriction map of plasmid pBANe6.

Figure 7:
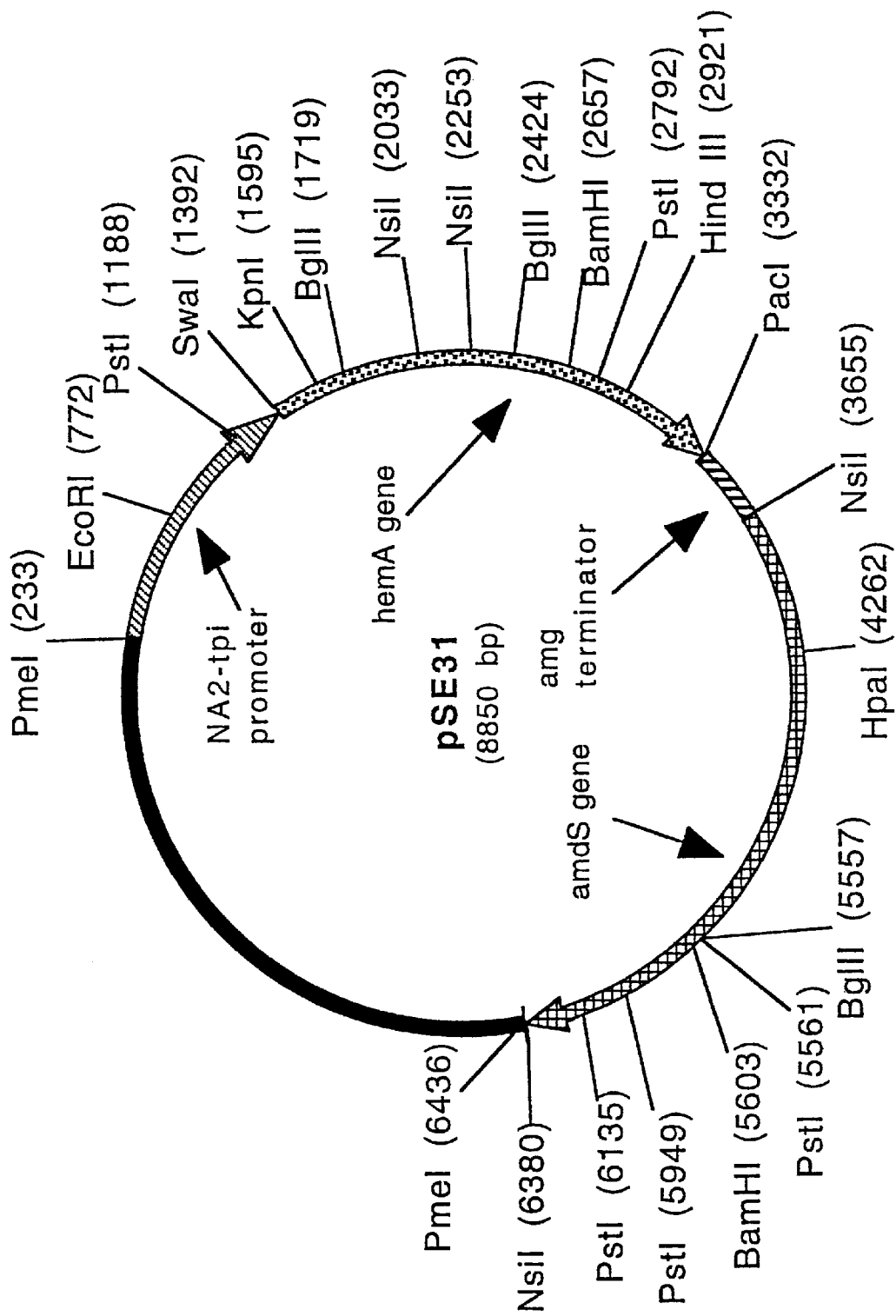

FIG. 7 shows a restriction map of plasmid pSE31.

Figure 8:
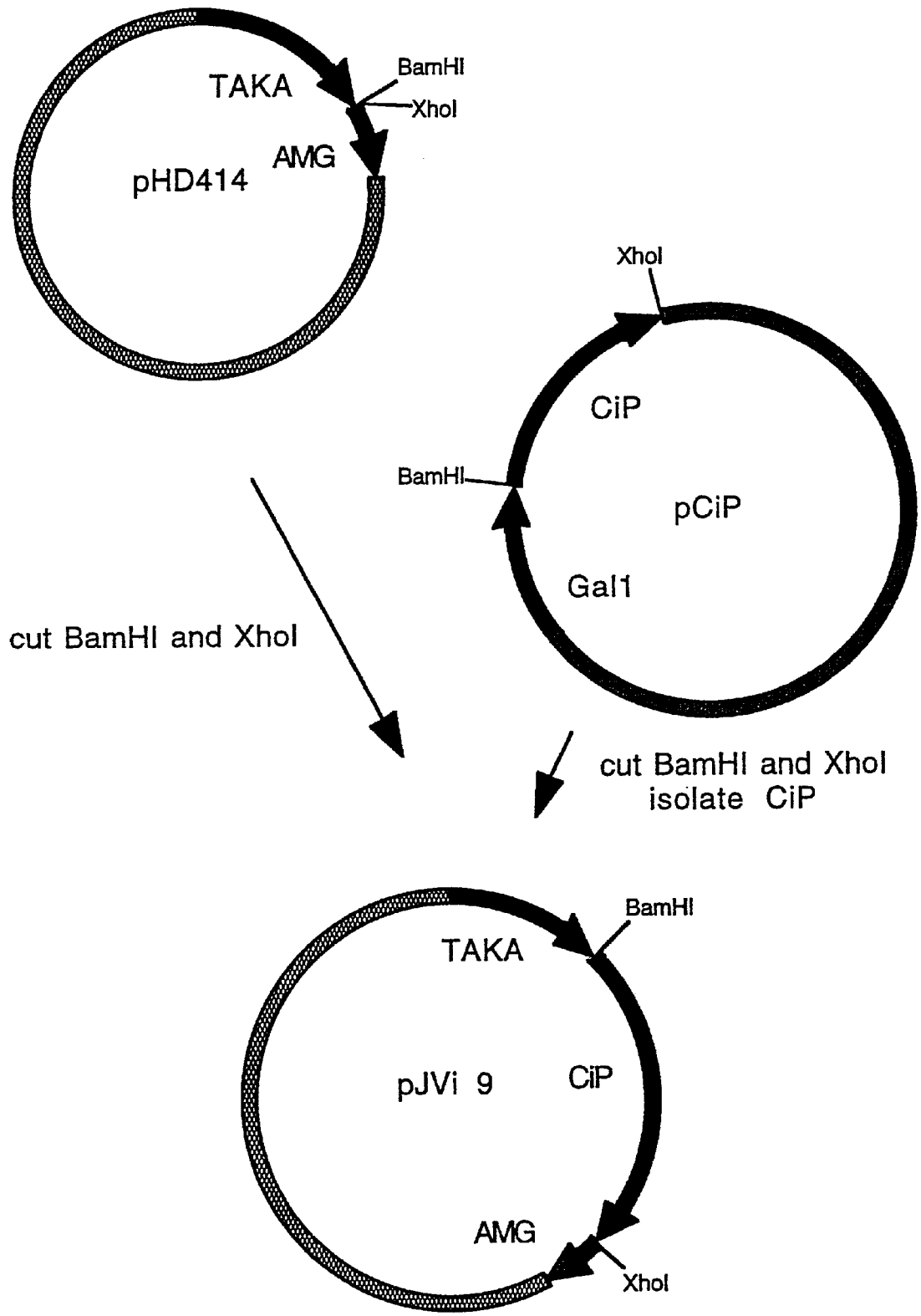

FIG. 8 shows the construction of plasmid pJVi9.

Figure 9:
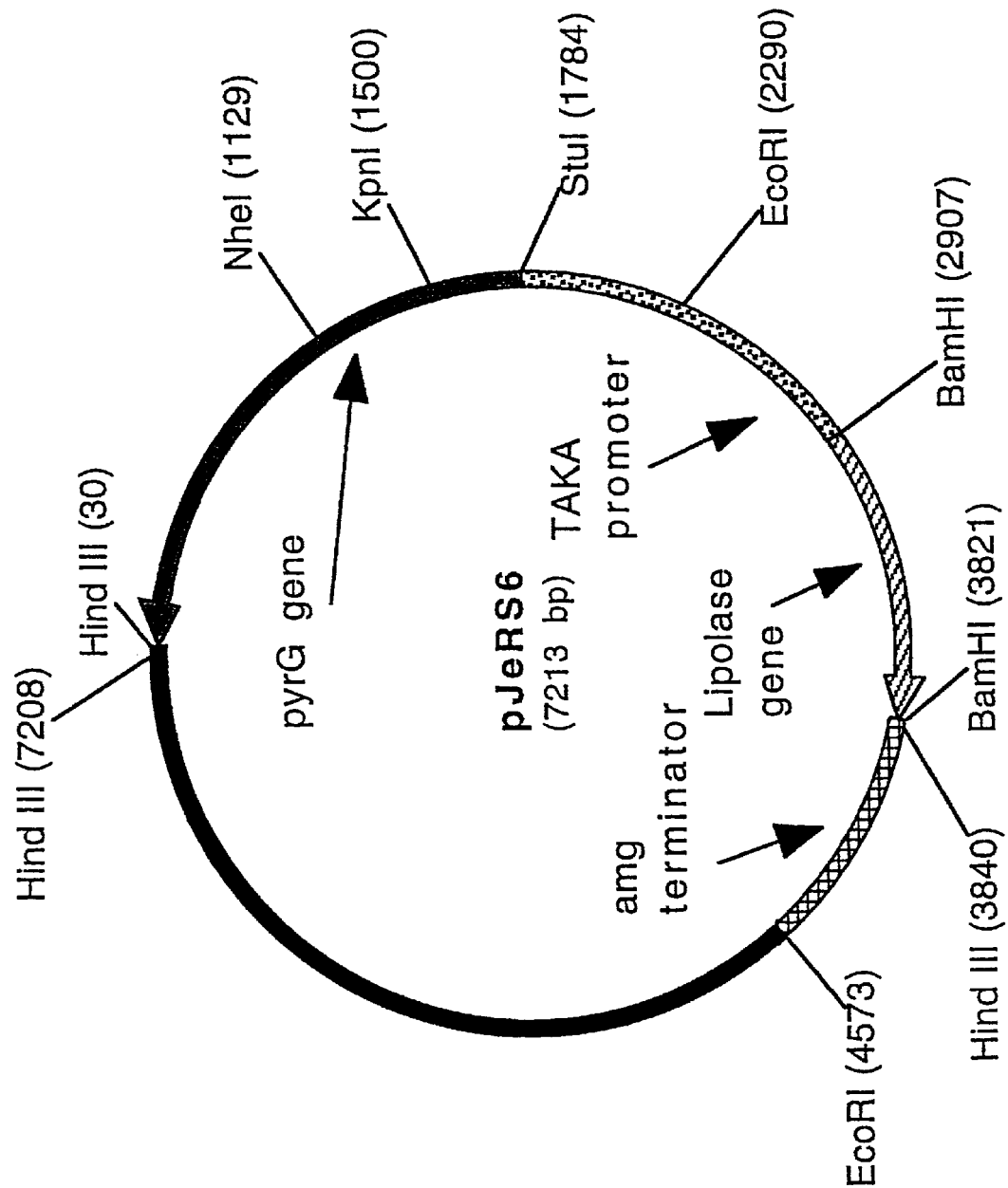

FIG. 9 shows a restriction map of plasmid pJeRS6.

Figure 10:
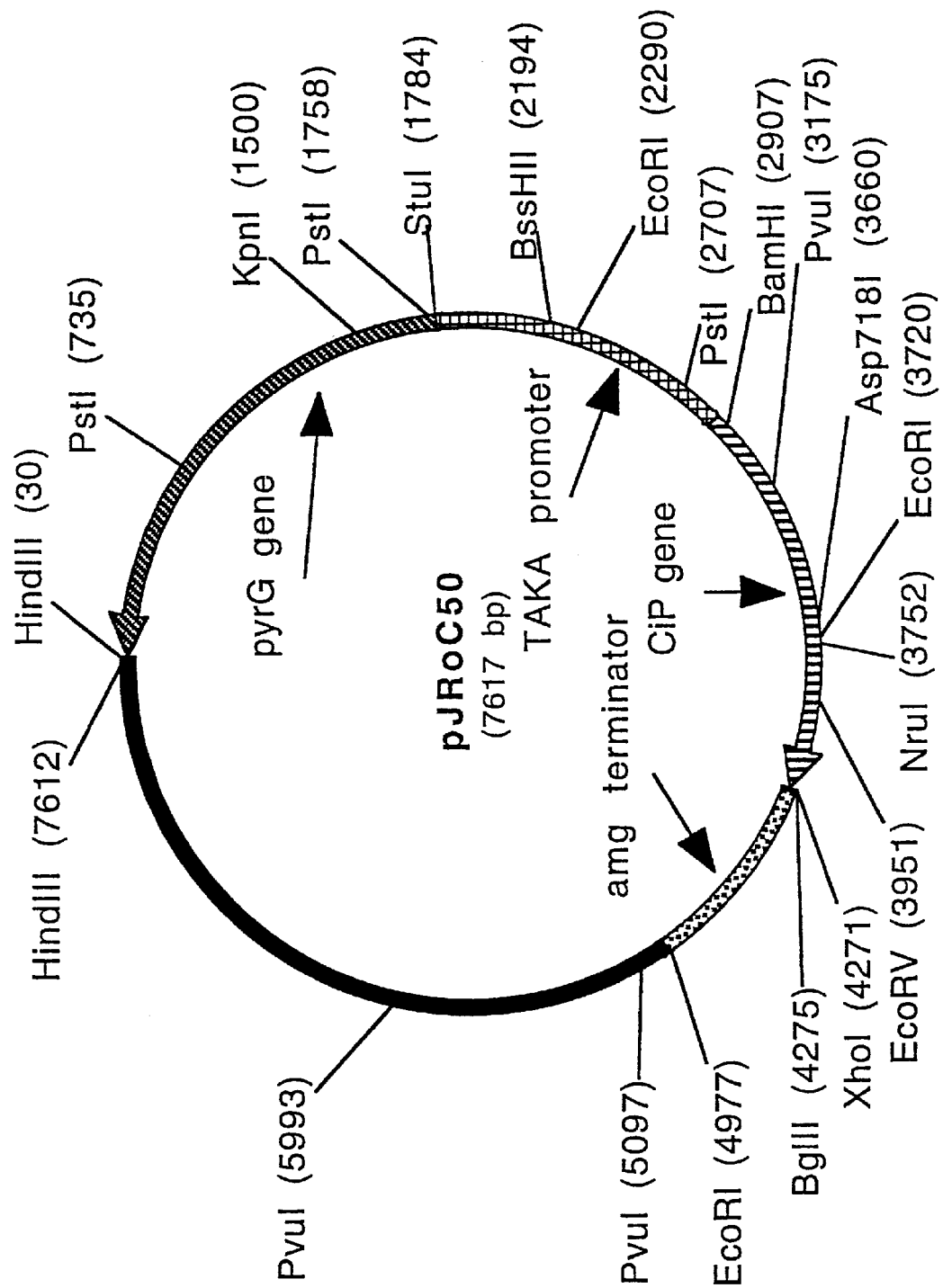

FIG. 10 shows a restriction map of plasmid pJRoC50.

Figure 11:
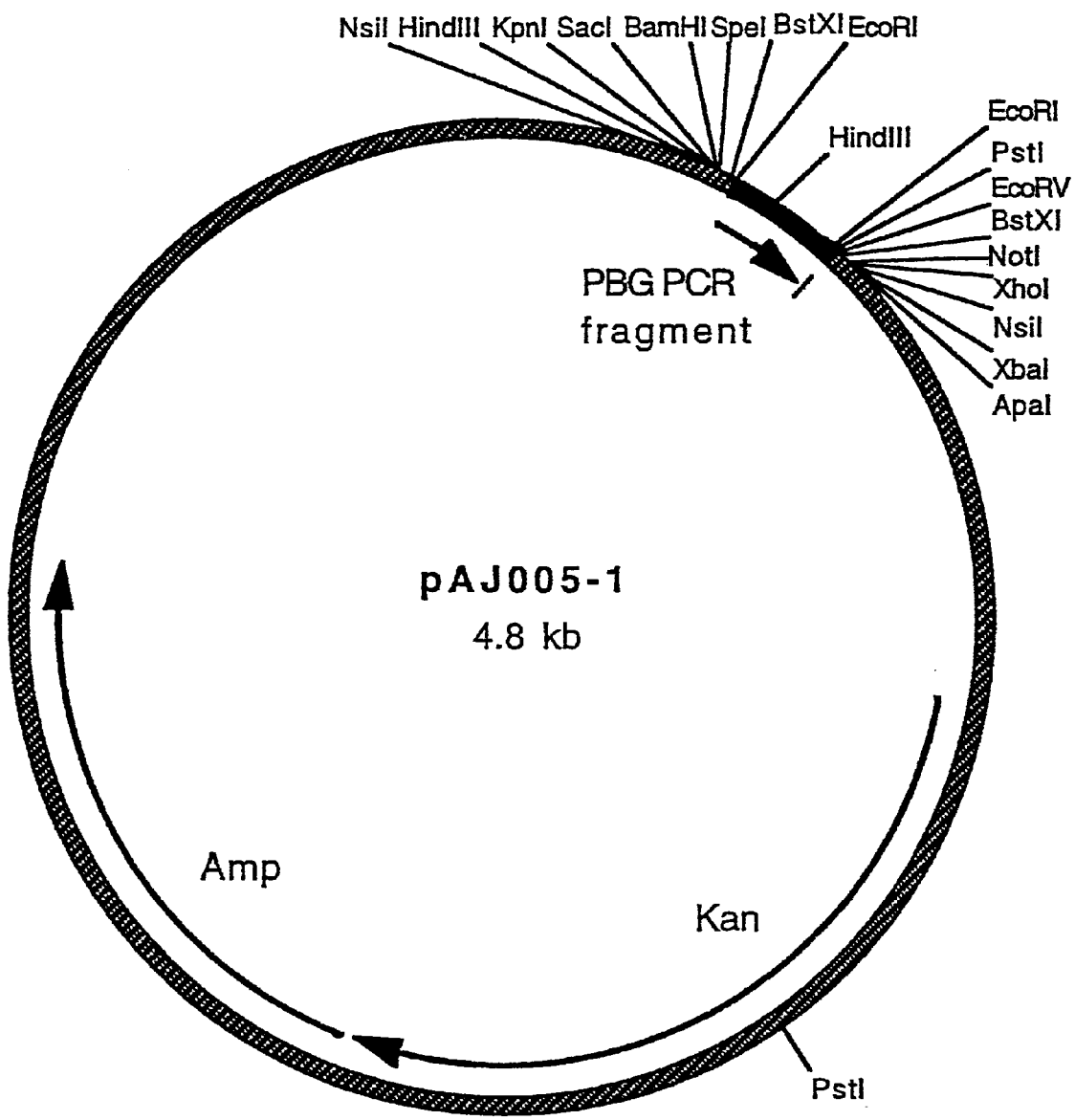

FIG. 11 shows a restriction map of plasmid pAJ005-1.

FIG. 12 shows the nucleotide and deduced amino acid sequence of the *Aspergillus oryzae* porphobilinogen synthase gene (SEQ ID NOS: 3 and 4, respectively). CAAT boxes are underlined and TATA boxes are boxed. The putative intron is identified with a dotted underline and the putative zinc finger domain is identified with a dashed underline. The library probe is identified with a dark solid underline and the active lysine is circled.

FIG. 13 shows the alignment of the deduced amino acid sequences for porphobilinogen synthases from *B. subtilis, E. coli*, human, pea, rat, spinach, yeast and *Aspergillus oryzae* (SEQ ID NOS: 25, 26, 27, 28, 29, 30, 31 and 4, respectively).

Figure 14:
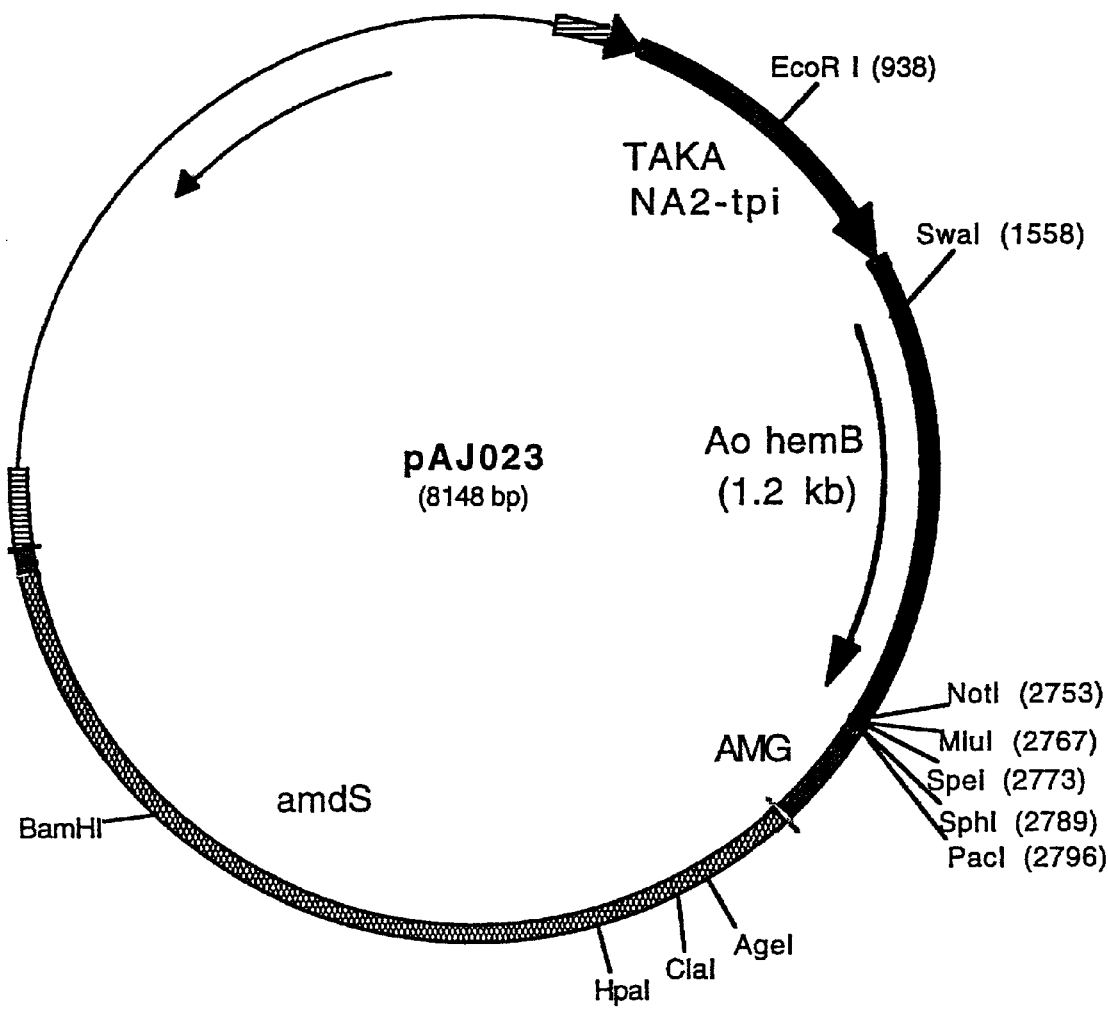

FIG. 14 shows a restriction map of pAJ023.

Figure 15:
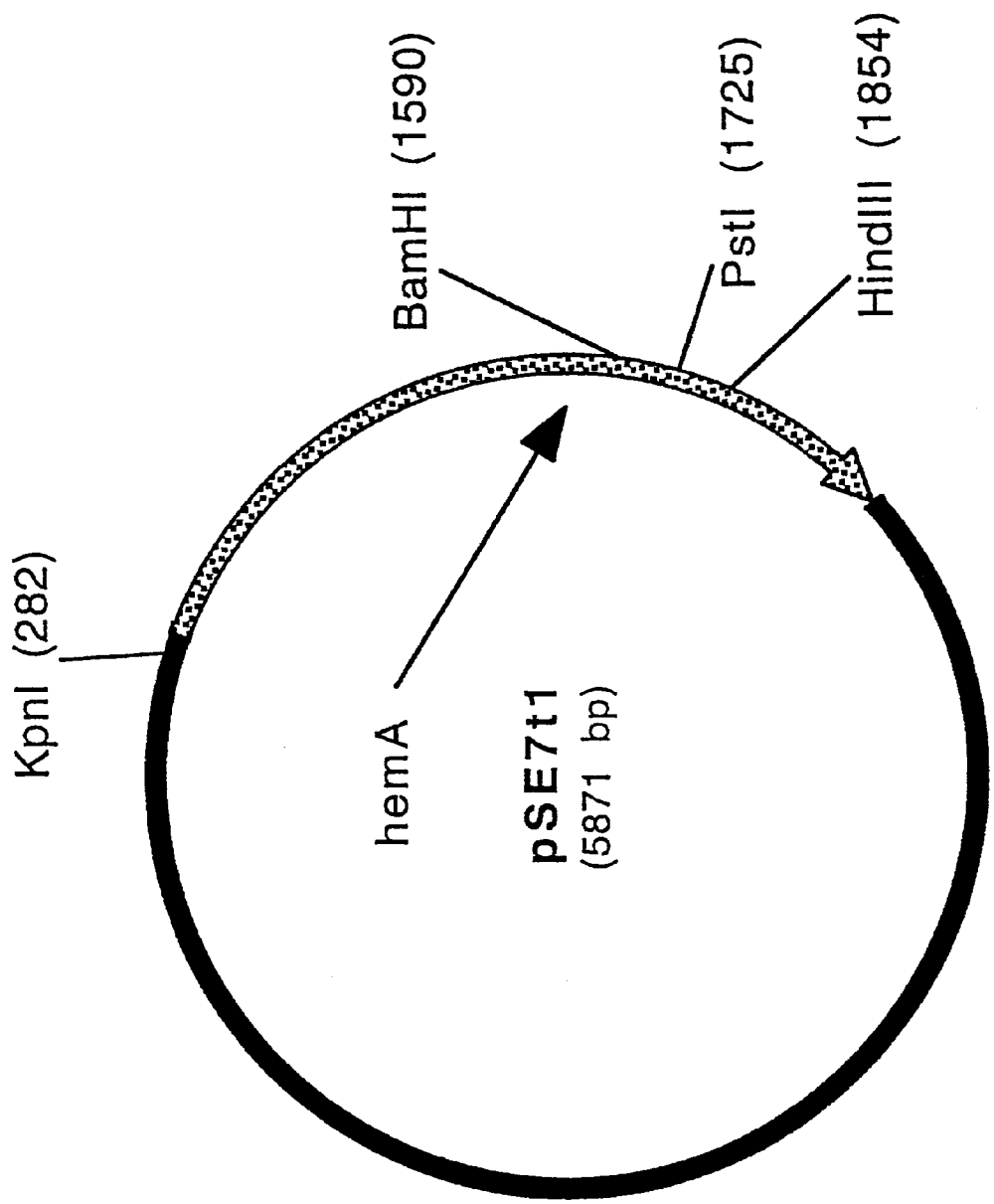

FIG. 15 shows a restriction map of plasmid pSE7t1.

Figure 16:
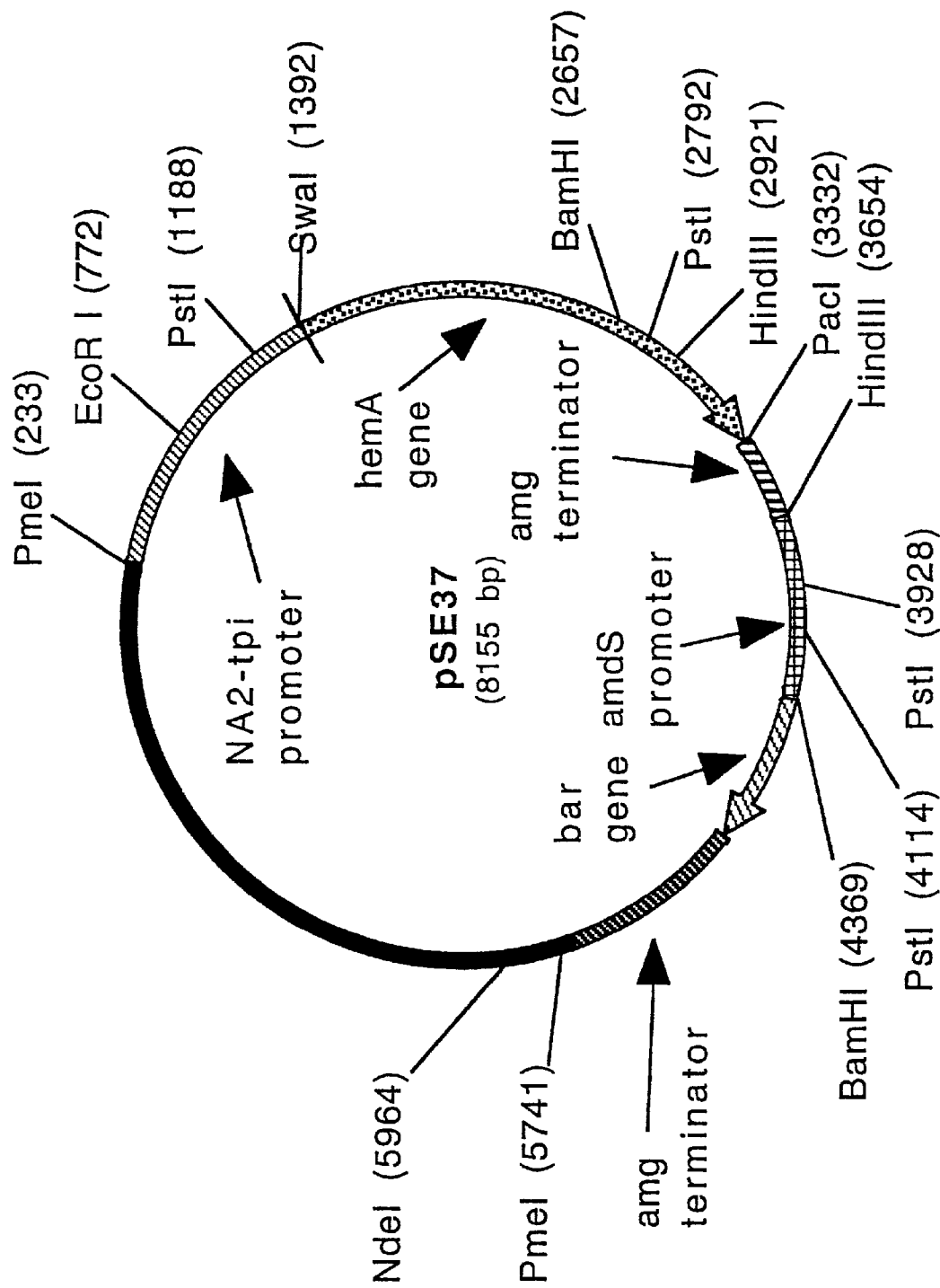

FIG. 16 shows a restriction map of plasmid pSE37.

Figure 17:
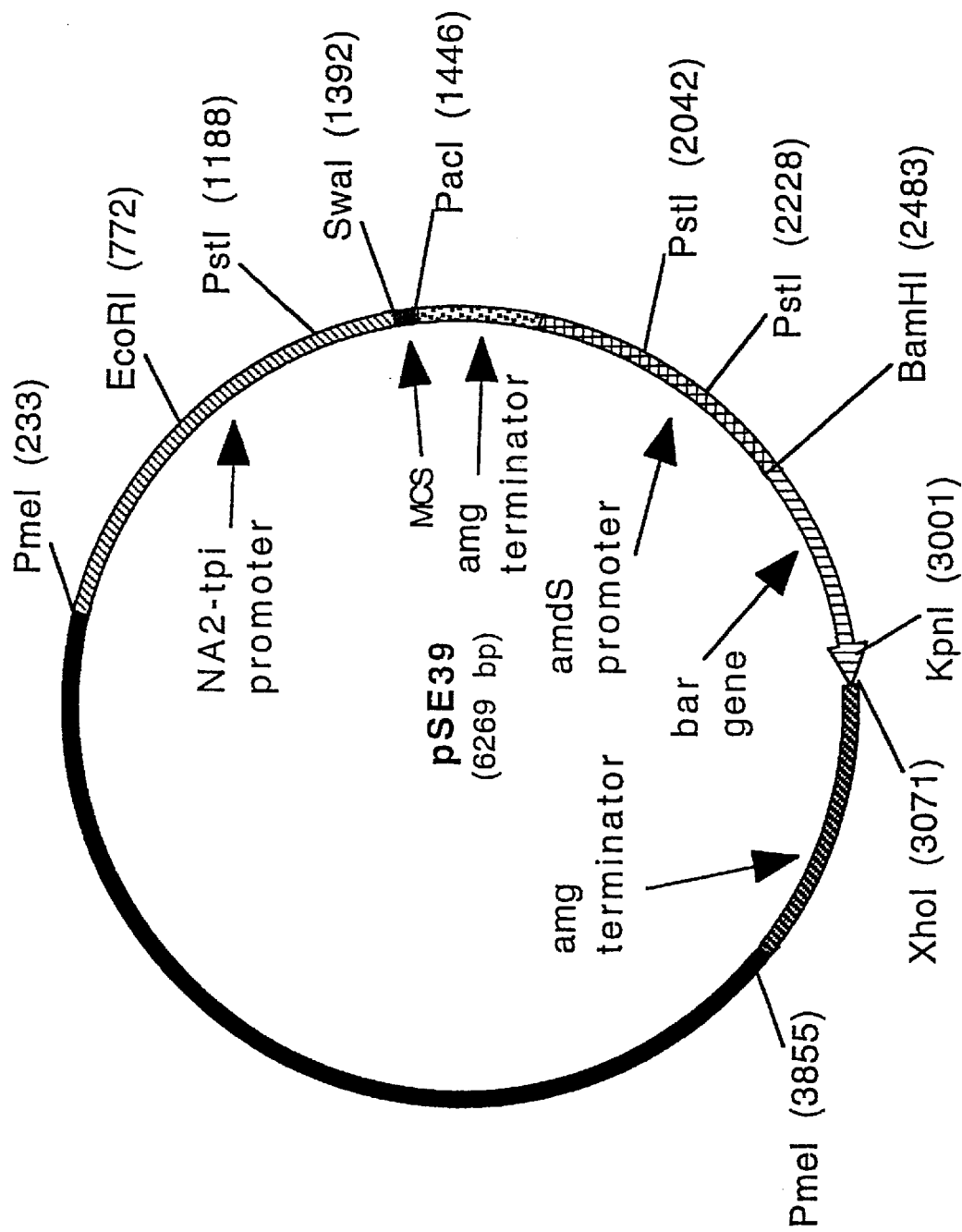

FIG. 17 shows a restriction map of plasmid pSE39.

Figure 18:
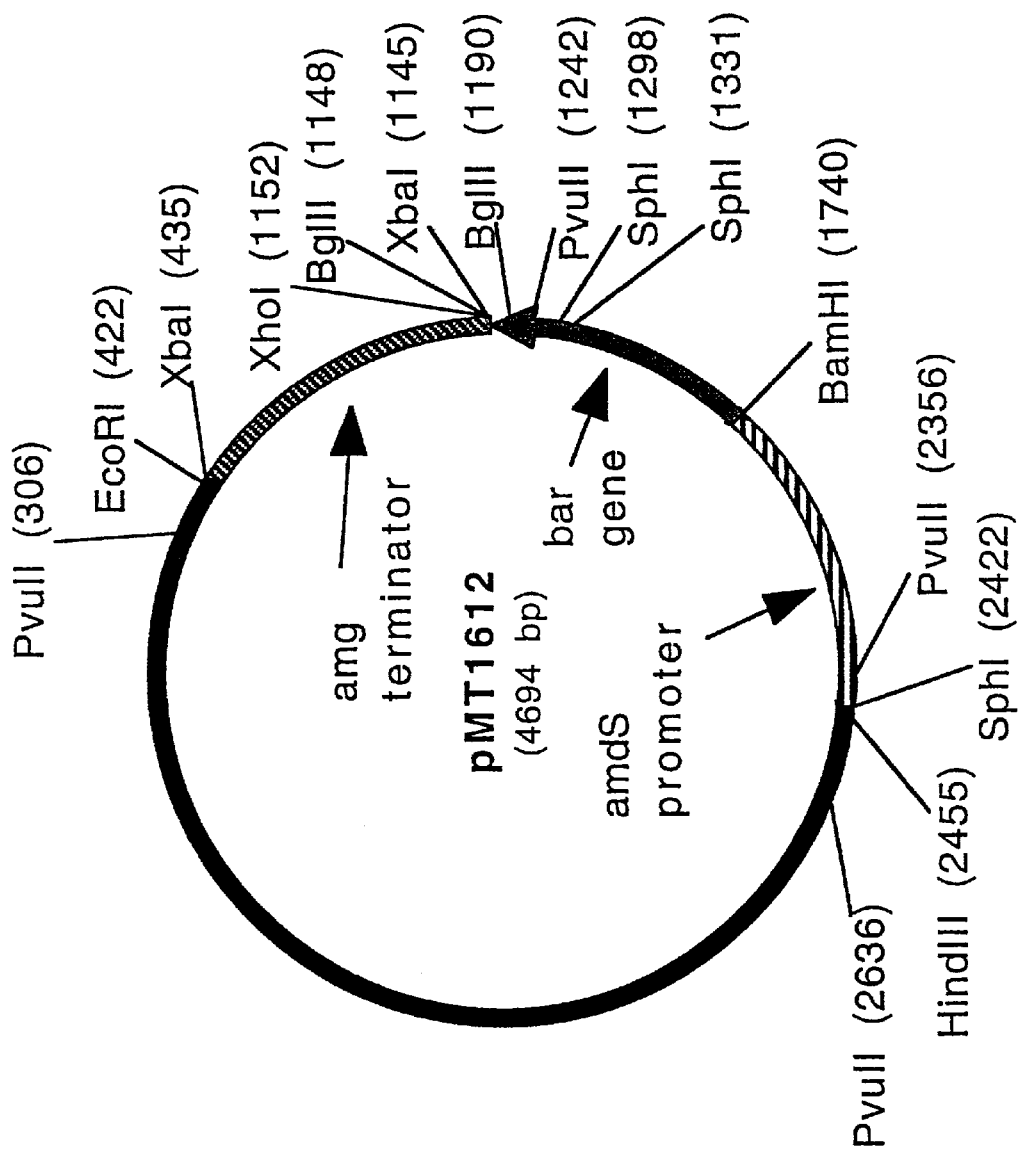

FIG. 18 shows a restriction map of plasmid pMT1612.

Figure 19:
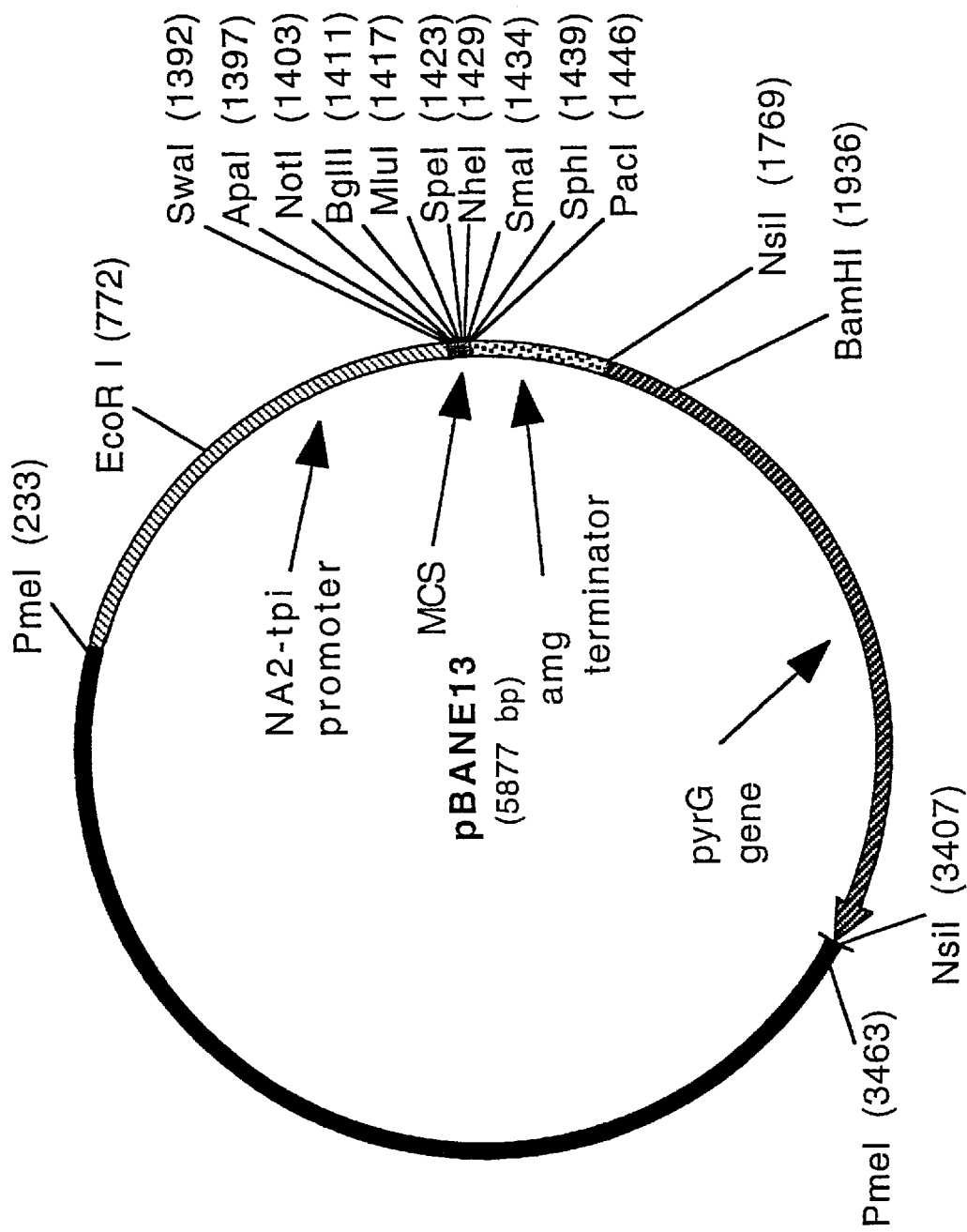

FIG. 19 shows a restriction map of plasmid pBANe13.

Figure 20:
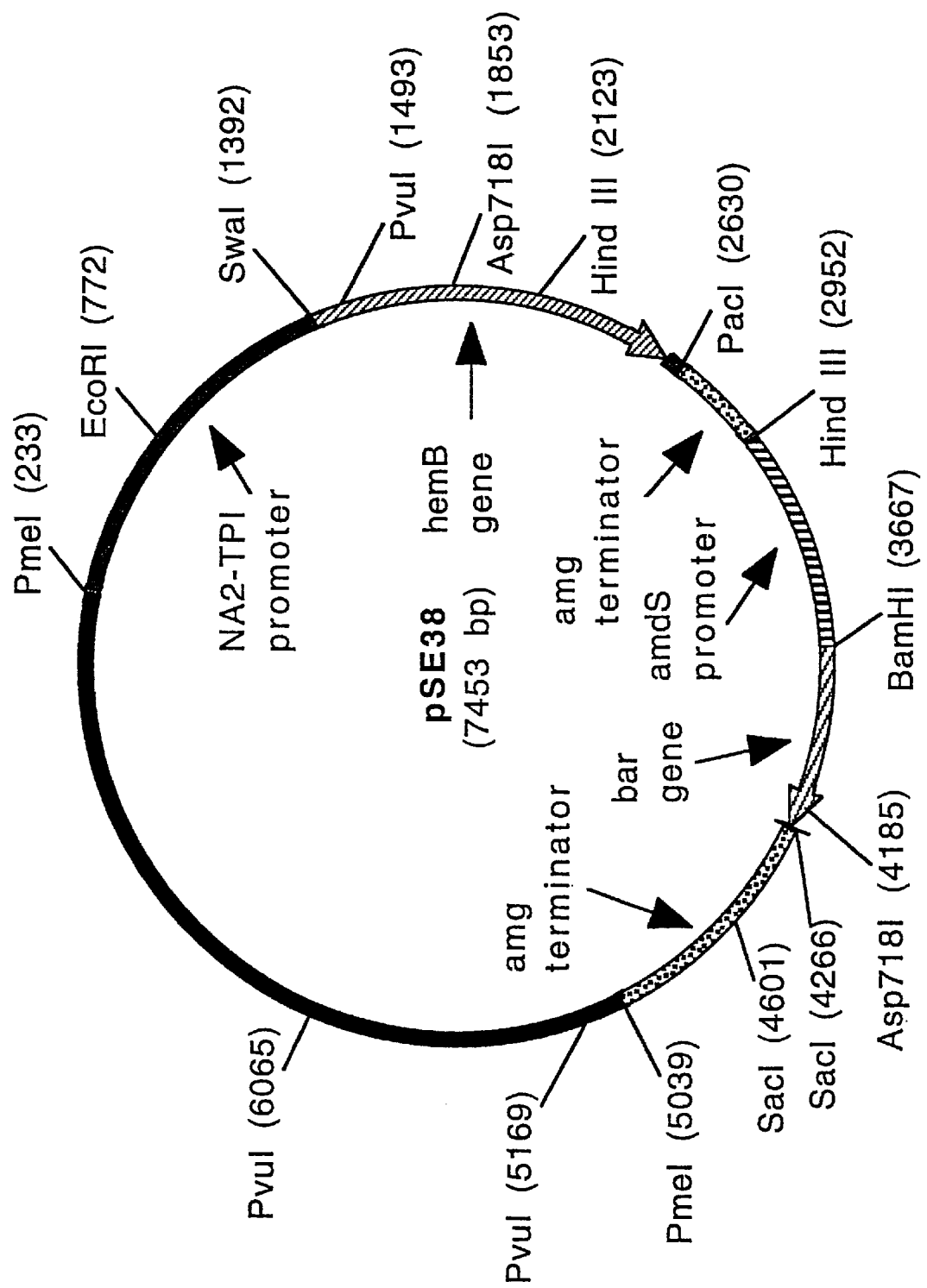

FIG. 20 shows a restriction map of plasmid pSE38.

Figure 21:
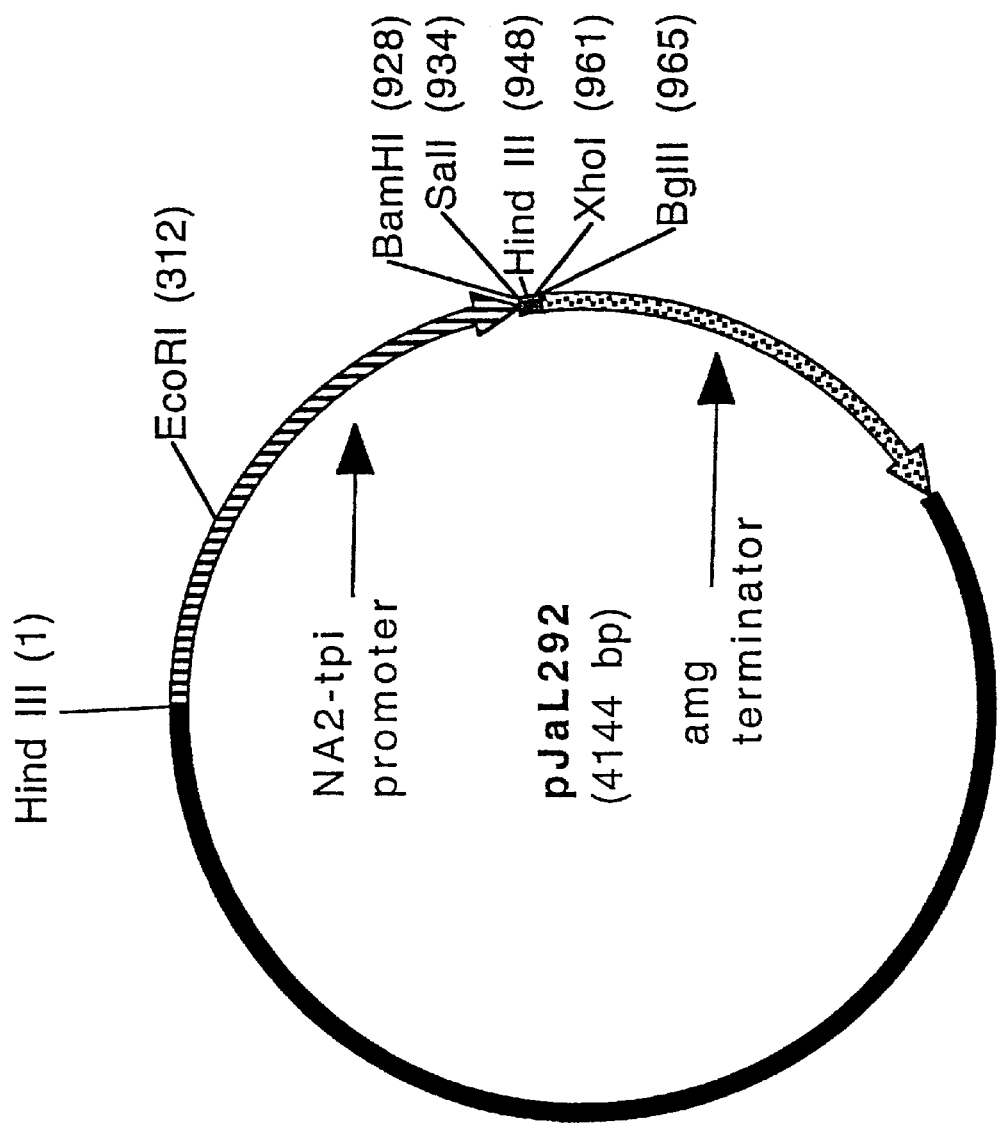

FIG. 21 shows a restriction map of plasmid pJaL292.

Figure 22:
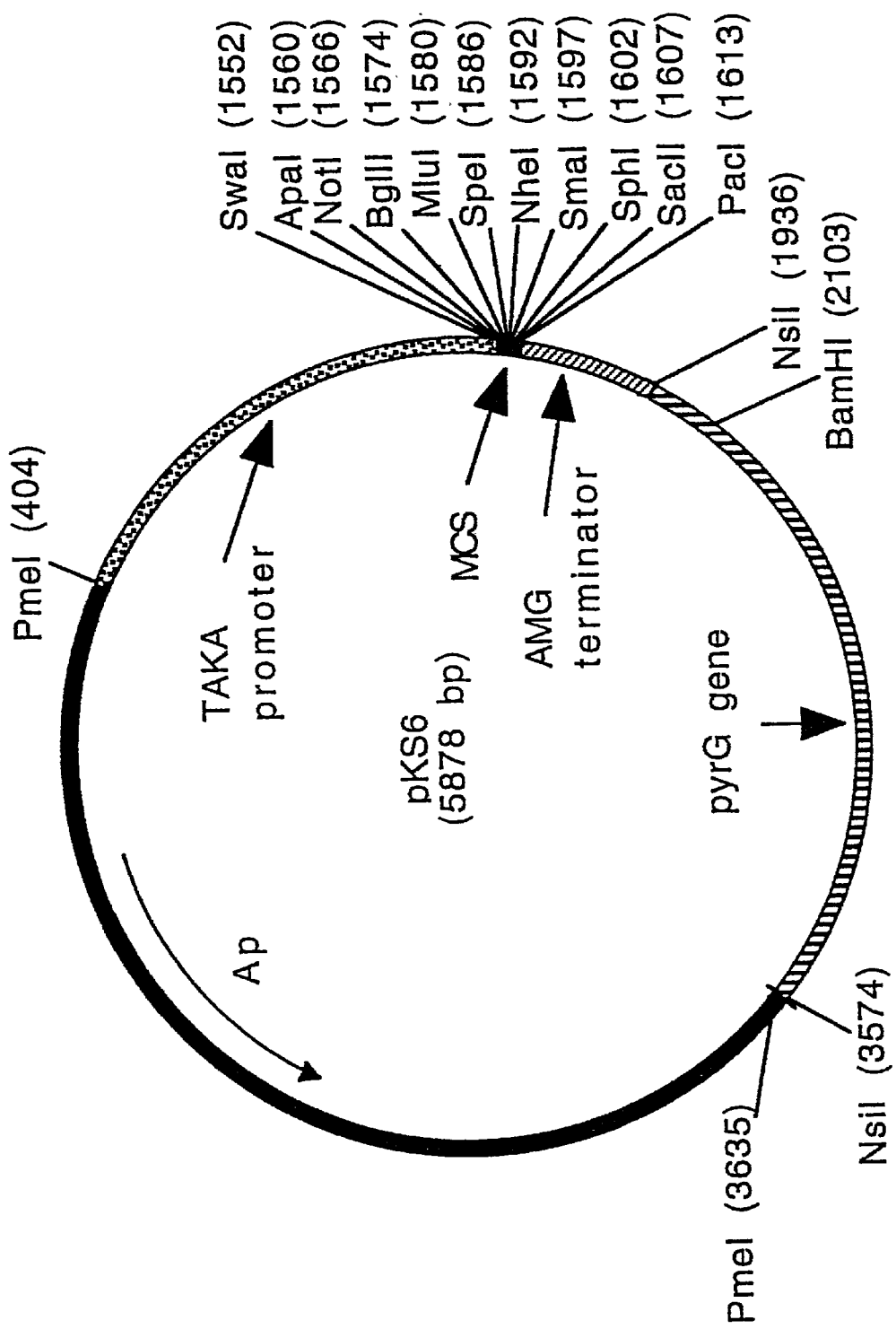

FIG. 22 shows a restriction map of plasmid pKS6.

Figure 23:
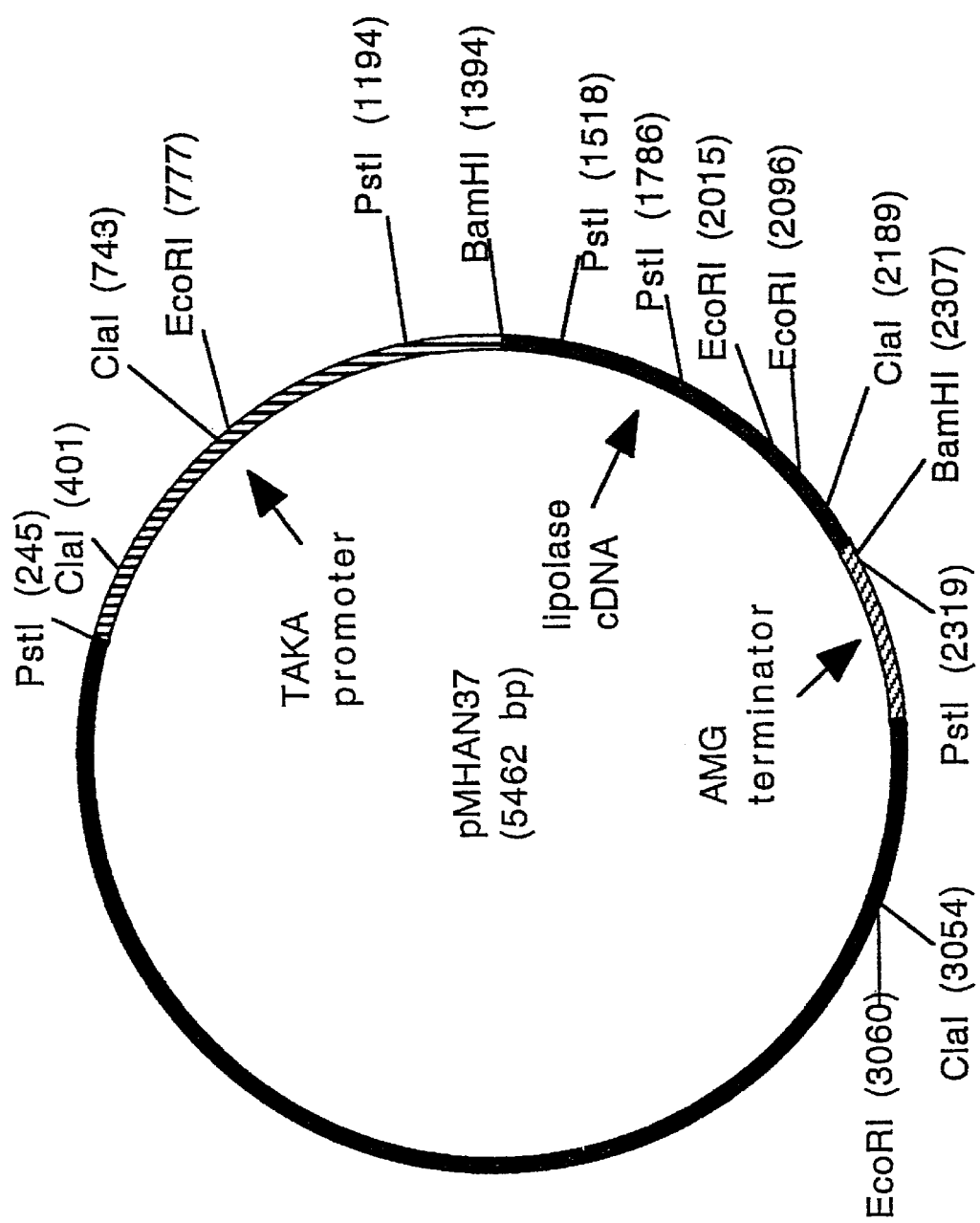

FIG. 23 shows a restriction map of plasmid pMHan37.

Figure 24:
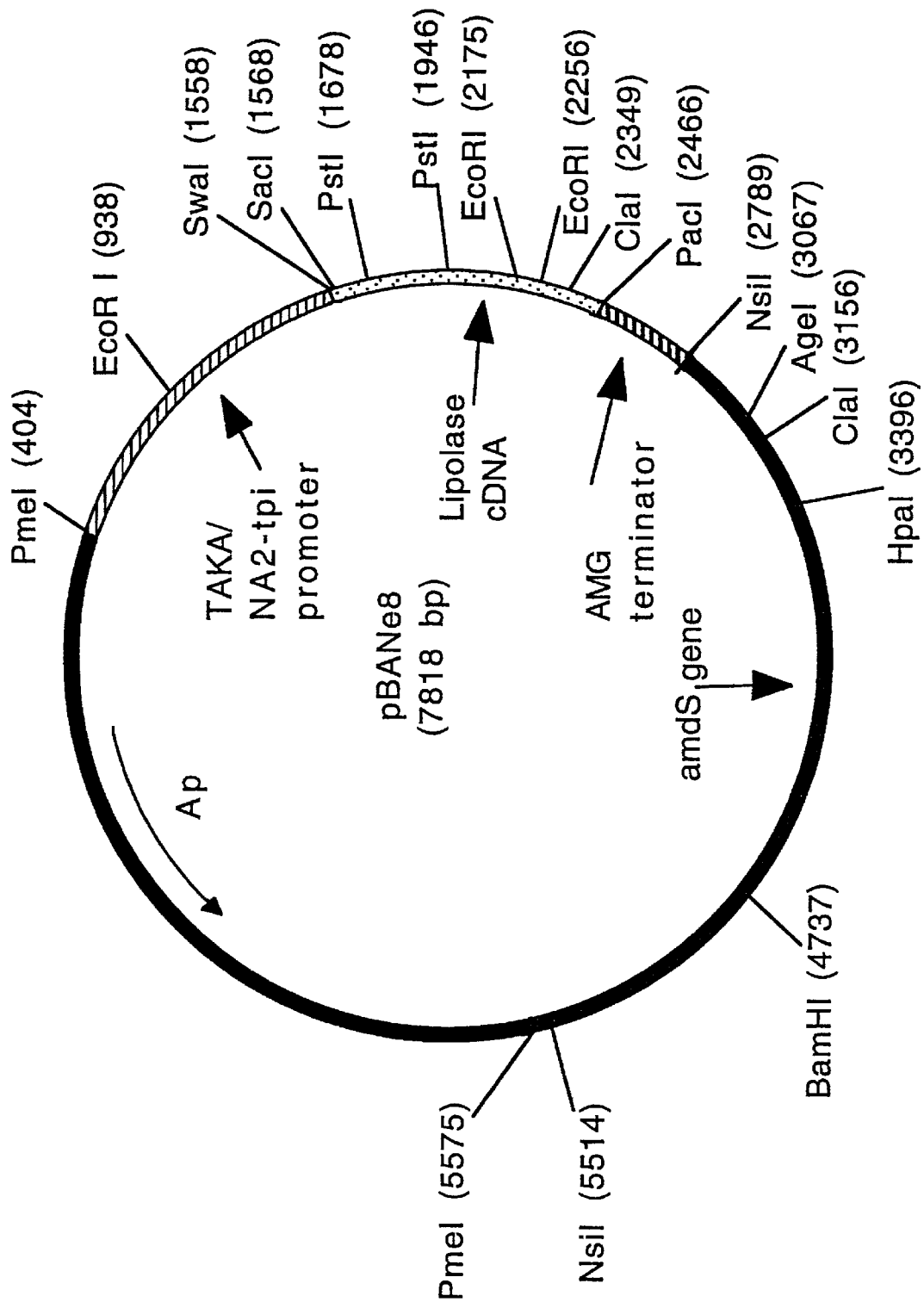

FIG. 24 shows a restriction map of plasmid pBANe8.

DETAILED DESCRIPTION OF THE INVENTION

The present invention relates to methods of producing a hemoprotein, comprising:

(a) introducing into a filamentous fungal cell, (i) one or more first control sequences capable of directing the expression of a heme biosynthetic enzyme encoded by a first nucleic acid sequence endogenous to the filamentous fungal cell, wherein the one or more of the first control sequences are operably linked to the first nucleic acid sequence; and/or (ii) one or more copies of one or more second nucleic acid sequences encoding a heme biosynthetic enzyme;

(b) cultivating the filamentous fungal cell in a nutrient medium suitable for production of the hemoprotein and the heme biosynthetic enzymes; and (c) recovering the hemoprotein from the nutrient medium of the filamentous fungal cell. "Hemoprotein" is defined herein as any member of a group of proteins containing heme as a prosthetic group. The hemoprotein may be a globin, a cytochrome, an oxidoreductase, or any other protein containing a heme as a prosthetic group. Heme-containing globins include hemoglobin and myoglobin. Heme-containing cytochromes include cytochrome P450, cytochrome b, cytochrome $c_1$, and cytochrome c. Heme-containing oxidoreductases include, but are not limited to, a catalase, an oxidase, an oxygenase, a haloperoxidase, and a peroxidase. In a preferred embodiment, the oxidoreductase is a catalase. In another preferred embodiment, the oxidoreductase is an oxidase. In another preferred embodiment, the oxidoreductase is an oxygenase. In another preferred embodiment, the oxidoreductase is a haloperoxidase. In another preferred embodiment, the oxidoreductase is a peroxidase. In a more preferred embodiment, the peroxidase is obtained from a Coprinus strain, an Arthromyces strain, or a Phanerochaete strain. In an even more preferred embodiment, the peroxidase is obtained from a *Coprinus cinereus* strain, e.g., *Coprinus cinereus* IFO 8371, a *Coprinus macrorhizus* strain, or an *Arthromyces ramosus* strain. In another more preferred embodiment, the catalase is obtained from a Scytalidium strain, an Aspergillus strain, or a Humicola strain. In another even more preferred embodiment, the catalase is obtained from a *Scytalidium thermophilum* strain, e.g., *Scytalidium thermophilum* CBS 117.65, an *Aspergillus niger* strain, or a *Humicola insolens* strain.

The hemoprotein may be native or foreign to the filamentous fungal cell.

The control sequences and/or the nucleic acid sequences can be introduced into the filamentous fungal cell by methods well known in the art. For example, the sequences may be introduced and integrated into the host genome by homologous or non-homologous recombination where one or more copies of the sequences are integrated into a single target sequence and/or multiple target sequences. Alternatively, the sequences may be introduced and maintained as a non-integrated expression vector, e.g., a self-replicating extrachromosomal plasmid. A standard procedure in the art for introducing a nucleic acid sequence into a filamentous fungal cell involves protoplast formation, transformation of the protoplasts, and regeneration of the cell wall of the transformed protoplasts in a manner known per se (see EP 238 023 and Malardier et al., 1989, *Gene* 78:147–156). The cell is preferably transformed with an integrative vector comprising a nucleic acid construct which contained the control sequences and/or nucleic acid sequences encoding the heme biosynthetic enzymes where the construct is conveniently integrated into the host genome of the filamentous fungal cell, preferably the chromosome (s). The term "nucleic acid construct" is defined herein to mean a nucleic acid molecule, either single- or double-stranded, which is isolated from a naturally occurring gene or which has been modified to contain segments of nucleic acids which are combined and juxtaposed in a manner which would not otherwise exist in nature.

The filamentous fungal cells of the present invention are cultivated in a nutrient medium suitable for production of the hemoprotein and the heme biosynthetic enzymes using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the hemoprotein to be expressed and/or isolated. The cultivation takes place in a suitable nutrient medium comprising carbon and nitrogen sources and inorganic salts, using procedures known in the art (see, e.g., Bennett, J. W. and LaSure, L., eds., *More Gene Manipulations in Fungi*, Academic Press, CA, 1991). Suitable media are available from commercial suppliers or may be prepared using published compositions (e.g., in catalogues of the American Type Culture Collection). If the hemoprotein is secreted into the nutrient medium, the hemoprotein can be recovered directly from the medium. The signal peptide coding region for secretion of the hemoprotein in the filamentous fungal host cell may be obtained, e.g., from *Aspergillus oryzae* TAKA amylase gene, *Aspergillus niger* neutral amylase gene, the *Rhizomucor miehei* aspartic proteinase gene, the *Humicola lanuginosa* cellulase gene, or the *Rhizomucor miehei* lipase gene. If the hemoprotein is not secreted, it is recovered from cell lysates.

The resulting hemoprotein may be recovered by methods known in the art. For example, the hemoprotein may be recovered from the nutrient medium by conventional procedures including, but not limited to, centrifugation, filtration, extraction, spray-drying, evaporation, or precipitation. The recovered protein may then be further purified by a variety of chromatographic procedures, e.g., ion exchange chromatography, gel filtration chromatography, affinity chromatography, or the like.

In one aspect of the present invention, a hemoprotein is produced in higher amounts in a filamentous fungal cell by introducing into the filamentous fungal cell one or more first control sequences capable of directing the expression of a heme biosynthetic enzyme encoded by the first nucleic acid sequence endogenous to the filamentous fungal cell, wherein the one or more of the first control sequences are operably linked to the first nucleic acid sequence.

The first nucleic acid sequence may be any filamentous fungal nucleic acid sequence encoding a heme biosynthetic enzyme selected from the group consisting of a 5-aminolevulinic acid synthase, a porphobilinogen synthase, a porphobilinogen deaminase, an uroporphyrinogen synthase, an uroporphyrinogen decarboxylase, a coproporphyrinogen oxidase, a protoporphyrinogen oxidase, and a ferrochelatase, wherein the first nucleic acid sequence is endogenous to the filamentous fungal host cell. The term "endogenous" is defined herein as originating from the filamentous fungal host cell.

The term "control sequences" is meant herein to include all components which are necessary or advantageous for expression of the coding sequence of the first nucleic acid sequence. The control sequences may be native to the first nucleic acid sequence encoding the heme biosynthetic enzyme, may be obtained from other sources, or may be a combination of native and foreign control sequences. The foreign control sequences may simply replace or be added to the natural control sequences in order to obtain enhanced production of the desired heme biosynthetic enzyme relative to the natural control sequence normally associated with the coding sequence. Such control sequences include, but are not limited to, a leader, a polyadenylation sequence, a propeptide sequence, a promoter, a signal sequence, and a transcription terminator. For expression under the direction of control sequences, the first nucleic acid sequence to be used according to the present invention is operably linked to the control sequences in such a way that expression of the coding sequence of the first nucleic acid sequence is achieved under conditions compatible with the control sequences. The term "coding sequence" as defined herein is a sequence which is transcribed into mRNA and translated into a heme biosynthetic enzyme when placed under the control of the above mentioned control sequences. The boundaries of the coding sequence are determined by a translation start codon at the 5'-terminus and a translation stop codon at the 3'-terminus. A coding sequence can include, but is not limited to, DNA, cDNA, and recombinant nucleic acid sequences.

The first control sequence may be an appropriate promoter sequence, a nucleic acid sequence which is recognized by the filamentous fungal host for expression of the first nucleic acid sequence. The promoter sequence contains transcription and translation control sequences which mediate the expression of the heme biosynthetic enzyme. The promoter may be any promoter sequence which shows transcriptional activity in the host cell of choice and may be obtained from genes either homologous or heterologous to the host cell. Examples of suitable promoters for directing the transcription of the first nucleic acid sequence in a filamentous fungal host are promoters obtained from the genes encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and hybrids thereof. Particularly preferred promoters are the TAKA amylase, NA2-tpi (a hybrid of the promoters from the genes encoding *Aspergillus niger* neutral α-amylase and *Aspergillus oryzae* triose phosphate isomerase), and glaA promoters.

The first control sequence may also be a suitable transcription terminator sequence, a sequence recognized by the filamentous fungal host to terminate transcription. The terminator sequence is operably linked to the 3' terminus of the first nucleic acid sequence encoding the heme biosynthetic enzyme. The terminator sequence may be native to the first nucleic acid sequence encoding the heme biosynthetic enzyme or may be obtained from other sources, i.e., a foreign terminator sequence. Any terminator which is functional in the filamentous fungal host cell of choice is likely to be useful in the present invention, but particularly preferred terminators are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

The first control sequence may also be a suitable leader sequence, a nontranslated region of a MRNA which is important for translation by the filamentous fungal host. The leader sequence is operably linked to the 5' terminus of the first nucleic acid sequence encoding the heme biosynthetic enzyme. The leader sequence may be native to the first nucleic acid sequence or may be obtained from other sources, i.e., a foreign leader sequence. Any leader sequence which is functional in the filamentous fungal host cell of choice is likely to be useful in the present invention, but particularly preferred leaders are obtained from the genes encoding *Aspergillus oryzae* TAKA amylase and Aspergillus oryzae triose phosphate isomerase.

The first control sequence may also be a polyadenylation sequence, a sequence which is operably linked to the 3' terminus of the first nucleic acid sequence and which, when transcribed, is recognized by the filamentous fungal host to add polyadenosine residues to transcribed mRNA. The polyadenylation sequence may be native to the first nucleic acid sequence encoding the heme biosynthetic enzyme or may be obtained from other sources, i.e., a foreign polyadenylation sequence. Any polyadenylation sequence which is functional in the fungal host of choice is likely to be useful in the present invention, but particularly preferred polyadenylation sequences are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

The first control sequence may also be a signal peptide coding region, which codes for an amino acid sequence linked to the amino terminus of the heme biosynthetic enzyme, permitting the localization of the heme biosynthetic enzyme to a particular cellular compartment. The signal peptide coding region may be native to the first nucleic acid sequence encoding the heme biosynthetic enzyme or may be obtained from foreign sources. The 5' end of the coding sequence of the first nucleic acid sequence may inherently contain a signal peptide coding region naturally linked in translation reading frame with the segment of the coding region which encodes the localized heme biosynthetic enzyme. Alternatively, the 5' end of the coding sequence may contain nucleic acids encoding a signal peptide coding region which is foreign to that portion of the coding sequence which encodes the localized heme biosynthetic enzyme. The signal peptide coding region may be obtained from a *Neurospora crassa* ATPase gene (Viebrock et al., 1982, *EMBO Journal* 1:565–571) or from a *Saccharomyces cerevisiae* cytochrome c peroxidase gene (Kaput et al., 1982, *Journal of Biological Chemistry* 257:15054–15058). However, any signal peptide coding region capable of permitting localization of the heme biosynthetic enzyme in a filamentous fungal host of choice may be used in the present invention.

The first control sequence may also be a propeptide coding region which codes for an amino acid sequence positioned at the amino terminus of a mature biochemically active polypeptide. The resultant polypeptide is known as a proenzyme or a propolypeptide (or a zymogen in some cases). Proenzymes are generally inactive and can be converted to mature active polypeptides by catalytic or autocatalytic cleavage of the propeptide from the proenzyme. A biochemically active polypeptide is defined herein as a heme biosynthetic enzyme which is produced in active form which performs the biochemical activity of its natural counterpart. The propeptide sequence may be native to the first nucleic acid sequence encoding the heme biosynthetic enzyme or may be obtained from other sources, i.e., a foreign propeptide sequence. The nucleic acid sequence encoding a propeptide may be obtained from the genes encoding *Saccharomyces cerevisiae* alpha-factor and *Myceliophthora thermophilum* laccase.

In another aspect of the present invention, a hemoprotein is produced in higher amounts in a filamentous fungal cell by introducing into the filamentous fungal cell one or more copies of one or more second nucleic acid sequences encoding a heme biosynthetic enzyme. The second nucleic acid sequence may be any nucleic acid sequence encoding a heme biosynthetic enzyme selected from the group consisting of a 5-aminolevulinic acid synthase, a porphobilinogen synthase, a porphobilinogen deaminase, an uroporphyrinogen synthase, an uroporphyrinogen decarboxylase, a coproporphyrinogen oxidase, a protoporphyrinogen oxidase, and a ferrochelatase. The second nucleic acid sequences may be obtained from any microbial source. The choice of the source of the second nucleic acid sequence will depend on the filamentous fungal host cell, but preferred sources are fungal sources, e.g., yeast and filamentous fungi. Preferred filamentous fungal sources include, but are not limited to, species of Acremonium, Aspergillus, Fusarium, Humicola, Myceliophthora, Mucor, Neurospora, Penicillium, Phanerochaete, Thielavia, Tolypocladium, and Trichoderma. Preferred yeast sources include, but are not limited to, species of Candida, Klyveromyces, Pichia, Saccharomyces, Schizosaccharomyces, and Yarrowia. Furthermore, the second nucleic acid sequences may be native to the filamentous fungal host cell.

The second nucleic sequence may be one or more of the following:

1. 5-Aminolevulinic acid synthase genes:
    a. *Saccharomyces cerevisiae* (Urban-Grimal et al., 1986, European Journal of Biochemistry 156:511–59);
    b. *Aspergillus nidulans* (Bradshaw et al., 1993, *Current Genetics* 23:501–507);
    c. *Rhodobacter sphaeroides* (Tai et al., 1988, *Gene* 70:139–152);
    d. *Rhodobacter capsulatus* (Homberger et al., 1990, *Molecular General Genetics* 211:371–378); and
    e. *Escherichia coli* (Drolet et al., 1989, *Molecular General Genetics* 216:347–352).

2. Porphobilinogen synthase genes:
    a. *Saccharomyces cerevisiae* (Myers et al., 1987, *Journal of Biological Chemistry* 262:16822–16829);
    b. *Staphylococcus aureus* (Kafala and Sasarman, 1994, *Canadian Journal of Microbiology* 40:651–657);
    c. *Rhodobacter sphaeroides* (Delaunay et al., 1991, *Journal of Bacteriology* 173:2712–2715);
    d. *Escherichia coli* (Echelard et al., 1988, *Molecular General Genetics* 214:503–508); and
    e. *Bacillus subtilis* (Hansson et al., 1991, *Journal of Bacteriology* 173:2590–2599).

3. Porphobilinogen deaminase genes
    a. Saccharomyces cerevisiae (Keng et al., 1992, *Molecular General Genetics* 234:33–433);
    b. human (Yoo et al., 1993, *Genomics* 15:221–29; Raich et al., 1986, *Nucleic Acids Research* 14:5955–5968);
    c. *Escherichia coli* (Thomas and Jordan, 1986, *Nucleic Acids Research* 14:6215–6226); and
    d. *Bacillus subtilis* (Petricek et al., 1990, *Journal of Bacteriology* 172:2250–2258).

4. Uroporphyrinogen III synthase genes:
    a. *Saccharomyces cerevisiae* (Amillet and Labbe-Bois, 1995, *Yeast* 11:419–424);
    b. *Bacillus subtilis* (Hansson et al., 1991, *Journal of Bacteriology* 173:2590–2599); and
    c. *Escherichia coli* (Jordan et al., 1987, *Nucleic Acids Research*. 15:10583).

5. Uroporphyrinogen III decarboxylase genes:
    a. *Saccharomyces cerevisiae* (Garey et al., 1992, *European Journal of Biochemistry* 205:1011–1016); and
    b. human (Romeo et al., 1986, *Journal of Biological Chemistry* 261:9825–9831).

6. Coproporphyrinogen III oxidase genes:
    a. human (Martasek et al., 1994, *Proceedings of the National Academy of Sciences USA* 911:3024–3028);
    b. *Escherichia coli* (Troup et al., 1994, *Journal of Bacteriology* 176:673–680); and
    c. *Saccharomyces cerevisiae* (Zaagorec et al., 1986, *Journal of Biological Chemistry* 263:9718–9724).

7. Protoporphyrinogen IX oxidase genes:
    a. human (Taketani et al., 1995, Genomics 29:698–703);
    b. *Bacillus subtilis* (Dailey et al., 1994, *Journal of Biological Chemistry* 269:813–815); and
    c. *Escherichia coli* (Sasarrnan et al., 1993, *Canadian Journal of Microbiology* 39:155–161).

8. Ferrochelatase genes:
    a. *Saccharomyces cerevisiae* (Labbe-Bois, 1990, *Journal of Biological Chemistry* 265:7278–72883);
    b. bovine (Shibuya et al., 1995, *Biochimica Biophysica Acta* 1231:117–120);
    c. *Bradyrhizobium japonicum* (Frustaci and O'Brian, 1993, *Applied Environmental Microbiology* 59:347–2351);
    d. *Escherichia coli* (Frustaci and O'Brian, 1993, *Journal of Bacteriology* 175:2154–2156); and
    e. *Bacillus subtilis* (Hansson and Hederstedt, 1992, *Journal of Bacteriology* 174:8081–88093).

In a more preferred embodiment, the second nucleic acid sequences are obtained from a species of Aspergillus. In an even more preferred embodiment, the second nucleic acid sequences are obtained from *Aspergillus ficuum, Aspergillus foetidus, Aspergillus japonicus, Aspergillus niger, Aspergil-*

*lus nidulans*, or *Aspergillus oryzae*. In another more preferred embodiment, the second nucleic acid sequences are obtained from a species of Saccharomyces. In an even more preferred embodiment, the second nucleic acid sequences are obtained from *Saccharomyces cerevisiae, Saccharomyces carlsbergensis, Saccharomyces diastaticus, Saccharomyces douglasii, Saccharomyces kluyveri, Saccharomyces norbensis*, or *Saccharomyces oviformis*.

In a most preferred embodiment, the second nucleic acid sequence encoding a 5-aminolevulinic acid synthase is obtained from *Aspergillus oryzae* strain A1560 (IFO 4177), e.g., the nucleic acid sequence set forth in SEQ ID NO: 1. The second nucleic sequence encoding a 5-aminolevulinic acid synthase may also be a nucleic acid sequence coding for the 5-aminolevulinic acid synthase having the amino acid sequence set forth in SEQ ID NO:2, which differs from SEQ ID NO: 1 by virtue of the degeneracy of the genetic code. In another most preferred embodiment, the second nucleic acid sequence encoding a porphobilinogen synthase is obtained from *Aspergillus oryzae* strain A1560 (IFO 4177), e.g., the nucleic acid sequence set forth in SEQ ID NO:3. The second nucleic acid encoding a porphobilinogen synthase may further be a nucleic acid sequence coding for the porphobilinogen synthase having the amino acid sequence set forth in SEQ ID NO:4, which differs from SEQ ID NO:3 by virtue of the degeneracy of the genetic code. The second nucleic acid sequences of the present invention further encompass both the genomic sequences depicted in SEQ ID NO: 1 and SEQ ID NO:3 as well as the corresponding cDNA and RNA sequences. The phrase "nucleic acid sequences" as used herein will be understood to encompass all such variations including synthetic DNA.

In a preferred embodiment, the second nucleic acid sequence is introduced into the filamentous fungal host, operably linked to one or more second control sequences. The second control sequences may be native to the second nucleic acid sequences encoding the heme biosynthetic enzymes or may be partially or wholly obtained from foreign sources. The foreign control sequences may simply replace the natural control sequences in order to obtain enhanced production of the desired heme biosynthetic enzyme relative to the natural control sequence normally associated with the coding sequence. The second control sequences can be any of the control sequences exemplified above in connection with the first control sequences.

In another aspect of the present invention, one or more copies of one or more first control sequences and one or more copies of one or more second nucleic acid sequences are introduced into the filamentous fungal cell. Preferably, the second nucleic acid sequences are operably linked to one or more second control sequences.

The first control sequences, the second nucleic acid sequences and/or the second control sequences may be contained in the same nucleic acid construct, or they may be contained in different nucleic acid constructs. Each nucleic acid construct may comprise integrational elements for directing integration by homologous recombination into the genome of the fungal host at a precise location. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the filamentous fungal host cell.

Furthermore, the integrational elements may be non-encoding or encoding nucleic acid sequences. On the other hand, each nucleic acid construct may be integrated into the genome of the filamentous fungal host cell by non-homologous recombination.

The nucleic acid constructs may be inserted into a suitable vector or the second nucleic acid sequences may be inserted directly into a vector which already contains the control sequences using molecular biology techniques known in the art. The vectors may be any vector which can be conveniently subjected to recombinant DNA procedures and can bring about the expression of a nucleic acid sequence of the present invention. The choice of a vector will typically depend on the compatibility of the vector with the filamentous fungal cell into which the vector is to be introduced. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. Alternatively, the vector may be one which, when introduced into the filamentous fungal cell, is integrated into the genome and replicated together with the chromosome(s) into which it has been integrated. The vector system may be a single vector or plasmid or two or more vectors or plasmids which together contain the total DNA to be introduced into the genome of the filamentous fungal host.

The vectors of the present invention preferably contain one or more selectable markers which permit easy selection of transformed cells. A selectable marker is a gene the product of which provides for biocide or viral resistance, resistance to heavy metals, prototrophy to auxotrophs and the like. The selectable marker may be selected from the group consisting of, but not limited to, amdS, pyrG, argB, niaD, sC, trpC, bar, and hygB. Preferred for use in an Aspergillus cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243 where the selectable marker is contained in a separate vector.

The procedures used to ligate the nucleic acid constructs, the promoter, terminator and other elements, and to insert them into suitable vectors containing the information necessary for replication, are well known to persons of ordinary skill in the art (cf., for instance, Sambrook et al., *Molecular Cloning, A Laboratory Manual*, 2d ed., Cold Spring Harbor, N.Y., 1989).

The methods of the present invention may further comprise introducing one or more copies of one or more third nucleic acid sequences encoding the hemoprotein into the filamentous fungal cell. The third nucleic acid sequence encoding the hemoprotein may be introduced prior to or after step a, but before step b. The third nucleic acid sequence may be contained in the same vector as the first control sequences, the second nucleic acid sequences and the second control sequences, or they may be contained in different vectors. Preferably, the third nucleic acid sequences are operably linked to third control sequences. The control sequences exemplified above in connection with the first control sequences are also applicable to the third control sequences.

The methods of the present invention may further comprise introducing a source of heme, analogs thereof or one or more pathway intermediates into the nutrient medium. See Product Brochure of Porphyrin Products Inc. (Logan, Utah) for list of heme analogs and pathway intermediates.

For example, when a nucleic acid sequence encoding one of the enzymes in the heme biosynthetic pathway is introduced into a filamentous fungal cell, one or more pathway intermediates in one or more preceding steps may become rate-limiting. In such a case, one can supplement the culture medium with these one or more pathway intermediates. In order for these pathway intermediates to get introduced into the cell, one can use an enzyme which is capable of semi-permeabilizing the cell membrane, e.g., NOVOZYM 234™ (Novo Nordisk A/S).

The methods of the present invention may further comprise introducing a source of iron into the nutrient medium. Alternatively, the methods further comprise introducing any other metal ion that can induce porphyrin synthesis. See, e.g., Mamet et al., 1996, *BioMetals,* 9:73–77.

The present invention also relates to recombinant filamentous fungal cells comprising one or more first control sequences capable of directing the expression of a heme biosynthetic enzyme encoded by a first nucleic acid sequence endogenous to the filamentous fungal cell and/or one or more copies of one or more second nucleic acid sequences encoding a heme biosynthetic enzyme. The sequences may be integrated into the genome of the fungal cell or may be contained in a self-replicating extrachromosomal vector.

The filamentous fungal cells of the present invention may further comprise one or more copies of a third nucleic acid sequence encoding a hemoprotein, wherein the third nucleic acid sequence is operably linked to third control sequences capable of directing the expression of the hemoprotein in the filamentous fungal cell, where the third nucleic acid sequence encoding the hemoprotein is integrated into the genome of the fungal cell or is contained in a self-replicating extrachromosomal vector.

The choice of filamentous fungal host cells will to a large extent depend upon the sources of the control sequences, the nucleic acid sequences encoding the heme biosynthetic enzymes, and the hemoprotein. In a preferred embodiment, the filamentous fungal host cell is a cell of a species of, but not limited to, Acremonium, Aspergillus, Fusarium, Humicola, Myceliophthora, Mucor, Neurospora, Penicillium, Thielavia, Tolypocladium, and Trichoderma. In a more preferred embodiment, the filamentous fungal host cell is an Aspergillus cell. In another more preferred embodiment, the filamentous fungal host cell is an Acremonium cell. In another more preferred embodiment, the filamentous fungal host cell is a Fusarium cell. In another more preferred embodiment, the filamentous fungal host cell is a Humicola cell. In another more preferred embodiment, the filamentous fungal host cell is a Myceliophthora cell. In another more preferred embodiment, the filamentous fungal host cell is a Mucor cell. In another more preferred embodiment, the filamentous fungal host cell is a Neurospora cell. In another more preferred embodiment, the filamentous fungal host cell is a Penicillium cell. In another more preferred embodiment, the filamentous fungal host cell is a Thielavia cell. In another more preferred embodiment, the filamentous fungal host cell is a Tolypocladium cell. In another more preferred embodiment, the filamentous fungal host cell is a Trichoderma cell. In a most preferred embodiment, the filamentous fungal host cell is an *Aspergillus ficuum* cell, an *Aspergillus foetidus* cell, an *Aspergillus japonicus* cell, an *Aspergillus niger* cell, an *Aspergillus nidulans* cell, or an *Aspergillus oryzae* cell. In another most preferred embodiment, the filamentous fungal host cell is a *Fusarium oxysporum* cell or a *Fusarium graminearum* cell. In another most preferred embodiment, the filamentous fungal host cell is a *Humicola insolens* cell or a *Humicola lanuginosus* cell. In another most preferred embodiment, the filamentous fungal host cell is a *Myceliophthora thermophilum* cell. In another most preferred embodiment, the filamentous fungal host cell is a *Mucor miehei* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the filamentous fungal host cell is a *Trichoderma harzianum* cell, a *Trichoderma koningii* cell, a *Trichoderma longibrachiatum* cell, a *Trichodenna reesei* cell, or a *Trichoderma viride* cell.

The present invention is further described by the following examples which should not be construed as limiting the scope of the invention.

EXAMPLES

EXAMPLE 1

*Aspergillus oryzae* strain A1560 genomic DNA extraction

*Aspergillus oryzae* strain A1560 (IFO 4177) was grown in 25 ml of 0.5% yeast extract-2% glucose (YEG) medium for 24 hours at 32° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to insure mixing, and extracted twice with an equal volume of phenol:chloroform:isoamyl alcohol (25:24:1 v/v/v). Sodium acetate (3 M solution) was added to a final concentration of 0.3 M followed by addition of 2.5 volumes of ice cold ethanol to precipitate the nucleic acids. The nucleic acids were then pelleted by centrifuging the tube at 15,000×g for 30 minutes. The pellet was allowed to air dry for 30 minutes before resuspension in 0.5 ml of TE buffer. DNase-free ribonuclease A was added to a concentration of 100 µtg/ml and the mixture was incubated at 37ûC for 30 minutes. Proteinase K was then added at a concentration of 200 µg/ml and the mixture was incubated an additional hour at 37° C. Finally, the mixture was extracted twice with phenol:chloroform:isoamyl alcohol (25:24:1 v/v/v) before precipitating the DNA with sodium acetate and ethanol as described earlier. The DNA pellet was dried under vacuum, resuspended in TE buffer, and stored at 4° C. until further use.

EXAMPLE 2

Construction of plasmid pSE04

Figure 1:
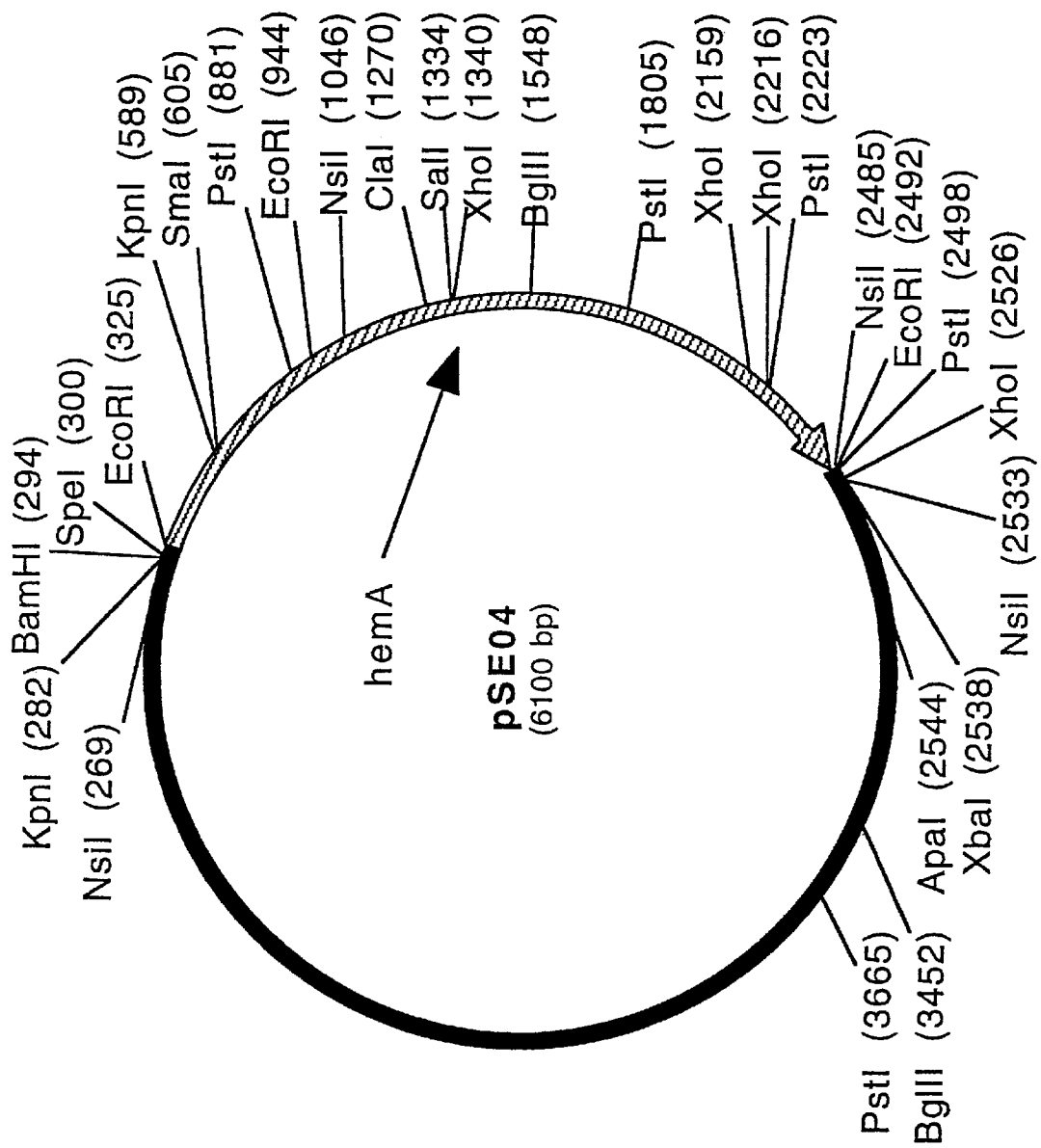
FIG. 1 shows a restriction map of plasmid pSE04.

Genomic DNA was obtained from *Aspergillus nidulans* strain A26 (Fungal Genetics Stock Center, Kansas City, Kans.) using the same procedure described in Example 1. Plasmid pSE04 was constructed by ligation of PCR fragments from an amplification reaction containing *Aspergillus nidulans* A26 genomic DNA. The amplification reaction contained the following components: 50 ng of *Aspergillus nidulans* A26 genomic DNA, 100 µM each of dATP, dCTP, dGTP, and dTTP (Boehringer Mannheim, Indianapolis, Ind.), 50 pmoles of primers ALAS3d 5'-TTTATGATGGAGGCCCTTCTCCAGCAGTCTC-3' (SEQ ID NO:5) and ALAS4e 5'-CTATGCATTTAAGCAGCAGCCGCGACTGG-3' (SEQ ID NO: 6), 2 units of Taq DNA polymerase (Perkin-Elmer Corp., Branchburg, N.J.), and 1×Taq DNA polymerase buffer (Perkin-Elmer Corp., Branchburg, N.J.). The reaction was incubated in a Perkin-Elmer Thermal Cycler (Perkin-Elmer Corp., Branchburg, N.J.) programmed for 30 cycles each at 95° C. for 1 minute, 55° C. for 1 minute, and 72° C. for 90 seconds. The 2 kb PCR product was isolated by excision after electrophoresis using a 1.1 % low melting temperature agarose gel (FMC, Rockland, Me.) with 40 mM Tris-acetate-1 mM disodium EDTA (TAE) buffer, and subcloned into the pCRII vector (Invitrogen, San Diego, Calif.) according to the manufacturer's instructions to produce pSE04 (FIG. 1).

EXAMPLE 3

Aspergillus oryzae strain A1560 DNA libraries and identification of ALA synthase (hemA) clones Aspergillus oryzae strain A1560 genomic DNA libraries were constructed using the bacteriophage cloning vector λZipLox (Life Technologies, Gaithersburg, Md.) according to the manufacturer's instructions using E. coli Y1090ZL cells as a host for plating and purification of recombinant bacteriophage and E. coli DH10Bzip for excision of individual pZL1-hemA clones. Total cellular DNA prepared as described in Example 1 was partially digested with Tsp509I and size-fractionated on a 1% agarose gel with 50 mM Tris-50 mM borate-1 mM disodium EDTA (TBE) buffer. DNA fragments migrating in the size range 4–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms, and the ligation mixtures were packaged using commercial packaging extracts (Stratagene, La Jolla, Calif.). The packaged DNA libraries were plated and amplified in E. coli Y1090ZL cells. The unamplified genomic library contained $1 \times 10^6$ pfu/ml.

Figure 2:
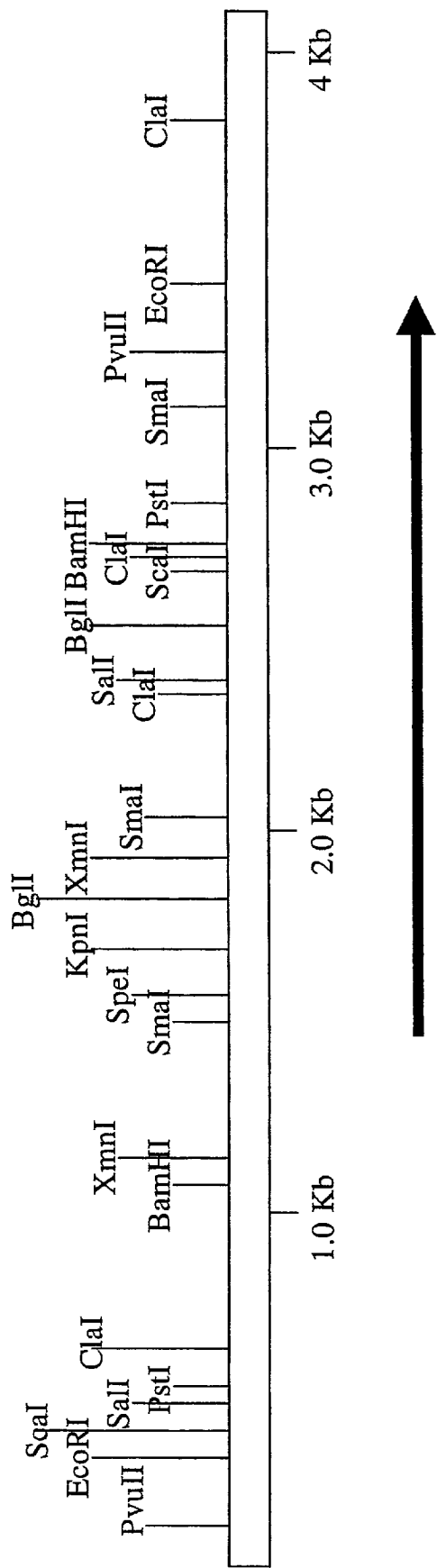
FIG. 2 shows a restriction map of a 4.2 kb genomic fragment containing an *Aspergillus oryzae* 5-aminolevulinic acid synthase gene. Scale in kilobases (kb) is shown under the map. The arrow represents the location of the open reading frame of the gene.

Bacteriophage DNA from $7 \times 10^4$ plaques was transferred to duplicate circular Nytran Plus membranes (Schleicher & Schuell, Keene, N.H.) and probed with a digoxigenin (DIG)-labeled probe which was prepared by PCR amplification of Aspergillus nidulans hemA genomic DNA from plasmid pSE04 described in Example 2. The amplification reaction contained the following components: 1×DIG probe synthesis mix (Boehringer Mannheim, Indianapolis, Ind.), 100 μM each of dATP, dCTP, dGTP, and dTTP, 50 pmoles of primer ALAS3d and primer ALAS4e described in Example 2, 2 units of Taq DNA polymerase, and 1×Taq DNA polymerase buffer. The reaction was incubated in a Perkin-Elmer Thermal Cycler programmed for 30 cycles each at 95° C. for 1 minute, 55° C. for 1 minute, and 72° C. for 2 minutes. Denatured probe was added to the hybridization buffer at a concentration of 2 ng/ml and incubated overnight with prehybridized membranes. Prehybridization and hybridization was conducted at 42° C. in 5×SSC, 0.1% sarkosyl, 0.02% SDS, 1% Genius blocking agent (Boehringer Mannheim, Indianapolis, Ind.), and 30% formamide. Membranes were washed twice in 5×SSC-0.1% SDS followed by two washes in 2×SSC-0.1% SDS. Each wash was performed for 15 minutes at room temperature. The washed membrane was exposed to Kodak X-OMAT AR film for approximately 2 hours at room temperature followed by development using a Konica QX-70 automatic film processor according to the manufacturer's instructions. Primary plaques were purified and screened a second time. Five clones were identified and excised into pZL derivatives according to the manufacturer's instructions (Bethesda Research Laboratories, Inc., Gaithersburg, Md.). The pZL derivatives were designated E. coli DH5α pSE11, pSE13, pSE15, pSE17, and pSE20. These clones were found to overlap and span a 4.2 kb region for which the restriction map is shown in FIG. 2.

EXAMPLE 4

Southern hybridization of Aspergillus oryzae strain A1560 genomic DNA with a 5-aminolevulinic acid synthase (hemA) probe Aspergillus oryzae strain A1560 genomic DNA (10 μg) prepared as described in Example 1 was restriction digested with either BamHI or EcoRI. The fragments were separated by electrophoresis on a 1 % agarose-TBE gel. DNA was transferred to a Nytran Plus membrane in 0.4 N NaOH using a TurboBlot apparatus (Schleicher & Schuell, Keene, N.H.) according to the manufacturer's instructions. The membrane was prehybridized for 2 hours at 42° C. in 5×SSC, 0.1% sarkosyl, 0.02% SDS, 1% Genius blocking agent (Boehringer Mannheim, Indianapolis, Ind.), and 50% formamide in a Hybaid oven (Labnet, Woodbridge, N.J.). Hybridization was accomplished with a DIG-labeled hemA probe generated by PCR amplification as described in Example 3, except the hemA clone pSE17 was used as a template with primer hemA5' 5'-TCATTTAAATGATGGAGTCTCTTCTCC-3' (SEQ ID NO:7) and primer hemA3' 5'-TCTTAATTAATCAGCTCACATGCGGG-3' (SEQ ID NO:8). DIG-labeled hemA probe (1 ng probe/ml of solution) was added to fresh hybridization buffer and incubated with the membrane overnight at 42° C. Subsequently, the membrane was washed twice for 15 minutes each at room temperature in 5×SSC-0.1% SDS followed by two washes under the same conditions in 2×SSC-0.1% SDS. The washed membrane was exposed to Kodak X-OMAT AR film for approximately 2 hours at room temperature followed by development using a Konica QX-70 automatic film processor according to the manufacturer's instructions.

Southern blot hybridization of Aspergillus oryzae genomic DNA with the Aspergillus oryzae hemA probe showed the presence of hybridization signals consistent with a single gene copy number. A 1.7 kb band observed in the BamHI lane was predicted from the restriction map (FIG. 2).

EXAMPLE 5

Characterization of Aspergillus oryzae A1560 5-aminolevulinic acid synthase (hemA) gene E. coli DH5a pSE17 described in Example 3 was subjected to DNA sequencing according to the following procedure. DNA sequencing was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38:47–60) using the M13 reverse (−48) and M13 forward (−20) primers (New England Biolabs, Beverly, Mass.) and primers unique to the DNA being sequenced.

The nucleotide sequence of the cloned gene revealed an open reading frame of 1911 nucleotides as shown in FIG. 3 (SEQ ID NO: 1). The coding sequence does not contain any introns which was confirmed by cDNA cloning and sequence analysis which is in contrast to the *Aspergillus nidulans* hemA gene which contains one intron at its 5' end (Bradshaw et al., 1993, *Current Genetics* 23:501–507). The 5' untranslated sequence contains several pyrimidine-rich and AT-rich regions as in other fungal genes (Gurr et al., 1987, In Kinghorn, J. R. (ed.), *Gene Structure in Eukaryotic Microbes,* pp. 93–139, IRL Press, Oxford), a CCAAT sequence at position −249, and a putative TATA box located at position −35. The CCAAT sequence is a consensus binding site for transcriptional regulators which modulate transcription in response to oxygen, such as the Hap2/3/4 transcriptional regulatory complex in yeast and humans (Olesen and Guarente, 1990, *Molecular and Cellular Biology* 12:2302–2314). This regulatory complex is also conserved in mammals, and a CCAAT-binding activity has been identified in *Aspergillus nidulans* (Davis et al., 1993, *Genetica* 90:133–145). The importance of this sequence in the *Aspergillus oryzae* hemA gene is not known and, due to limited sequence information, has not been confirmed in the *Aspergillus nidulans* hema 5' region (Bradshaw et al., 1993, supra). Transcriptional regulation of the *Aspergillus oryzae* hemA gene in response to oxygen is not currently known, but the *Aspergillus nidulans* hemA gene does not appear to be transcriptionally regulated even under conditions of oxygen limitation (Bradshaw et al., 1993, supra). Interestingly, the yeast HEM1 gene is also constitutively expressed, but its expression is controlled by a balance between positive and negative regulatory sites (Keng and Guarente, 1987, *Proceedings of the National Academy of Sciences USA* 84:9113–9117). An (AC)$_{35}$ repeat motif occurs in the 3' untranslated region. Similar repeats have also been observed in subtelomeric, intron, and promoter regions of mammalian and yeast genes and have no known function, although they have been implicated in gene amplification events (Passananti et al., 1987, *EMBO Journal* 6:1697–1703).

The deduced amino acid sequence of the *Aspergillus oryzae* strain A1560 gene product is shown in FIG. 3 (SEQ ID NO:2). The nucleotide sequence encodes a predicted protein of 636 amino acids with a molecular weight of 68 kDa. Since this enzyme is located in the mitochondria, the N-terminus is predicted to contain a mitochondrial leader sequence. In fact, the first 35 amino acids are rich in serine, threonine, lysine, and arginine residues consistent with a function as a mitochondrial leader. A potential heme regulatory motif (HRM) occurs in the presumed mitochondrial leader sequences of both the *Aspergillus nidulans* and *Aspergillus oryzae* hemA sequences (FIG. 4). HRMs localized to leader sequences are believed to prevent import of 5-aminolevulinic acid synthase proteins into the mitochondria in mouse via direct interactions with heme (Lathrop and Timko, 1993, *Science* 259:522–525; Zhang and Guarente, 1995, *EMBO Journal* 14:313–320). A second potential HRM also occurs in the beginning of the putative mature protein sequence. It is probable that the HRMs play a role in the regulation of 5-aminolevulinic acid synthase activity. Interestingly, the *Saccharomyces cerevisiae* 5-aminolevulinic acid synthase protein sequence does not contain any putative HRMs and does not appear to be a key regulatory step in yeast heme biosynthesis (Labbe-Bois and Labbe, In Daley, Harry A., ed., *Biosynthesis of Heme and Chlorophylls,* 1990, McGraw Hill Publishers, New York, pp 235–285).

Overall, the deduced amino acid sequence as shown in FIG. 5 shares 81 % identity with the *Aspergillus nidulans* hemA gene (SEQ ID NO:22), 57% identity with the *Saccharomyces cerevisiae* HEM1, gene (SEQ ID NO:23; Urban-Grimal, 1986, *European Journal of Biochemistry* 156:511–519). and 51% identity with the human erythroid hem1 (ALAS2) gene (SEQ ID NO:24; Bishop, 1990, *Nucleic Acids Research* 18:7187–7188) which were determined using the Applied Biosystems GeneAssist program (blosum62.mat matrix). However, the highest degree of conservation occurs in the C-terminal two-thirds of the protein which contains the catalytic domain. Furthermore, the lysine and glycine-loop, important for catalytic activity and pyridoxal phosphate co-factor binding in other 5-aminolevulinic acid synthase enzymes (Ferreira et al., 1995, *Journal of Bioenergetics and Biomembranes* 27:151–159; Ferreira, 1995, *Protein Science* 4:1001–1006) are also highly conserved.

EXAMPLE 6

Construction of plasmid pSE31

Plasmid pSE31 was constructed by directional cloning of PCR-amplified *Aspergillus oryzae* hemA DNA into pBANe6 (FIG. 6). The PCR amplification reaction was performed using DNA from hemA clone *E. coli* DH5α pSE17 described in Example 3 where the reaction contained the following components: 50 ng of pSE17, 2 units of Vent DNA polymerase (New England Biolabs, Beverly, Mass.), IX Vent DNA polymerase buffer (New England Biolabs, Beverly, Mass.), 400 μM each of dATP, dCTP, dGTP, and dTTP (Boehringer Mannheim, Indianapolis, Ind.), and 50 pmoles of primer hemA5' 5'-TCATTTAAATGATGGAGTCTCTTCTCC-3' (SEQ ID NO:7) and primer hemA3' 5'-TCTTAATTAATCAGCTCACATGCGGG-3' (SEQ ID NO:8). The reaction was incubated in a Perkin-Elmer Thermal Cycler programmed for 30 cycles each at 95° C. for 1 minute, 55° C. for 1 minute, and 72° C. for 90 seconds. Primer hemA5' contains a SwaI site (underlined) and primer hemA3' contains a PacI site (underlined) which were used for cloning into pBANe6 digested with SwaI and PacI to produce pSE31 (FIG. 7).

EXAMPLE 7

Construction of *Aspergillus oryzae* strain JRoC50.3.18A

*Aspergillus oryzae* strain JRoC50.3.18A containing plasmid pJROC50 was constructed as follows. *Coprinus cinereus* IFO 8371 peroxidase cDNA fragments were prepared by PCR using specific oligonucleotide primers shown below (Saiki et al., 1988, *Science* 239:487–491) constructed on the basis of the amino acid sequence of the Coprinus macrorhizus peroxidase (Baunsgaard et al., 1993, *European Journal of Biochemistry* 213:605–611):

1. 5'-GCGCGAATTCGTNGGNATNGGNATNAA(CT)CA(CT)GG-3' (SEQ ID NO:9)
2. 3'-TACAGNTT(GA)AC(GA)GGNGGCCTAGGCG-5' (SEQ ID NO:10)
3. 5'-GCGAATTCACNCCNCA(GA)GTNTT(CT)GA(CT)AC-3' (SEQ ID NO:11)
4. 3'-GGNAA(GA)GGNCCNCT(CT)AA(GA)CCTAGGCG-5' (SEQ ID NO:12)
5. 5'-GCGCGAATTCTGGCA(GA)TCNAC-3' (SEQ ID NO:13)
6. 5'-GCGCGAATTCTGGCA(GA)AGNATG-3' (SEQ ID NO:14)
7. 3'-CGNTACCGNTT(CT)TACAGCCTAGG-5' (SEQ ID NO:15)

PCR was performed using the Gene Amp Kit and apparatus (Perkin Elmer Cetus, Norwalk, Conn.) in accordance with the manufacturer's instructions with the exception that the reaction was conducted at 28° C. for the first 3 cycles in order to obtain better hybridization to the first strand cDNA (prepared from mRNA obtained from *Coprinus cinereus* strain IFO 8371) and subsequently at 65° C. for 30 cycles of PCR.

The primers were combined as follows: 1 with 2; 3 with 4; 5 with 7; 6 with 7; 1 with 4; and 3 with 7. The PCR fragments were extended with an EcoRI site at the 5'-end and a BamHI site at the 3'-end. The reactions were analyzed on a 1 % agarose-TBE gel where bands of the expected size were found in all the reactions. To verify that the bands corresponded to peroxidase-specific sequences, the gel was subjected to Southern blotting and hybridized to an oligonucleotide probe with the following sequence which is positioned between primers 3 and 4:

5'-GT(CT)TC(GA)AT(GA)TAGAA(CT)TG-3' (SEQ ID NO: 16)

The probe was found to hybridize to bands of approximately 130 bp, 420 bp, 540 bp, and 240 bp, thus confirming that the DNA bands observed corresponded to peroxidase sequences.

DNA from the various PCR reactions was digested with EcoRI and BamHI and cloned into the plasmid pUC19 (New England BioLabs, Beverly, Mass.). Colonies containing the correct PCR fragments were identified by hybridization using the oligonucleotide probe (SEQ ID NO: 16) described above. DNA from positive colonies was analyzed by restriction mapping and partial DNA sequence analysis as described by Sanger et al. (1977, *Proceedings of the National Academy of Sciences USA* 74:5463–5467). A 430 bp fragment from one of the clones, obtained by using primers 1 and 4, was used to screen a *Coprinus cinereus* cDNA library as described below.

Total RNA was extracted from homogenized *Coprinus cinereus* strain IFO 8371 mycelia, collected at the time of maximum peroxidase activity according to the methods described by Boel et al. (1984, *EMBO Journal* 3:1097–1102) and Chirgwin et al. (1979, *Biochemistry* 18:5294–5299). Poly(A)-containing RNA was obtained by two cycles of affinity chromatography on oligo(dT)-cellulose as described by Aviv and Leder (1972, *Proceedings of the National Academy of Sciences USA* 69:1408–1412). cDNA was synthesized by means of a cDNA Synthesis Kit (Invitrogen, San Diego, Calif.) according to the manufacturer's instructions. Approximately 50,000 *E. coli* recombinants from the *Coprinus cinereus* cDNA library were transferred to Whatman 540 paper filters. The colonies were lysed and immobilized as described by Gerger et al. (1979, *Nucleic Acids Research* 7:2115–2135). The filters were hybridized with the $^{32}$P-labelled 430 bp peroxidase-specific probe in 0.2×SSC-0.1% SDS. Hybridization and washing of the filters was conducted at 65° C. followed by autoradiography for 24 hours with an intensifier screen. After autoradiography, the filters were washed at increasing temperatures followed by autoradiography for 24 hours with an intensifier screen. In this way, more than 50 positive clones were identified. Miniprep plasmid DNA was isolated from hybridizing colonies by standard procedures (Bimboim and Doly, 1979, *Nucleic Acids Research* 7:1513–1523), and the DNA sequences of the cDNA inserts were determined by the Sanger dideoxy procedure (Sanger et al., 1977, *Proceedings of the National Academy of Sciences USA* 74:5463–5467). One of the colonies was selected and the vector was designated pCiP. The peroxidase cDNA fragment was excised from the vector by cleavage with BamHI/XhoI and was purified by agarose gel electrophoresis, electroeluted and made ready for ligation reactions. The cDNA fragment was ligated to BamHI/XhoI digested pHD414 to generate pJVi9 wherein the cDNA was under transcriptional control of the TAKA promoter from *Aspergillus oryzae* and the AMG™ (Novo Nordisk A/S, Bagsvæxrd, Denmark) terminator from *Aspergillus niger* as shown in FIG. 8.

The cDNA encoding the *Coprinus cinereus* peroxidase was excised from plasmid pJVi9 as a BamHI-XhoI fragment and cloned into plasmid pJeRS6 (FIG. 9) to produce plasmid pJRoC50 (FIG. 10) which contains pyrG as a selectable marker, the TAKA promoter, and the amdS terminator.

Transformants of *Aspergillus oryzae* strain HowB425 were made using 5 µg of purified plasmid pJRoC50 as described below with the following changes. The agar overlay was omitted and the protoplasts were plated directly on Minimal Medium plates. The transformation was conducted with protoplasts at a concentration of 2×10$^7$ protoplasts per ml. One hundred µl of protoplasts were placed on ice with 5 µg DNA for 30 minutes. One ml of SPTC (40% PEG 4000, 0.8 M sorbitol, 0.05 M Tris pH 8.0, 0.05 M CaCl$_2$) was added and the protoplasts were incubated at 34° C. for 20 minutes. The transformation was plated directly onto plates containing Minimal medium. The Minimal medium (pH 6.5) was composed of 6 g of NaNO$_3$, 0.52 g of KCl, 1.52 g of KH$_2$PO$_4$, 1 ml of trace metals, 1 g of glucose, 500 mg of MgSO$_4$-7H$_2$O, 342.3 g of sucrose, and 20 g of Noble agar per liter. The trace metals solution (1000×) was composed of 22 g of ZnSO$_4$-7H$_2$O, 11 g of H$_3$BO$_3$, 5 g of MnCl$_2$-4H$_2$O, 5 g of FeSO$_4$-7H$_2$O, 1.6 g of CoCl$_2$-5H$_2$O, 1.6 g of (NH$_4$)$_6$Mo$_7$O$_{24}$, and 50 g of Na$_4$EDTA per liter. Plates were incubated 5–7 days at 34° C. Transformants were transferred to plates of the same medium and incubated 3–5 days at 37° C.

Sixty-six transformants were assayed for peroxidase activity using the following enzyme assay: 180 µl of substrate buffer {20 ml of 0.1 M potassium phosphate-0.01 % Tween-80 pH 7.0, 250 µl of 2,2'-azinobis(3-ethylbenzothiazoline-6-sulfonate) (ABTS) solution (22 mg/ml), and 2 µl of 30% hydrogen peroxide} were added to 20 µL of culture supernatant which was diluted 1:900, quickly followed by measurement of the absorbance at 405 nm at 25° C. using a Molecular Devices Thermomax Microplate Reader (Molecular Devices, Sunnyvale, Calif.). Measurements were recorded every 10 seconds over a 2 minute period with mixing and V$_{max}$ values were calculated using the SOFTmax program (Molecular Devices, Sunnyvale, Calif.). The peroxidase units (POXU) per ml were estimated using a standard curve constructed with a known amount of *Cinereus coprinus* peroxidase as a standard. A POXU was defined as the amount of enzyme that catalyzes the conversion of 1.0 µmole per minute of 0.88 mM H$_2$O$_2$, 1.67 mM ABTS, 0.1 M phosphate pH 7.0 at 30° C. The four transformants expressing the highest levels were spore purified by streaking spores and picking isolated colonies using the same plates under the same conditions described above.

Final evaluations were performed in shake flasks where approximately 5×10$^6$ spores of each transformant were inoculated into 25 ml of MY25 medium containing 1% yeast extract, 2.5% maltose, 0.2% urea, and 1×MY salts pH 6.5. 1×MY salts was composed of 2 g of MgSO$_4$-7H$_2$O, 2 g of K$_2$PO$_4$, 10 g of KH$_2$PO$_4$, 2 g of citric acid, 0.5 ml of trace metals solution and 1 ml of 10% CaCl$_2$-2H$_2$O per liter. The trace metals solution was composed of 13.9 g of FeSO$_4$-7H$_2$O, 8.5 g of MnSO$_4$-H$_2$O, 14.28 g of ZnSO$_4$-7H$_2$O, 1.63 g of CuSO$_4$, 0.24 g of NiCl$_2$-6H$_2$O, and 3.0 g of citric acid per liter. Hemin was added to a final concentration of 0.01 mg/ml from a fresh 10 mg/ml stock prepared in 50 mM NaOH. The shake flasks were incubated at 34° C. and 200 rpm for 7 to 8 days. The best peroxidase producer was designated JRoC50.3.18A.

EXAMPLE 8

Transformation of *Aspergillus oryzae* JRoC50.3.18A with pSE31

*Aspergillus oryzae* strain JRoC50.3.18A was transformed with pSE31 in order to determine whether overexpression of the hemA gene increased peroxidase production.

The transformation was conducted with protoplasts at a concentration of $2 \times 10^7$ protoplasts per ml. One hundred µl of protoplasts were incubated at 34° C. with 10 µg DNA and 200 µl of 60% PEG 4000-10 mM HEPES-10 mM $CaCl_2$ solution for 30 minutes. Three ml of SPTC (40% PEG 4000, 0.8 M sorbitol, 0.05 M Tris pH 8.0, 0.05 M $CaCl_2$) were added and the protoplasts were plated directly onto COVE transformation plates (per liter: 0.52 g of KCl, 0.52 g of $MgSO_4$-$7H_2O$, 1.52 g of $KH2PO_4$, 1 ml of trace metals solution as described in Example 7, 342.3 g of sucrose, 25 g of Noble agar, 10 ml of 1 M acetamide, and 10 ml of 3 M CsCl) for amdS transformations. Plates were incubated 5–7 days at 34° C. Transformants were transferred to plates of the same medium and incubated 3–5 days at 34° C. The transformants were then purified by streaking spores and picking isolated colonies using the same plates under the same conditions.

EXAMPLE 9

Peroxidase production by hemA transformants

The transformants from Example 8 were inoculated into individual wells at approximately $1 \times 10^5$ spores per well of a 24-well microtiter plate containing 1 ml of quarter strength MY25 medium composed of 0.25% yeast extract, 0.63% maltose, and 0.05% urea pH 6.5, and 1xMY salts (see Example 7). The microtiter plates were incubated at 34° C. and 100 rpm in a humidity chamber for 5 days.

Peroxidase production levels were determined using the enzyme assay described in Example 7. The results of the microtiter plate tests demonstrate that the average POXU/ml of hemA transformants was 1.4-fold greater than the average of the vector only transformants, with the best hemA transformant showing a 1.6-fold increase in peroxidase production.

A minority (39%) of the hemA transformants show peroxidase levels similar to the majority of the vector only controls. PCR amplification using 50 ng of genomic DNA isolated as described in Example 1 from each transformant was performed as described in Example 2 except the primers hemA3' (see Example 4) and primer 5'-TCTCTTCCTTCCTGAATCCTC-3' (SEQ ID NO: 17) were used. This analysis showed that the hemA transformants contain the expression cassette.

Eleven of the best hemA transformants obtained above were cultivated in shake flasks to better evaluate the effects on peroxidase production. For shake flask evaluations, approximately $5 \times 10^6$ spores of each transformant were inoculated into 25 ml of MY25 medium containing 1% yeast extract, 2.5% maltose, 0.2% urea, and IX MY salts pH 6.5 (see Example 7). The shake flasks were incubated at 34° C. and 200 rpm for 7 to 8 days. Peroxidase assays were performed as described above.

The results demonstrated that five transformants, SEO1-15, SEO1-20, SEO1-26, SE01-28 and SEO1-32, produced peroxidase levels which were greater than the vector alone control strains, with three transformants expressing peroxidase at a level 1.9-fold greater than the average control peroxidase levels. The remaining six hemA transformants showed peroxidase levels which were comparable to control levels.

Transformant SEO1-28 and a control strain SE05-18 (pBANe6 vector alone transformant) were grown in 2 liter fermentations using a standard fed-batch protocol which has high maltose syrup as carbon source. The batch and feed were supplemented with $FeCl_3$ to approximately 0.4 mM. Positive dissolved oxygen tension was maintained in both cultures with feed added at a rate of approximately 2 grams saccharide per liter per hour from day three to day eight. This level was reached in a step-wise manner over days two and three. Biomass in both cultures were approximately equal for the duration of the fermentation.

A 2-fold increase in peroxidase activity was observed with SE01-28 over the control strain SE05-18. There was also a 2-fold increase in the polypeptide level for SE01-28 relative to the control strain SE05-18.

The overall results demonstrated that overexpression of the hemA gene resulted in a 2-fold increase in peroxidase yield. The data indicated further that hemA may represent a key regulatory point during heme biosynthesis in filamentous fungi which upon genetic manipulation can improve hemoprotein production in the absence of hemin supplementation.

EXAMPLE 10

Generation of a genomic hemB probe by PCR

Degenerate PCR primers were designed based on the amino acid sequence flanking a 126 bp hemB fragment from *Aspergillus oryzae* (Jesper Vind, 1994, Ph.D. Dissertation, University of Copenhagen, Copenhagen, Denmark) and the homologous regions of yeast and human hemB clones (Myers et al., 1987, *Journal of Biological Chemistry* 262:16822–16829; Wetmur et al., 1986, *Proceedings of the National Academy of Sciences USA* 83:7703–7707). The oligonucleotide primers were synthesized using an Applied Biosystems Model 394 DNA/RNA Synthesizer. Sense, 5'-GT(AGCT)GC(AGCT)CC(AGCT)(AT)(CG)(AGCT)GA(CT)ATGATGGA-3' (SEQ ID NO: 18) and antisense 5'-GC(AG)TC(AGCT)CG/T(AG)AA(AGCT)CC(AG)TA-3' (SEQ ID NO:19) primers were used to PCR amplify the hemB fragment using pJVi 60 (Vind, 1994, supra) as a template. The PCR reaction (50 µl) was composed of 10 mM Tris-HCl pH 8.3, 50 mM KCl, 1.5 mM $MgCl_2$, 0.01 % w/v gelatin, 200 µM each of dATP, dCTP, dGTP, and dTTP, 500 ng of pJVi 60, and 50 pmol of each PCR primer described above. The reaction was incubated at 95° C. for 3 minutes and cooled to 80° C. Then 5 units of Taq polymerase were added. The reaction was incubated in a Perkin-Elmer 9600 Thermal Cycler programmed for 35 cycles each at 95° C. for 30 seconds, 45° C. for 1 minute, and 72° C. for 1 minute. Following the last cycle the reaction was incubated at 72° C. for 5 minutes. A predicted 126 bp hemB PCR product was cloned into a pCRII vector to produce plasmid pAJ005-1 (FIG. 11).

EXAMPLE 11

*Aspergillus oryzae* strain A1560 DNA libraries and identification of porphobilinogen synthase (hemB) clones

*Aspergillus oryzae* strain A1560 genomic DNA libraries were constructed as described in Example 3.

Bacteriophage DNA from approximately 8×10⁴ plaques was transferred to duplicate circular Nytran Plus membranes (Schleicher & Schuell, Keene, N.H.) and probed with a ³²P-labeled PCR product derived by amplifying the hemB fragment of pAJO05-1 (see Example 10) according to Mertz and Rashtchian (1994, *Analytical Biochemistry* 221:160–165). The amplification reaction (50 μl) contained the following components: 10 mM Tris-HCl pH 8.3, 50 mM KCl, 1.5 mM MgCl2, 0.01 % (w/v) gelatin, 0.04 mM each of dATP, dCTP, dGTP, and dTTP, 5 μl of ³²P-dCTP (3000 Ci/mmole, 3.3 μM; Amersham, Arlington Heights, Ill.), and 50 pmole each of sense primer 5'-GTGGCTCCGAGTGATAT-3' (SEQ ID NO:20) and antisense primer 5'-GCATCGCGAAAAGGACCG-3' (SEQ ID NO:21). The reaction was heated to 95° C. for 3 minutes followed by the addition of 5 units of Taq polymerase. The reaction was then incubated in a Perkin-Elmer Thermal Cycler programmed for 30 cycles, each cycle at 95° C. for 1 minute, 55° C. for 1 minute, and 72° C. for 1 minute. The reaction solution was passed through a Sephadex G50 column (Pharmacia, Alameda, Calif.) to remove unincorporated nucleotides and then denatured and added to the hybridization buffer. Denatured probe (10⁶ cpm/ml) was added to hybridization buffer and incubated overnight with prehybridized membranes. Prehybridization and hybridization was conducted at 42° C. in 5×SSC, 50 mM sodium phosphate pH 7, 5×Denhardt's solution, 0.1 % (w/v) SDS, 5 mM EDTA pH 8, 10 μg/mL denatured salmon sperm DNA, and 50% formamide. Membranes were washed four times in 0.1×SSC, 0.1% SDS for 15 minutes at 42° C. Primary plaques that gave a positive signal were screened a second time and purified according to the manufacturer's instructions. Ten genomic clones that produced a positive signal were excised from the λZipLox vector as pZL derivatives according to the manufacturer's instructions (Bethesda Research Laboratories, Inc., Bethesda, Md.) and sequenced according to the method of Hattori and Sakaki (1986, *Analytical Biochemistry* 152:232–237). The pZL derivatives were designated pAJO07-1 through pAJO07-10. Clone *E. coli* DH5α pAJ007-6 contained a 3.7 kb genomic fragment based on restriction mapping and was further analyzed.

EXAMPLE 12

Characterization of the porphobilinogen synthase (hemB) gene

*E. coli* DH5α pAJ007-6 described in Example 11 was subjected to DNA sequencing according to the procedure described in Example 11.

The nucleotide sequence of the cloned *Aspergillus oryzae* A1560 hemB gene revealed an open reading frame of 1308 nucleotides as shown in FIG. 12 (SEQ ID NO:3) encoding a 374 amino acid polypeptide with a predicted molecular weight of 40 kDa as shown in FIG. 12 (SEQ ID NO:4). The nucleotide sequence contains one 48 bp putative intron which is flanked by splice site consensus sequences and contains an internal consensus sequence as predicted by (Unkles, 1992, in *Applied Molecular Genetics of Filamentous Fungi*, Chapter 2, J. R. Kinghorn and G. Turner, editors, Blackie Academic and Professional Publications). The 3' splice site (TAG) is located 254 bp downstream of the Met, a 5' splice site (GTCCGC) is located 46 bp upstream of the 3' splice site, and the internal consensus sequence (TCTAAC) is located 30 bp downstream of the 5' splice site. The 5' untranslated region contains two CAAT motifs at positions –377 and –233 and may play an important role in transcriptional regulation (Gurr et al., 1987, supra). In addition, several putative TATA like boxes are found in the 3' untranslated region (–117, –208, –650). As expected, hemB does not appear to contain a leader sequence at the N-terminus since it is cytoplasmic in other organisms except plants (Bottemley and Muller-Eberhard, 1988, *Seminars in Hematology* 25:282–302).

Amino acid alignment of the *Aspergillus oryzae* hemB gene (SEQ ID NO:4) to other hemB genes is shown in FIG. 13. The deduced hemB amino acid sequences from yeast (SEQ ID NO:31; Myers et al., 1987, supra), human (SEQ ID NO:27; Wetmur et al., 1986, supra), rat (SEQ ID NO:29; Bishop et al., 1989, *Nucleic Acids Research* 14:10115) and *E. coli* (SEQ ID NO:26; Li et al., 2989, *Gene* 75:177–184) have 63%, 55%, 55% and 40% identity, respectively to the *Aspergillus oryzae* hemB amino acid sequence. The deduced hemB amino acid sequences from pea (SEQ ID NO:28; Bsese et al., 1991, *Journal of Biological Chemistry* 266:17060–17066), *Bacillus subtilis* (SEQ ID NO:25; Hansson et al., 1991, *Journal of Bacteriology* 173:2590–2599) and spinach (SEQ ID NO:30; Scharmburg and Schneider-Poetsch, 1991, EMBL Data Library) are less similar (40%, 39% and 33% identity, respectively). However, since both the pea and spinach hemB amino acid sequences contain an N-terminal chloroplast signal sequence, their similarity to the *Aspergillus oryzae* hemB would significantly increase if they are aligned as mature polypeptides. Based on these alignments, the active lysine site of the *Aspergillus oryzae* hemB is located at amino acid 299 (Jaffe, 1995, *Journal of Bioenergetics and Biomembranes* 27:169–179) and a conserved zinc-finger like domain as predicted by Berg (1986, *Nature* 319:264–265) is located at amino acids 166–180. The zinc-finger has been suggested to prevent oxidation of the sulfhydryl groups at the active site by binding $Zn^{2+}$ (Jaffe, 1995, supra). The corresponding domain in plant hemB's is proposed to bind $Mg^{2+}$ rather than $Zn^{2+}$ (Bsese et al., 1991, supra). Interestingly, 2 5 the first residue of the hemB finger domain is a Thr (at position 166) which is conserved for this position in the plant metal-binding domain. However, the remaining positions in the hemB zinc finger domain are conserved.

EXAMPLE 13

Construction of pAJ023

Plasmid pAJ023 (FIG. 14) was constructed by PCR amplifying the *Aspergillus oryzae* hemB coding region and subcloning it into the *Aspergillus oryzae* expression vector pBANE6. The amplification product was designed to contain 5' SwaI and 3' PacI restriction sites to facilitate cloning into pBANe6. The amplification reaction (50 μl) contained the following components: 10 mM Tris-HCl pH 8.3, 50 mM KCl, 1.5 mM $MgCl_2$, 0.01% (w/v) gelatin, 200 μM each of dATP, dCTP, dGTP, and dTTP, 200 ng of pAJO07-6 DNA, and 50 pmol of each PCR primer shown below:

PBG10 (Sense): 5'-GCATATTTAAATGATGTC-CTTTTCTAATCTCGT-3' (SEQ ID NO:38)

PBG11A (Antisense): 5'- ATATTAATTAATCCATCTAGCTAAAT-CATT-3' (SEQ ID NO:39)

The underlined regions of PBG10 and PBG11A contained the cloning restriction sequences SwaI and PacI, respectively. The reaction was incubated at 95° C. for 3 minutes and cooled to 80° C. Five units of PWO (BM) polymerase were added. The reaction was incubated in a Perkin-Elmer 9600 Thermo-Cycler programmed for 30 cycles each at 95°

C. for 30 seconds, 57° C. for 1 minute, and 72° C. for 1 minute. Following the last cycle, the reaction was incubated at 72° C. for 5 minutes. The final PCR product was gel purified, digested with SwaI and PacI, and ligated into the vector pBANe6 which was digested with SwaI and PacI to create pAJ023.

EXAMPLE 14

Transformation of *Aspergillus oryzae* JRoC50.3.18A with pAJ023

*Aspergillus oryzae* strain JRoC50.3.18A was transformed with pAJ023 in order to determine whether overexpression of the *Aspergillus oryzae* hemB gene increased peroxidase production. As a control, pBANe6 was also used to transform *Aspergillus oryzae* JRoc 50.3.18A. The transformation was conducted with protoplasts at a concentration of $2 \times 10^7$ protoplasts per ml. One hundred µl of protoplasts were placed on ice with 10 µg DNA for 30 minutes. One ml of SPTC was added and the protoplasts were incubated at 34° C. for 20 minutes. Aliquots of 0.25 ml of the transformation were added to 15 ml of COVE agar overlay (see Example 8) prior to plating onto COVE transformation plates. Plates were incubated 5–7 days at room temperature. Transformants were transferred to plates of the same medium and incubated 3–5 days at 37° C.

EXAMPLE 15

Peroxidase production by hemB primary transformants

A total of 20 *Aspergillus* oryzae hemB transformants and 42 control transformants (transformants of JRoC 50.3.18A with the *Aspergillus oryzae* expression vector without *Aspergillus oryzae* hemB) were grown in 24 well plates and assayed for peroxidase production as described in Example 7.

The results of the peroxidase assays showed no increase in the number of transformants producing higher levels of peroxidase activity relative to the control transformants.

EXAMPLE 16

Construction of pSE37 and pSE38 pSE7t1 (FIG. 15) was constructed by ligation of a PCR amplified region of the *Aspergillus oryzae* A1560 hemA open reading frame into pCRII (Invitrogen, San Diego, CA) according to the manufacturer's instructions. The hemA open reading frame was PCR amplified using primers hemA5' (SEQ ID NO:7) and hemA3' (SEQ ID NO:8) described in Example 4 from pSE17 (Example 3) according the same PCR conditions described in Example 6 except the concentration of each dNTP was 50 µM. Plasmid pSE37 (FIG. 16) was constructed by ligating the 1940 bp SwaI-PacI fragment containing the hemA coding region from pSE7t1 into SwaI-PacI cut pSE39 (FIG. 17).

pSE39 was constructed by ligation of a blunted 2033 bp HindIII-EcoRI fragment from pMT1612 (FIG. 18) to a blunted NsiI fragment of pBANe13 (FIG. 19) which replaced the pyrG selectable marker with the bar selectable marker conferring resistance to Basta. Plasmid pSE38 (FIG. 20) was constructed by ligating a 1137 bp SwaI-PacI fragment containing the hemB open reading frame from pAJ23 (FIG. 14) into SwaI-PacI cut pSE39 (FIG. 17).

EXAMPLE 17

Effect of hemA and hemB co-overexpression on *Coprinus cinereus* peroxidase production.

*Aspergillus oryzae* strain SE01-28 described in Example 9 was transformed with pSE38 to create new transformants designated *Aspergillus oryzae* SE27 according to the method described in Example 8 with the exceptions that Basta resistance was used for selection and 2–8 µg of NdeI digested pSE38 was added per transformation directly from the reaction so that ~5 U of enzyme was included in the transformation mixture. Media for Basta selection contained 20 ml of COVE salts, 1 M sucrose, 25 g/L Noble agar, 10 mM Urea, and either 5 mg/ml Basta (Hoechst Schering, Rodovre, Denmark) for transformation or 10 mg/ml Basta for maintaining transformants. The COVE salts were composed of 26 g of KCl, 26 g of $MgSO_4$-$7H_2O$, 76 g of $KH_2PO_4$, and 50 ml of COVE trace elements per liter of deionized water. The COVE trace elements were composed of 0.04 g of $Na_2B_4O_7$-$10H_2O$, 0.4 g of $CuSO_4$-$5H_2O$, 1.2 g of $FeSO_4$-$7H_2O$, 0.7 g of $MnSO_4$-$H_2O$, 0.8 g of $Na_2MoO_2$-$H_2O$, 10 g of $ZnSO_4$-$7H_2O$ per liter of deionized water. Maltose was added to a final concentration of 2.5%, when indicated. Basta selection overlay medium was the same as above except that Basta was added prior to use.

Two control populations, a hema overexpression population (*Aspergillus oryzae* SE01-28 transformed with pSE39= *Aspergillus oryzae* SE28 strains) and a vector transformed population (*Aspergillus oryzae* JRoC50.3.18A transformed with pSE39 =*Aspergillus oryzae* SE22 strains) were also constructed using the same procedure described above.

The transformants were then inoculated into individual wells at approximately $1 \times 10^5$ spores per well of 24-well microtiter plates containing 1 ml of quarter strength MY25 medium. The microtiter plates were incubated at 34° C. and 100 rpm in a humidity chamber for 5 days. Peroxidase production levels were determined using the enzyme assay described in Example 7.

The results demonstrated a dramatic shift in the distribution of peroxidase activities toward higher levels with the population of *Aspergillus oryzae* SE27 strains when compared to the two control populations, the *Aspergillus oryzae* SE28 strains (hemA overexpression population) and the *Aspergillus oryzae* SE22 strains (a vector transformed population). The hemA/hemB co-overexpression strains showed approximately a 4-fold average increase over non-engineered strains (SE22) and a 1.8-fold average increase over hemA overexpression strains (SE28).

Several of the highest peroxidase producing transformants—*Aspergillus oryzae* transformants SE27-3, SE27-8, SE27-12 and SE27-13 - were then cultured in shake flasks. Approximately $5 \times 10^6$ spores were inoculated into 25 ml of MY25 medium and incubated at 34° C., 200 rpm for 5 days. Alternatively, a mycelial plug was inoculated into a flask containing 25 ml of MY25 medium and 0.002% Novozyme 234 and incubated for 2 days at 34° C., 200 rpm. Four mls of this culture were used to inoculate triplicate shake flasks containing 25 ml of MY25 medium for incubation at 34° C., 200 rpm for 5 days. Samples were then removed and filtered through Miracloth to remove mycelial fragments before enzyme assay for peroxidase activity.

Peroxidase assays of the shake flask cultures of *Aspergillus oryzae* transformants SE27-3, SE27-8, SE27-12 and SE27-13 showed that all produced higher peroxidase activity when compared to control strains *Aspergillus oryzae* SE22 and SE28. Strains SE27-12 and SE27-8 showed a 4-fold increase over the SE22 control strains and a 2-fold increase over the SE28 control strains.

*Aspergillus oryzae* SE27-12 and *Aspergillus oryzae* SE22 as a control were grown in 2 liter fermentations with and without the addition of hemoglobin using a standard fed-batch protocol which had high maltose syrup as carbon source. The batch and feed were supplemented with $FeCl_3$ to approximately 0.4 mM. Positive dissolved oxygen tension was maintained in both cultures with feed added at a rate of approximately 2 grams saccharide per liter per hour from day three to day eight. This level was reached in a step-wise manner over days two and three. Biomass in both cultures were approximately equal for the duration of the fermentation. Fermentations were also run in the presence of hemoglobin. Hemoglobin was added to a final concentration of 30 mg/ml of batch medium.

The results showed that there was a 6-fold increase in peroxidase production over SE22 after 192 hours of a fermentation. An additional 3-fold increase in peroxidase production from SE27-12 compared to SE22 was observed when hemoglobin was added to the fermentation medium. The total increase in peroxidase yield using a hemA/hemB engineered strain grown in the presence of hemoglobin compared to a non-engineered strain with no added hemoglobin was 10-fold.

These results indicated that overexpression of hemA and hemB synergistically improved peroxidase production.

EXAMPLE 18

Effect of hemA/hemB co-overexpression on Scytalidium thermophilum catalase production

*Aspergillus oryzae* strain HowB411 containing a *Scytalidium thermophilum* catalase gene (WO 96134962) and designated DLM 14.24 was engineered to co-overexpress hemA and hemB in order to determine whether co-overexpression would increase catalase production. *Aspergillus oryzae* strain DLM14.24 was co-transformed under the same conditions described in Example 17 with 10 μg each of pSE37 and pSE38 to create transformants designated *Aspergillus oryzae* SE32. Control strains, designated *Aspergillus oryzae* SE24, were generated by transformation of *Aspergillus oryzae* DLM14.24 with pSE39 under the same conditions described in Example 17.

The SE32 transformants and control strains were inoculated into individual wells at approximately $1 \times 10^5$ spores per well of a 24-well microtiter plate containing 1 ml of M400Da pH 6.0 medium composed of 50 g of maltodextrin, 2 g of $MgSO_4\text{-}7H_2O$, 2 g of $KH_2PO_4$, 4 g of citric acid, 8 g of yeast extract, 2 g of urea, 0.5 g of $CaCl_2\text{-}2H_2O$, and 1 ml of trace elements per liter. The trace metals solution was composed of 13.9 g of $FeSO_4\text{-}7H_2O$, 8.5 g of $MnSO_4\text{-}H_2O$, 14.28 g of $ZnSO_4\text{-}7H_2O$, 1.63 g of $CuSO_4$, 0.24 g of $NiCl_2\text{-}6H_2O$, and 3.0 g of citric acid per liter. The microtiter plates were incubated at 34° C. and 100 rpm in a humidity chamber for 5 days. Catalase production levels were determined using the enzyme assay described in WO 96/34962. A CIU is defined as the amount of catalase which decomposes one micromole of hydrogen peroxide per minute in 12 mM hydrogen peroxide-50 mM potassium phosphate pH 7.0 buffer at 25° C.

The population of *Aspergillus oryzae* SE32 hemA/hemB co-transformants initially analyzed showed a catalase distribution which was slightly shifted toward higher catalase production. The average CIU/ml of the co-transformant population was 1.3-fold higher than the average CIU/ml of the control population.

The best *Aspergillus oryzae* co-transformants SE32-3a, SE32-4a, SE32-6b, and SE32-32a were then grown in shake flasks containing 25 ml of M400Da medium at 34° C. and 200 rpm for 6 days and assayed for catalase activity as described earlier.

The best strain, *Aspergillus oryzae* SE32-32a, showed a 1.8-fold increase in catalase production compared to the control strains.

EXAMPLE 19

Construction of Aspergillus oryzae HowB430 pBANe8 was constructed to contain the TAKA/NA2-tpi leader hybrid promoter, the Lipolase™ gene, the AMG terminator, and a full-length *Aspergillus nidulans* amdS gene as a selectable marker. Lipolase™ (Novo Nordisk A/S, Bagsværd, Denmark) is a lipase from *Humicola lanuginosus*.

PCR was used to insert desired restriction sites using primers 1–4 described below synthesized with an Applied Biosystems Model 394 DNA/RNA Synthesizer, according to the manufacturer's instructions.

Primer 1: 5'-ATGCATCTGGAAACGCAACCCTGA-3' (SEQ ID NO:32)

Primer 2: 5'-ATGCATTCTACGCCAGGACCGAGC-3' (SEQ ID NO:33)

Primer 3: 5'-TGGTGTACAGGGGCATAAAAT-3' (SEQ ID NO:34)

Primer 4: 5'-ATTTAAATCCAGTTGTGTATATAGAG-GATTGTGG-3' (SEQ ID NO:35)

Amplification reactions (100 μl) were prepared using approximately 0.2 μg of one of the following plasmids as a template: pToC90 plasmid DNA (Christensen et al., 1988, *Biotechnology* 6:1419–1422) was used as template with primers 1 and 2 to insert NsiI flanking sites on the full-length amdS gene. pJaL292 plasmid DNA (FIG. 21) was used as template with primers 3 and 4 to insert an EcoRI site at the 5' end and a SwaI site at the 3' end of the NA2-tpi leader hybrid promoter. Each reaction contained the following components: 0.2 μg of plasmid DNA, 48.4 pmol of the forward primer, 48.4 pmol of the reverse primer, 1 μM each of dATP, dCTP, dGTP, and dTTP, 1 x Taq polymerase buffer, and 2.5 U of Taq polymerase. The reactions were incubated in an Ericomp Thermal Cycler programmed for one cycle at 95° C. for 5 minutes followed by 30 cycles at 95° C. for 1 minute, 55° C. for 1 minute, and 72° C. for 2 minutes.

The PCR products were subsequently subcloned into pCRII using the TA Cloning Kit (Invitrogen, San Diego, Calif.) according to the manufacturer's instructions. The transformants were then screened by extracting plasmid DNA from the transformants using a QIAwell-8 Plasmid Kit (Qiagen, Inc., Chatsworth, Calif.) according to the manufacturer's instructions, restriction digesting the plasmid DNA to confirm the presence of the correct size fragment, and sequencing the DNA according to the following method to confirm the PCR product. DNA sequencing was performed with an Applied Biosystems Model 373A Automated DNA Sequencer on both strands using the primer walking technique with dye-terminator chemistry (Giesecke et al., 1992, supra) using the M13 reverse (−48) and M13 forward (−20) primers (New England Biolabs, Beverly, Mass.) and primers unique to the DNA being sequenced. The plasmids from the correct transformants were then digested with the restriction enzymes for which they were designed, separated on a 1 % agarose gel, and purified using a FMC SpinBind Kit (FMC, Rockland, ME) according to the manufacturer's instructions.

The NA2-tpi leader was PCR amplified from pJaL292 (FIG. 21) with EcoRI and SwaI restriction sites placed on the ends. pKS6 (FIG. 22), which contains the TAKA promoter, a polylinker, AMG terminator and the *Aspergillus nidulans* pyrG gene, was digested with EcoRI and SwaI to remove a portion of the TAKA promoter. This region was replaced with the NA2-tpi PCR product to produce pBANel3 (FIG. 19).

The full length amdS gene was PCR amplified with NsiI sites at both ends. pBANe13 was digested with NsiI to remove the Aspergillus nidulans pyrG gene. This region was replaced with the full length amdS gene to produce pBANe6 (FIG. 6).

The oligonucleotide primers 5 and 6 shown below were synthesized using an Applied Biosystems Model 394 DNA/RNA Synthesizer, according to the manufacturer's instructions, for inserting restriction sites flanking the lipase gene by PCR amplification:

Primer 5: 5'-ATTTAAATGATGAGGAGCTCCCTTGTGCTG-3' (SEQ ID NO:36)

Primer 6: 5'-TTAATTAACTAGAGTCGACCCAGCCGCGC-3' (SEQ ID NO:37)

The amplification reaction (100 μl) was prepared using approximately 0.2 mg of pMHan37 (FIG. 23) as a template with primers 5 and 6. The reaction contained the following components: 0.2 μg of pMHan37, 48.4 pmol of primer 5, 48.4 pmol of primer 6, 1 μM each of dATP, dCTP, dGTP, and dTTP, 1 x Taq polymerase buffer, and 2.5 U of Taq polymerase. The reaction was incubated in an Ericomp Thermal Cycler programmed for one cycle at 95° C. for 5 minutes followed by 30 cycles at 95° C. for 1 minute, 55° C. for 1 minute, and 72° C. for 2 minutes. Two ml of the reaction was electrophoresed on an agarose gel to confirm the amplification of the lipase product of approximately 900 bp.

The PCR amplified lipase gene was subcloned into pCRII using the TA Cloning Kit according to the manufacturer's instructions. The transformants were then screened by extracting plasmid DNA from the transformants using a QIAwell-8 Plasmid Kit according to the manufacturer's instructions, restriction digesting the plasmid DNA, and sequencing the DNA according to the method above to confirm the PCR product.

The lipase gene was excised from pCRII by digesting with SwaI and PacI and was subsequently subcloned into pBANe6 to obtain pBANe8 (FIG. 24). Transformants were screened by extracting plasmid DNA from the transformants using a QIAwell-8 Plasmid Kit according to the manufacturer's instructions, restriction digesting the plasmid DNA, and sequencing the DNA according to the method described above to confirm the product.

*Aspergillus oryzae* HowB430 was generated by transformation of Aspergillus oryzae HowB425 with a linear fragment containing the NA2-tpi promoter/Lipolase™ gene/AMG terminator designated pBANe8. pBANe8 was digested with PmeI and the linear expression cassette was isolated by preparative agarose electrophoresis using 40 mM Tris-acetate-1 mM disodium EDTA (TAE) buffer.

Transformation of Aspergillus oryzae HowB425 for amdS was conducted with protoplasts at a concentration of $2\times10^7$ protoplasts per ml. Ten μg of DNA were added to 100 μl of protoplasts. A volume of 250 μl of PEG (60% PEG 4000-10 mM $CaCl_2$-10 mM Tris-HCl pH 8.0) was then added and the mixture was placed at 37° C. for 30 minutes. Three ml of STC medium was added and the mixture was plated on COVE plates supplemented with 10 mM uridine selecting for amdS. The plates were incubated 7–10 days at 34° C. Transformants were transferred to plates of the same medium and incubated 3–5 days at 37° C. The transformants were purified by streaking spores and picking isolated colonies using the same plates of the same medium without sucrose under the same conditions.

EXAMPLE 20

Specificity of hemA/hemB co-overexpression on hemoprotein production

Since heme is involved in providing energy for cell growth and metabolism, it was important to show that increased hemoprotein production was due to increased availability of heme for association with apo-enzyme, not simple increased apo-protein production due to enhanced cell metabolism and growth. An indirect method for testing this hypothesis was to co-overexpress hemA and hemB in a strain producing a heterologous enzyme that was not a hemoprotein, i.e., a lipase. If enhanced energy availability were the cause of increased hemoprotein production, then a similar result should be observed on lipase expression. Conversely, if increased hemoprotein production is specifically due to the increased availability of heme for mature enzyme assembly, then little effect on lipase expression should be observed.

*Aspergillus oryzae* strain HowB430 described in Example 19 was co-transformed with pSE37 and pSE38 as described in Example 18 to generate a non-hemoprotein hemA/hemB co-overexpression strain, Aspergillus oryzae strain SE33. Again, control transformants, designated SE34, were generated by transformation of the same strain with pSE39.

The transformants were inoculated into individual wells at approximately $1\times10^5$ spores per well of a 24-well microtiter plate containing 1 ml of quarter strength MY25 medium. The microtiter plates were incubated at 34° C. and 100 rpm in a humidity chamber for 4 days. Lipase production levels were determined according to the following method relative to a Lipolase™ standard (Novo Nordisk A/S, Bagsværd, Denmark). The assay substrate was prepared by diluting 1:50 stock substrate (21 μl of p-nitrophenylbutyrate/ml DMSO) into MC buffer (4 mM $CaCl_2$-100 mM MOPS pH 7.5) immediately before use. The Lipolase™ standard was prepared to contain 40 LU/ml in MC buffer plus 0.02% alpha olefin sulfonate (AOS) detergent, was stored at 4° C. and then diluted 1/20 in MC buffer just before use. Broth samples were diluted in MC buffer containing 0.02% AOS detergent and 20 μl aliquots were dispensed to wells in 96-well plates followed by 200 ml of diluted substrate. Using a plate reader, the absorbance at 405 nm was recorded as the difference of two readings taken at approximately 1 minute intervals. Lipase units/ml (LU/ml) were calculated relative to the Lipolase™ standard.

The results of the lipase assays showed that the hemA/hemB co-transformants as a population produced 1.25-fold more lipase compared to the control transformant population. The slight, but significant, difference of the lipolase hemA/hemB co-overexpression population versus the control population may be due to a small effect of increased heme availability on cell growth and metabolism.

EXAMPLE 21

Effect of hemA/hemB co-overexpression on accumulation of heme pathway intermediates.

Both the mycelia and culture broths of the majority of the *Aspergillus oryzae* SE27 strains grown in 24-well plates described in Example 17 appeared pink or red in color.

Filtration of an *Aspergillus oryzae* SE27 strain culture broth using a Centricon 10 column (Amicon, Beverly, Mass.) showed that the red color was in the filtrate suggesting that the color was due to a small molecule. The filtrate was observed to absorb light at a wavelength of 405 mn which is consistent with porphyrins.

In order to confirm that the red color in the *Aspergillus oryzae* SE27 culture broths was due to the presence of one or more porphyrins involved in heme biosynthesis, culture broths were analyzed by HPLC according to the method described by C. A. Burtis and E. R. Ashwood (editors) In the Tietz Textbook of Clinical Chemistry, 1994, Chapter 38. HPLC analysis demonstrated that the culture broth contained elevated levels of compounds with the same retention time as uroporphyrin (uro), hepta-, hexa-, and pentacarboxylated porphyrins and coproporphyrin (copro). Broths from control strains Aspergillus oryzae SE36 (*Aspergillus oryzae* transformed with pSE39) showed little accumulation of these intermediates. The ratio of uroporphyrin compounds to coproporphyrin was at least 3:1 in all hemA/hemB co-overexpression strains.

Each of the hemA/hemB co-overexpression strains also showed high levels of fluorescence characteristic of porphyrin compounds while the control strain showed no fluorescence. Fluorescence microscopy of mycelia (excitation at 420–450, barrier filter at 520) from strain SE27-3 showed distinct patches and granules of fluorescence which were not present in control strains SE28-1 or 22-1. These results suggested that hemA/hemB co-overexpression strains produced large amounts of uroporphyrin.

The accumulation of these intermediates may result from uroporphyrinogen III decarboxylase (Uro D) becoming a rate-limiting step in the biosynthesis of heme.

EXAMPLE 22

Southern analysis of *Aspergillus oryzae* strains SE27 and SE32

Southern analysis of *Aspergillus oryzae* strains SE27 and SE32 was performed to determine whether production of the red color by hemoprotein producing strains required multiple copies of both hemA and hemB expression cassettes.

Total cellular DNA for each strain prepared as described in Example 1 was analyzed by Southern hybridization (Maniatis et al., 1982, *Molecular Cloning, a Laboratory Manual*, Cold Spring Harbor Press, Cold Spring Harbor, N.Y.). Approximately 10 μg of each DNA sample were digested with PstI or PvuI and fractionated by size on a 1% agarose gel. The gel was photographed under short wavelength UV light and soaked for 30 minutes in 0.25 N HCl followed by 30 minutes in 0.4 N NaOH. DNA in the gel was transferred onto a Hybond N hybridization membrane (Amersham, Arlington Heights, Ill.) by capillary blotting in 0.4 N NaOH using a Turbo blot apparatus (Schleicher & Schleicher, Keene, N.H.) according to the manufacturer's instructions. The membrane was UV crosslinked and was prehybridized as described in Example 4 except a 5% Vistra Liquid blocking agent (Amersham, Arlington Heights, Ill.) was used in place of the Genius blocking agent. A fluorescent-labelled probe was prepared by random-priming the DNA fragment described in Example 3 using a Vistra Kit (Amersham, Arlington Heights, Ill.). The hybridization and wash steps were performed as described in Example 4. The signal of the fluorescent probe was amplified using the Vistra Kit according to the manufacturer's instructions. Fluorescence was detected by scanning on a Storm Imaging System (Molecular Dynamics, Sunnyvale, Calif.).

Southern blot analysis of Aspergillus oryzae strains SE27 and SE32 showed that multiple copies of both expression plasmids, pSE37 and pSE38, were present and that production of the red color required the presence of both expression cassettes.

DEPOSIT OF MICROORGANISMS

The following strains have been deposited according to the Budapest Treaty in the Agricultural Research Service Patent Culture Collection (NRRL), Northern Regional Research Laboratory, 1815 University Street, Peoria, Ill. 61604, USA.

| Strain | Accession Number | Deposit Date |
| --- | --- | --- |
| *E. coli* DH5α (pSE17) | NNRL B-21563 | April 22, 1996 |
| *E. coli* DH5α (pAJ007-6) | NRRL B-21564 | April 22, 1996 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposits represent a substantially pure culture of each deposited strain. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
        (A) LENGTH: 4157 base pairs
        (B) TYPE: nucleic acid
        (C) STRANDEDNESS: single
        (D) TOPOLOGY: linear (xi) SEQUENCE DESCRIPTION: SEQ ID NO:1:

```
ACCATTGACT CTCAAGCTAT GGATCGTGCT CACCGTCTCG GCCAGACAAG ACAGGTCACG      60

GTGTATCGCC TGATTACTCG CGGCACCATT GAGGAGCGTA TTCGCAAGCG AGCTTTGCAG     120

AAGGAGGAAG TGCAGCGTGT CGTCATCTCA GGTGGCGCAG CTGGTGGGGT TGACTTCAAT     180

ACTCGCAACC GCGAGAGCCG AACCAAGGAC ATCGCCATGT GGCTGGCAGA TGATGAACAG     240

GCGGAGCTTA TTGAGCAAAA GGAGAAGGAA GCGCTGGACC GAGGCGAAGT GTTTGGCGCT     300

AGTAAAGGCG GGAAGAAGGC TGCTCAGAAG AGAAAGAGAG ATATCACGCT GGATGATATG     360

TATCATGAAG GTATGTGAAT CTGATCAAAG CTCTTCGTTC CGGGGAGGCT TCTGGAAATA     420

GTACTAACCG CGTCAATCTA TAGGCGAAGG GAACTTTGAC GATGCCAGTG CAAAGCCATC     480

AGGAGCGGCC ACTCCTGTGT CGACTGCAGA GAATTTAGGC ACCCCATCCT CCACGCCAGT     540

TCCTAAACGA GGACGTGGAA GGGGGACAGG AAAGGGCACG TCTAAAAGAG CCAAAACTAC     600

CAAGGAGAGA TTACGTCTCA TTGATGGCGA CGGAGGCTTA GGGCCTAGTT GATTTAATCG     660

ATCTGTGCCT CAATAATGGA CACGGCTGGT TATGGTCATG GCGTTCAGAG ATTGCATTTC     720

TTTCCCACCC TTTATCTTTC TTTCTTTCCT CTTAAACCCC TCTTTTTTGT TTTTCTTTTT     780

ATCGGACTTT ACTTGTGGGC AGCTTACGTT CTGCCTTGTA TTAACAGCAT ATATTCCTGA     840

TTCCTGATGT ACGAAGCGAT TTAAGAGTCA TTGAAGACGA AGGATGAAAC CCGTGGTAAT     900

CAGCCGATAA TGGCAAAGAG AAGGAGAAGA AAAAAATCAA GTGCGAGTTT TGAAATTGAT     960

GGCAAGATAG ACATTGTATC CTGTACCTGT TCTTGGGCTG TGACGGGGGG GGTGAAATTG    1020

ACGGTCATCA CCCGGCTATT ATTACTATTG TTGTACTGTA CATCCGGATC CTGCTGGTCT    1080

GTATCTAGTT AGGGCAATAT TCCCCGTCGC CAGGCCTCTT GGGTTATGAA TGATTTCATA    1140

GGTGAAGTTT CGTATCCGTA CGCACCGAGA GATTTCTTAG TATTACTTGT ATTATGAAAA    1200

TGCACTTGCC GAGTTAAGTC CGCCGGCCAA TCACGGCGGA GGATATGGTA AGCCGAAAAG    1260

TCTCGCCGAA GTCCCCGACT TACTCTTACT GGAAGTGGCT TAGTGCCCTC AGCGCCCCCT    1320

CGCCCTCAGT CCATCAGCCA GATTGACTCT TATTTCTCTC TCCTCTTCGC CGCGGGTGAC    1380

ATATCCCTCT CCTTCTCCCT CTCCCTCTTG ACAACATTTC ATCTTCGCTT CCTTTTGTGA    1440

TATAGTCAGT TTCGCTATCC ATTGAAGCAT CACTCATGGA GTCTCTTCTC CAGCAGTCCC    1500

GGGCGATGTG CCCGTTCCTT AAGCGCACAT CTCCATCTTC TCTGCGTACG CTGGCAACCG    1560

CGACTCGACC TAGCACTAGT TCCGGTGGAG GCACTATGTC TAATCTCCAG GTCATTGCCC    1620

GTCGCTGCCC TGTCATGAGC AAGGCTCTGG CCGTGCAGAG CGCTCGCATG GCCGGTACCA    1680

AAAGATTCAC CTCATGTGCT GCCGGCATCA CCGGTCTCGG CAACAAGCAT TGCCGTGCTC    1740

CTACTGGGAA GAGAACCCTG CACTCCACCT CCGGTAACGG CGCCAATGTG AGCGCAGAGA    1800

TCTACAAGAA CACCCAGCGA GATCCCGCCG GTTTCTGAA GATCAAGACC CCTGCCAATG    1860

CTACCGCCGC TGCCGCTACG TCTGGCCCTC GTCCAGAGGC TCCCGTGGCG AAGCCTTTCA    1920

ACTACAATTC TTTCTACAAC ACCGAATTGG AAAAGAAACA CAAGGACAAG TCGTATCGCT    1980

ATTTCAACAA CATCAATCGT CTCGCTCAGG AGTTTCCCCG GGCTCACACC ACATCTGCCG    2040
```

-continued

```
AGGAACGTGT GACGGTCTGG TGCTCGAACG ATTATCTCGG CATGGGCCGC AACCCCGAGG    2100

TTCTGGCCAC CATGCATAAG ACATTGGACA CCTACGGAGC CGGTGCGGGA GGTACTCGCA    2160

ACATTTCAGG TCACAATCAA CATGCCGTGA GCCTGGAGAA CACCCTGGCC AAATTGCACG    2220

GCAAGGAGGC GGCATTAGTC TTCAGCTCAT GCTTCGTGGC TAACGATGCC ACCCTCGCAA    2280

CCCTGGGTAG CAAGTTGCCC GACTGTGTTA TTCTGTCCGA TAGCCTGAAT CATGCATCGA    2340

TGATTCAGGG TATTCGCCAT TCAGGCGCCA AGAAAATGGT TTTCAAGCAT AATGATCTGG    2400

TCGACCTTGA GGCCAAGTTG GCAGCTCTAC CTCTTCATGT CCCCAAGATT ATTGCATTCG    2460

AATCAGTTTA TAGCATGTGC GGATCTATTG CCCCAATTGA GAAGATCTGT GATCTTGCAG    2520

ACAAGTACGG TGCCATTACT TTCCTGGATG AAGTCCACGC TGTGGGAATG TACGGACCTC    2580

ACGGAGCAGG TGTGGCAGAG CACCTTGACT ATGACATCTA TGCTTCCCAA GATACGGTCA    2640

ACCCGCGCAG TACTAAGGGA ACCGTGATGG ACCGAATCGA TATTATCACC GGTACTCTGG    2700

GCAAGGCCTA CGGATGTGTC GGGGGCTACA TTGCTGGATC CGCTGCGATG GTTGACACCA    2760

TCCGCTCCCT CGCCCCTGGC TTCATCTTCA CCACGTCCTT GCCGCCCGCC ACCATGGCTG    2820

GTGCAGACAC TGCTATCCAG TACCAGGCTC GTCACCAGGG CGACCGCGTC CTGCAGCAGT    2880

TGCACACCCG CGCGGTCAAA GCAGCTTTCA GGAGTTGGA TATTCCTGTA ATTCCCAACC     2940

CCTCCCATAT CATTCCGCTC CTGGTTGGGG ATGCCGAGGT TGCTAAGAAG GCCTCGGACA    3000

AGCTTCTGGA GGAGCATGGA ATTTATGTAC AAGCCATCAA CTACCCAACC GTGCCTCGGG    3060

GTGAAGAGCG GCTTCGTATC ACGCCCACCC CGGGACATAT CAAGGAGCAC CGCGACCACC    3120

TGGTGCAAGC CGTCCAAACA GTCTGGAACG AACTGGGCAT CAAACGCACC AGCGATTGGG    3180

AAGCGCAAGG CGGCTTCGTC GGCGTGGGTG TCGATGGCGC CGAGGCTGAG AACCAGCCGA    3240

TTTGGAATGA TGTGCAGCTG GGGCTGAAGG AAAACGAAGC CATTGAGGCT GCTGTGGAAC    3300

GCGAGTTTGC CGAGGCCCCC ATGCGGACCG CCACCCGTCC TGCCGCGGCT GCTGCTTCGT    3360

CAATCCCGGT GGGTGTGGCT GCCTGAAGTG GCTGCCCGCA TGTGAGCTGA AATCGACGTG    3420

GAATTCTATA CACACACACA CACACACACA CACACACACA CACACACACA CACACACACA    3480

CACACACACA CACACACACT AACACACACT ATGTTATAAA TTCCACATCC ACTCCTTTGT    3540

CCCTTGTTGG ACGTAATTGG TATTTGGACT ATTAGTTAGA ACCAGTCAGT CGTTACCATG    3600

TGTTTCGGTT CGACTCGAAA TCTGACATGT TGTCTGCCCC CATGCCACTT CATCTCCTCC    3660

GTAACCGCAG GGCTTCAAAT ACACTGCCCA GTAATTGTAG TCAATATAGC AGTTAACTAA    3720

CCTTCACCAA TTTCCTAATA ACAATAGAAG GGGCCATACA CGCAGTACCA AAGATCACCT    3780

ACCTCCGATC AATATCCGAA CCTCAGGCTA CATACATCAA GTCGCATTAA TCGATTCCGA    3840

CCTCTGTTTA TCCCTGAAAA TAACTAAGAT CATGATCTAC GTTTGGTAAG TGGGACACCT    3900

ACCTACACTG GGAGGTATTG AATAAAGGCA TCATTCATAT AGTCACAAGA TGCCAGGGCC    3960

AATTCATGAT ATGGATAGCT ACTTCCAAAC ATAATTCAGA GGTATCATTC TGCTCTTCAG    4020

ACAGTTCTTC TCGAAGATCA GTAGGAGCCA GTTTTGACCA TTAACTTGTA ATGTAATTGC    4080

GATTGTAGTA GATCCGAGAT CCATTCACTT TCTAAGGGTT AATTGATTCA TTTTACTGAT    4140

ACCTCACCCA CCATATT                                                   4157
```

(2) INFORMATION FOR SEQ ID NO:2:

(i) SEQUENCE CHARACTERISTICS:
        (A) LENGTH: 636 amino acids
        (B) TYPE: amino acid

```
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Glu Ser Leu Leu Gln Gln Ser Arg Ala Met Cys Pro Phe Leu Lys
  1               5                  10                  15

Arg Thr Ser Pro Ser Ser Leu Arg Thr Leu Ala Thr Ala Thr Arg Pro
             20                  25                  30

Ser Thr Ser Ser Gly Gly Gly Thr Met Ser Asn Leu Gln Val Ile Ala
         35                  40                  45

Arg Arg Cys Pro Val Met Ser Lys Ala Leu Ala Val Gln Ser Ala Arg
     50                  55                  60

Met Ala Gly Thr Lys Arg Phe Thr Ser Cys Ala Ala Gly Ile Thr Gly
 65                  70                  75                  80

Leu Gly Asn Lys His Cys Arg Ala Pro Thr Gly Lys Arg Thr Leu His
                 85                  90                  95

Ser Thr Ser Gly Asn Gly Ala Asn Val Ser Ala Glu Ile Tyr Lys Asn
            100                 105                 110

Thr Gln Arg Asp Pro Ala Gly Phe Ser Lys Ile Lys Thr Pro Ala Asn
            115                 120                 125

Ala Thr Ala Ala Ala Thr Ser Gly Pro Arg Pro Glu Ala Pro Val
        130                 135                 140

Ala Lys Pro Phe Asn Tyr Asn Ser Phe Tyr Asn Thr Glu Leu Glu Lys
145                 150                 155                 160

Lys His Lys Asp Lys Ser Tyr Arg Tyr Phe Asn Asn Ile Asn Arg Leu
                165                 170                 175

Ala Gln Glu Phe Pro Arg Ala His Thr Thr Ser Ala Glu Glu Arg Val
            180                 185                 190

Thr Val Trp Cys Ser Asn Asp Tyr Leu Gly Met Gly Arg Asn Pro Glu
            195                 200                 205

Val Leu Ala Thr Met His Lys Thr Leu Asp Thr Tyr Gly Ala Gly Ala
        210                 215                 220

Gly Gly Thr Arg Asn Ile Ser Gly His Asn Gln His Ala Val Ser Leu
225                 230                 235                 240

Glu Asn Thr Leu Ala Lys Leu His Gly Lys Glu Ala Ala Leu Val Phe
                245                 250                 255

Ser Ser Cys Phe Val Ala Asn Asp Ala Thr Leu Ala Thr Leu Gly Ser
            260                 265                 270

Lys Leu Pro Asp Cys Val Ile Leu Ser Asp Ser Leu Asn His Ala Ser
        275                 280                 285

Met Ile Gln Gly Ile Arg His Ser Gly Ala Lys Lys Met Val Phe Lys
290                 295                 300

His Asn Asp Leu Val Asp Leu Glu Ala Lys Leu Ala Ala Leu Pro Leu
305                 310                 315                 320

His Val Pro Lys Ile Ile Ala Phe Glu Ser Val Tyr Ser Met Cys Gly
                325                 330                 335

Ser Ile Ala Pro Ile Glu Lys Ile Cys Asp Leu Ala Asp Lys Tyr Gly
            340                 345                 350

Ala Ile Thr Phe Leu Asp Glu Val His Ala Val Gly Met Tyr Gly Pro
        355                 360                 365

His Gly Ala Gly Val Ala Glu His Leu Asp Tyr Asp Ile Tyr Ala Ser
```

```
               370                 375                 380
Gln Asp Thr Val Asn Pro Arg Ser Thr Lys Gly Thr Val Met Asp Arg
385                 390                 395                 400

Ile Asp Ile Ile Thr Gly Thr Leu Gly Lys Ala Tyr Gly Cys Val Gly
                405                 410                 415

Gly Tyr Ile Ala Gly Ser Ala Ala Met Val Asp Thr Ile Arg Ser Leu
            420                 425                 430

Ala Pro Gly Phe Ile Phe Thr Thr Ser Leu Pro Pro Ala Thr Met Ala
        435                 440                 445

Gly Ala Asp Thr Ala Ile Gln Tyr Gln Ala Arg His Gln Gly Asp Arg
    450                 455                 460

Val Leu Gln Gln Leu His Thr Arg Ala Val Lys Ala Ala Phe Lys Glu
465                 470                 475                 480

Leu Asp Ile Pro Val Ile Pro Asn Pro Ser His Ile Ile Pro Leu Leu
                485                 490                 495

Val Gly Asp Ala Glu Val Ala Lys Lys Ala Ser Asp Lys Leu Leu Glu
            500                 505                 510

Glu His Gly Ile Tyr Val Gln Ala Ile Asn Tyr Pro Thr Val Pro Arg
        515                 520                 525

Gly Glu Glu Arg Leu Arg Ile Thr Pro Thr Pro Gly His Ile Lys Glu
    530                 535                 540

His Arg Asp His Leu Val Gln Ala Val Gln Thr Val Trp Asn Glu Leu
545                 550                 555                 560

Gly Ile Lys Arg Thr Ser Asp Trp Glu Ala Gln Gly Gly Phe Val Gly
                565                 570                 575

Val Gly Val Asp Gly Ala Glu Ala Glu Asn Gln Pro Ile Trp Asn Asp
            580                 585                 590

Val Gln Leu Gly Leu Lys Glu Asn Glu Ala Ile Glu Ala Ala Val Glu
        595                 600                 605

Arg Glu Phe Ala Glu Ala Pro Met Arg Thr Ala Thr Arg Pro Ala Ala
    610                 615                 620

Ala Ala Ala Ser Ser Ile Pro Val Gly Val Ala Ala
625                 630                 635

(2) INFORMATION FOR SEQ ID NO:3:

(i) SEQUENCE CHARACTERISTICS:
        (A) LENGTH: 1807 base pairs
        (B) TYPE: nucleic acid
        (C) STRANDEDNESS: single
        (D) TOPOLOGY: linear (xi) SEQUENCE DESCRIPTION: SEQ ID NO:3:

CTGGACCAAT GGTAACCCTC CGTAATTGCC TTACAGATTT AGCCCAGGGG GGTTATGGTA      60

TCCTTGGGTA TTGAGGCCTG GAAATTTTTT TAGCCACCAG TTTACAGCCA GTTTCCGTTT     120

GTAAATATTT CACATCCCCC GACCCTGTCC CAATACAATA ATTTTTTCGC TATATATAAC     180

GCCCCTAGCG TTGTTTTATG ATCCTTAAAT CCTTACTTGT ACCTGAAAAT TGCAACAAAT     240

GTACTGACCT GGATCGCTGG CCATTTATAT CATTGCCCTG CGAAGTCGTA TTCTGCCAGT     300

GGCACAGGCG CTATTCTCTT TTCTTCCCTC CACCGCGTTT CTATCTTCCA TAGCACCCCA     360

CTTGCTTGCC GCTCCTGTCA TTATGTCCTT TTCTAATCTC GTCTCTGACC TCGCCTTCAG     420

AGATTCTCAT GATGACCGAA GTTCTCAGAT ATCTCAGGTA CAATCGCAAG CCACTGCACG     480

ATCGTATACA AGCACAGCTG CCACAAGCGT CAGCATATCT GGCGACATCT CAAGCCAGCT     540
```

```
TCATTCCGGT TACAGCCATC CACTGAGCCG ATCATGGCAG GCTGAAAGAC AGTTGACTAA      600

AGTCCGCATT TTCTTTTGTA TTTACTGAGC TGCTCTAACC CCGAGATAGG AAATGCTTAT      660

TTATCCTCTC TTCATCACCG ATAATCCCGA TGAGGAGACT CCTATCCCGT CTCTCCCTGG      720

ACAGTATCGT CGAGGATTAA ACCGTCTAGT TCCTTTCATC AAACCACTTG CCCACAAGGG      780

GCTACGCTCA GTCATCCTGT TTGGCGTCCC ACTACACCCC TCTGCGAAGG ATGCACTAGG      840

TACCGCTGCA GACGATCCAT CTGGACCGGT AATTCAAGCT ATTCGCTTGC TTAGGTCGCG      900

GTTTCCTCAA CTTTATATCG TGACAGATGT GTGCCTTTGC GAGTATACTT CGCATGGCCA      960

CTGTGGGATA CTGCGAGAAG ATGGGACTCT TGATAATACA CAGTCTGTGG ATCGGATTTC     1020

GGATGTTGCT CTGGCTTATG CTGCCGCCGG AGCCCATTGT GTCGCTCCGT CTGATATGAA     1080

TGATGGGCGA GTGCGTGCTA TAAAACTGAA GCTTATTGAA GCCGGGATGG CCCACCGTGT     1140

CCTACTGATG TCCTACAGCG CCAAATTTAG CGGTTGTTTG TACGGCCCTT TCCGTGATGC     1200

AGCGGGGTCC TGCCCATCAT TCGGGGATCG CAGATGCTAC CAGTTACCAC CCGGAGGCCG     1260

TGGACTTGCT CGGCGCGCTA TACAGAGAGA TATAGGCGAA GGGGCAGACA TCATAATGGT     1320

AAAGCCGGCG AGCAGCTACC TGGACATTAT CAGAGACGCA AAAGAAATTG CCAAAGACAT     1380

TCCCATTGCT GCTTACCAGG TCAGCGGTGA GTATGCTATG ATACATGCTG GTGCCAAGGC     1440

GGGCGTATTT GACTTGAAAT CCATGGCCTT TGAAAGTACT GAAGGGATTA TAAGGGCTGG     1500

TGCTGGGATT ATAGTAAGCT ATTTCGTGCC TGATTTTCTA GATTGGCTTT CGAAATGATT     1560

TAGCTAGATG GAGCGTGATG AAAGCATCCA CCAGATAAAT AGCAGTGACG ATCGCGTTTG     1620

AATCATACCT ATTGGAGTAG AAGTCTCGGT ATCTCGTTGG GGATTCTCTA GGTTGCTTAT     1680

TTAACGTAAT GCCACGCCAT GTGTTATATA TTGCCTAAAT ACTTTTATAA AAGATACACC     1740

AAGCTGATGG TGCCAAGTGA CCACTTCTAA TAAATACAAT TATACCAATT CCTCCGAAAT     1800

ATGCGGG                                                               1807
```

(2) INFORMATION FOR SEQ ID NO:4:

(i) SEQUENCE CHARACTERISTICS:
        (A) LENGTH: 375 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Met Ser Phe Ser Asn Leu Val Ser Asp Leu Ala Phe Arg Asp Ser His
 1               5                  10                  15

Asp Asp Arg Ser Ser Gln Ile Ser Gln Val Gln Ser Gln Ala Thr Ala
            20                  25                  30

Arg Ser Tyr Thr Ser Thr Ala Ala Thr Ser Val Ser Ile Ser Gly Asp
        35                  40                  45

Ile Ser Ser Gln Leu His Ser Gly Tyr Ser His Pro Leu Ser Arg Ser
    50                  55                  60

Trp Gln Ala Glu Arg Gln Leu Thr Lys Glu Met Leu Ile Tyr Pro Leu
65                  70                  75                  80

Phe Ile Thr Asp Asn Pro Asp Glu Glu Thr Pro Ile Pro Ser Leu Pro
                85                  90                  95

Gly Gln Tyr Arg Arg Gly Leu Asn Arg Leu Val Pro Phe Ile Lys Pro
            100                 105                 110
```

Leu Ala His Lys Gly Leu Arg Ser Val Ile Leu Phe Gly Val Pro Leu
            115                 120                 125

His Pro Ser Ala Lys Asp Ala Leu Gly Thr Ala Ala Asp Asp Pro Ser
    130                 135                 140

Gly Pro Val Ile Gln Ala Ile Arg Leu Leu Arg Ser Arg Phe Pro Gln
145                 150                 155                 160

Leu Tyr Ile Val Thr Asp Val Cys Leu Cys Glu Tyr Thr Ser His Gly
                165                 170                 175

His Cys Gly Ile Leu Arg Glu Asp Gly Thr Leu Asp Asn Thr Gln Ser
            180                 185                 190

Val Asp Arg Ile Ser Asp Val Ala Leu Ala Tyr Ala Ala Ala Gly Ala
            195                 200                 205

His Cys Val Ala Pro Ser Asp Met Asn Asp Gly Arg Val Arg Ala Ile
            210                 215                 220

Lys Leu Lys Leu Ile Glu Ala Gly Met Ala His Arg Val Leu Leu Met
225                 230                 235                 240

Ser Tyr Ser Ala Lys Phe Ser Gly Cys Leu Tyr Gly Pro Phe Arg Asp
                245                 250                 255

Ala Ala Gly Ser Cys Pro Ser Phe Gly Asp Arg Arg Cys Tyr Gln Leu
            260                 265                 270

Pro Pro Gly Gly Arg Gly Leu Ala Arg Arg Ala Ile Gln Arg Asp Ile
            275                 280                 285

Gly Glu Gly Ala Asp Ile Ile Met Val Lys Pro Ala Ser Ser Tyr Leu
            290                 295                 300

Asp Ile Ile Arg Asp Ala Lys Glu Ile Ala Lys Asp Ile Pro Ile Ala
305                 310                 315                 320

Ala Tyr Gln Val Ser Gly Glu Tyr Ala Met Ile His Ala Gly Ala Lys
                325                 330                 335

Ala Gly Val Phe Asp Leu Lys Ser Met Ala Phe Glu Ser Thr Glu Gly
            340                 345                 350

Ile Ile Arg Ala Gly Ala Gly Ile Ile Val Ser Tyr Phe Val Pro Asp
            355                 360                 365

Phe Leu Asp Trp Leu Ser Lys
    370                 375

(2) INFORMATION FOR SEQ ID NO:5:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (xi) SEQUENCE DESCRIPTION: SEQ ID NO:5:

TTTATGATGG AGGCCCTTCT CCAGCAGTCT C                                    31

(2) INFORMATION FOR SEQ ID NO:6:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:6:

CTATGCATTT AAGCAGCAGC CGCGACTGG                                       29

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:7:

TCATTTAAAT GATGGAGTCT CTTCTCC                                          27

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:8:

TCTTAATTAA TCAGCTCACA TGCGGG                                           26

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:9:

GCGCGAATTC GTNGGNATNG GNATNAAYCA YGG                                   33

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:10:

GCGGATCCGG NGGRCARTTN GACAT                                            25

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:11:

GCGAATTCAC NCCNCARGTN TTYGAYAC                                         28

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:12:

GCGGATCCRA AYTCNCCNGG RAANGG                                           26

(2) INFORMATION FOR SEQ ID NO:13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:13:

GCGCGAATTC TGGCARTCNA C                                                     21

(2) INFORMATION FOR SEQ ID NO:14:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:14:

GCGCGAATTC TGGCARAGNA TG                                                    22

(2) INFORMATION FOR SEQ ID NO:15:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:15:

GGATCCGACA TYTTNGCCAT NGC                                                   23

(2) INFORMATION FOR SEQ ID NO:16:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:16:

GTYTCRATRT AGAAYTG                                                          17

(2) INFORMATION FOR SEQ ID NO:17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:17:

TCTCTTCCTT CCTGAATCCT C                                                     21

(2) INFORMATION FOR SEQ ID NO:18:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:18:

GTNGCNCCNW SNGAYATGAT GGA                                                   23

(2) INFORMATION FOR SEQ ID NO:19:

```
        (i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:19:

GCRTCNCKRA ANCCRTA                                                          17

(2) INFORMATION FOR SEQ ID NO:20:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:20:

GTGGCTCCGA GTGATAT                                                          17

(2) INFORMATION FOR SEQ ID NO:21:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:21:

GCATCGCGAA AAGGACCG                                                         18

(2) INFORMATION FOR SEQ ID NO:22:

(i) SEQUENCE CHARACTERISTICS:
            (A) LENGTH: 649 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:22:

Met Glu Ala Leu Leu Gln Gln Ser Arg Ala Met Cys Pro Phe Leu Lys
 1               5                  10                  15

Arg Ser Ser Pro Asn Thr Leu Arg Ser Leu Ala Thr Ala Thr Arg Pro
            20                  25                  30

Ser Thr Ser Pro Gly Gly Gly Thr Met Thr Asn Leu Gln Arg Ile Ala
        35                  40                  45

Arg Arg Cys Pro Val Met Ser Lys Ala Leu Ala Val Gln Ser Ala Arg
    50                  55                  60

Met Thr Gly Thr Lys Arg Phe Thr Ser Ala Ala Gly Val Pro Gly
65                  70                  75                  80

Ala Gly Ala Gly Thr Pro Lys Pro Thr Arg Gly Ser Pro Gly Lys Arg
                85                  90                  95

Ala Leu His Ser Thr Gly Gly Asn Gly Ala Asn Met Ser Thr Glu Phe
            100                 105                 110

His Lys Gly Ala Gln Gln Ile His Pro Gly Leu Ser Asn Ala Thr Arg
        115                 120                 125

Ser His Val Gly Ala Ser Ala Thr Val Ser Gly Pro Thr Pro Arg Ala
    130                 135                 140

Pro Val Ala Ala Pro Phe Asp Tyr Asp Ala Phe Tyr Asn Ala Glu Leu
145                 150                 155                 160
```

-continued

```
Gln Lys Lys His Gln Asp Lys Ser Tyr Arg Tyr Phe Asn Asn Ile Asn
                165                 170                 175
Arg Leu Ala Gln Glu Phe Pro Arg Ala His Thr Ala Ser Lys Asp Glu
            180                 185                 190
Lys Val Thr Val Trp Cys Ser Asn Asp Tyr Leu Gly Met Gly Arg Asn
        195                 200                 205
Pro Glu Val Leu Ala Thr Met His Lys Thr Leu Asp Thr Tyr Gly Ala
    210                 215                 220
Gly Ala Gly Gly Thr Arg Asn Ile Ser Gly His Asn Gln His Ala Val
225                 230                 235                 240
Ser Leu Glu Asn Thr Leu Ala Lys Leu His Gly Lys Glu Ala Ala Leu
                245                 250                 255
Val Phe Ser Ser Cys Phe Val Ala Asn Asp Ala Thr Leu Ala Thr Leu
            260                 265                 270
Gly Ser Lys Met Pro Asp Cys Val Ile Leu Ser Asp Ser Leu Asn His
        275                 280                 285
Ala Ser Met Ile Gln Gly Ile Arg His Ser Gly Arg Lys Lys Met Val
    290                 295                 300
Phe Lys His Asn Asp Leu Val Asp Leu Glu Thr Lys Leu Ala Ser Leu
305                 310                 315                 320
Pro Leu His Val Pro Lys Ile Ile Ala Phe Glu Ser Val Tyr Ser Met
                325                 330                 335
Cys Gly Ser Ile Ala Pro Ile Glu Ala Ile Cys Asp Leu Ala Asp Lys
            340                 345                 350
Tyr Gly Ala Ile Thr Phe Leu Asp Glu Val His Ala Val Gly Met Tyr
        355                 360                 365
Gly Pro His Gly Ala Gly Val Ala Glu His Leu Asp Tyr Glu Ile Tyr
    370                 375                 380
Ala Ser Gln Asp Thr Ala Asn Pro Leu Ser Thr Lys Gly Thr Val Met
385                 390                 395                 400
Asp Arg Ile Asn Ile Ile Thr Gly Thr Leu Gly Lys Ala Tyr Gly Cys
                405                 410                 415
Val Gly Gly Tyr Ile Ala Gly Ser Ala Ala Leu Val Asp Thr Ile Arg
            420                 425                 430
Ser Leu Ala Pro Gly Phe Ile Phe Thr Thr Ser Leu Pro Pro Ala Thr
        435                 440                 445
Met Ala Gly Ala Asp Thr Ala Ile Arg Tyr Gln Ala Arg His Gln Gln
    450                 455                 460
Asp Arg Ile Leu Gln Gln Leu His Thr Arg Ala Val Lys Gln Ser Phe
465                 470                 475                 480
Lys Asp Leu Asp Ile Pro Val Ile Pro Asn Pro Ser His Ile Val Pro
                485                 490                 495
Leu Leu Val Gly Asp Ala Glu Leu Ala Lys Gln Ala Ser Asp Lys Leu
            500                 505                 510
Leu Glu Glu His Gly Ile Tyr Val Gln Ala Ile Asn Tyr Pro Thr Val
        515                 520                 525
Pro Arg Gly Glu Glu Arg Leu Arg Ile Thr Pro Thr Pro Gly His Thr
    530                 535                 540
Gln Glu Leu Arg Asp His Leu Val Glu Ala Val Asn Thr Val Trp Asn
545                 550                 555                 560
Asp Leu Gly Ile Lys Arg Ala Ser Asp Trp Lys Ala Met Gly Gly Phe
                565                 570                 575
Val Gly Val Gly Val Glu Ala Ala Glu Leu Glu Asn Gln Pro Ile Trp
```

```
                    580                 585                 590
Thr Asp Ala Gln Leu Asn Met Arg Pro Asp Glu Thr Leu Glu Ala Ala
            595                 600                 605
Val Glu Arg Glu Phe Gln Ala Ala Val Pro Gly Met Lys Ala Gly Gly
    610                 615                 620
Ala Lys Ala Lys Pro Val Gly Ser Ile Ala Ala Asn Pro Ile Gly Ala
625                 630                 635                 640
Ser Ile Pro Val Ala Ala Ala Glx
                645

(2) INFORMATION FOR SEQ ID NO:23:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:23:

Met Gln Arg Ser Ile Phe Ala Arg Phe Gly Asn Ser Ser Ala Ala Val
1               5                   10                  15
Ser Thr Leu Asn Arg Leu Ser Thr Thr Ala Ala Pro His Ala Lys Asn
            20                  25                  30
Gly Tyr Ala Thr Ala Thr Gly Ala Gly Ala Ala Ala Thr Ala Thr
        35                  40                  45
Ala Ser Ser Thr His Ala Ala Ala Ala Ala Ala Ala Ala Asn His
    50                  55                  60
Ser Thr Gln Glu Ser Gly Phe Asp Tyr Glu Gly Leu Ile Asp Ser Glu
65                  70                  75                  80
Leu Gln Lys Lys Arg Leu Asp Lys Ser Tyr Arg Tyr Phe Asn Asn Ile
                85                  90                  95
Asn Arg Leu Ala Lys Glu Phe Pro Leu Ala His Arg Gln Arg Glu Ala
            100                 105                 110
Asp Lys Val Thr Val Trp Cys Ser Asn Asp Tyr Leu Ala Leu Ser Lys
        115                 120                 125
His Pro Glu Val Leu Asp Ala Met His Lys Thr Ile Asp Lys Tyr Gly
    130                 135                 140
Cys Gly Ala Gly Gly Thr Arg Asn Ile Ala Gly His Asn Ile Pro Thr
145                 150                 155                 160
Leu Asn Leu Glu Ala Glu Leu Ala Thr Leu His Lys Lys Glu Gly Ala
                165                 170                 175
Leu Val Phe Ser Ser Cys Tyr Val Ala Asn Asp Ala Val Leu Ser Leu
            180                 185                 190
Leu Gly Gln Lys Met Lys Asp Leu Val Ile Phe Ser Asp Glu Leu Asn
        195                 200                 205
His Ala Ser Met Ile Val Gly Ile Lys His Ala Asn Val Lys Lys His
    210                 215                 220
Ile Phe Lys His Asn Asp Leu Asn Glu Leu Glu Gln Leu Leu Gln Ser
225                 230                 235                 240
Tyr Pro Lys Ser Val Pro Lys Leu Ile Ala Phe Glu Ser Val Tyr Ser
                245                 250                 255
Met Ala Gly Ser Val Ala Asp Ile Glu Lys Ile Cys Asp Leu Ala Asp
            260                 265                 270
Lys Tyr Gly Ala Leu Thr Phe Leu Asp Glu Val His Ala Val Gly Leu
```

```
                275                 280                 285
Tyr Gly Pro His Gly Ala Gly Val Ala Glu His Cys Asp Phe Glu Ser
290                 295                 300

His Arg Ala Ser Gly Ile Ala Thr Pro Lys Thr Asn Asp Lys Gly Gly
305                 310                 315                 320

Ala Lys Thr Val Met Asp Arg Val Asp Met Ile Thr Gly Thr Leu Gly
                325                 330                 335

Lys Ser Phe Gly Ser Val Gly Gly Tyr Val Ala Ala Ser Arg Lys Leu
                340                 345                 350

Ile Asp Trp Phe Arg Ser Phe Ala Pro Gly Phe Ile Phe Thr Thr Thr
                355                 360                 365

Leu Pro Pro Ser Val Met Ala Gly Ala Thr Ala Ala Ile Arg Tyr Gln
370                 375                 380

Arg Cys His Ile Asp Leu Arg Thr Ser Gln Gln Lys His Thr Met Tyr
385                 390                 395                 400

Val Lys Lys Ala Phe His Glu Leu Gly Ile Pro Val Ile Pro Asn Pro
                405                 410                 415

Ser His Ile Val Pro Val Leu Ile Gly Asn Ala Asp Leu Ala Lys Gln
                420                 425                 430

Ala Ser Asp Ile Leu Ile Asn Lys His Gln Ile Tyr Val Gln Ala Ile
                435                 440                 445

Asn Phe Pro Thr Val Ala Arg Gly Thr Glu Arg Leu Arg Ile Thr Pro
450                 455                 460

Thr Pro Gly His Thr Asn Asp Leu Ser Asp Ile Leu Ile Asn Ala Val
465                 470                 475                 480

Asp Asp Val Phe Asn Glu Leu Gln Leu Pro Arg Val Arg Asp Trp Glu
                485                 490                 495

Ser Gln Gly Gly Leu Leu Gly Val Gly Glu Ser Gly Phe Val Glu Glu
                500                 505                 510

Ser Asn Leu Trp Thr Ser Ser Gln Leu Ser Leu Thr Asn Asp Asp Leu
                515                 520                 525

Asn Pro Asn Val Arg Asp Pro Ile Val Lys Gln Leu Glu Val Ser Ser
                530                 535                 540

Gly Ile Lys Gln
545

(2) INFORMATION FOR SEQ ID NO:24:

(i) SEQUENCE CHARACTERISTICS:
        (A) LENGTH: 587 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:24:

Met Val Thr Ala Ala Met Leu Leu Gln Cys Cys Pro Val Leu Ala Arg
1               5                   10                  15

Gly Pro Thr Ser Leu Leu Gly Lys Val Val Lys Thr His Gln Phe Leu
                20                  25                  30

Phe Gly Ile Gly Arg Cys Pro Ile Leu Ala Thr Gln Gly Pro Asn Cys
                35                  40                  45

Ser Gln Ile His Leu Lys Ala Thr Lys Ala Gly Gly Asp Ser Pro Ser
                50                  55                  60

Trp Ala Lys Gly His Cys Pro Phe Met Leu Ser Glu Leu Gln Asp Gly
```

```
                65                      70                      75                      80
Lys Ser Lys Ile Val Gln Lys Ala Ala Pro Glu Val Gln Glu Asp Val
                            85                      90                      95
Lys Ala Phe Lys Thr Asp Leu Pro Ser Ser Leu Val Ser Val Ser Leu
                100                     105                     110
Arg Lys Pro Phe Ser Gly Pro Gln Glu Gln Glu Gln Ile Ser Gly Lys
                115                     120                     125
Val Thr His Leu Ile Gln Asn Asn Met Pro Gly Asn Tyr Val Phe Ser
        130                     135                     140
Tyr Asp Gln Phe Phe Arg Asp Lys Ile Met Glu Lys Lys Gln Asp His
145                     150                     155                     160
Thr Tyr Arg Val Phe Lys Thr Val Asn Arg Trp Ala Asp Ala Tyr Pro
                    165                     170                     175
Phe Ala Gln His Phe Glu Ala Ser Val Ala Ser Lys Asp Val Ser
                180                     185                     190
Val Trp Cys Ser Asn Asp Tyr Leu Gly Met Ser Arg His Pro Gln Val
            195                     200                     205
Leu Gln Ala Thr Gln Glu Thr Leu Gln Arg His Gly Ala Gly Ala Gly
        210                     215                     220
Gly Thr Arg Asn Ile Ser Gly Thr Ser Lys Phe His Val Glu Leu Glu
225                     230                     235                     240
Gln Glu Leu Ala Glu Leu His Gln Lys Asp Ser Ala Leu Leu Phe Ser
                245                     250                     255
Ser Cys Phe Val Ala Asn Asp Ser Thr Leu Phe Thr Leu Ala Lys Ile
                260                     265                     270
Leu Pro Gly Cys Glu Ile Tyr Ser Asp Ala Gly Asn His Ala Ser Met
            275                     280                     285
Ile Gln Gly Ile Arg Asn Ser Gly Ala Ala Lys Phe Val Phe Arg His
        290                     295                     300
Asn Asp Pro Asp His Leu Lys Lys Leu Leu Glu Lys Ser Asn Pro Lys
305                     310                     315                     320
Ile Pro Lys Ile Val Ala Phe Glu Thr Val His Ser Met Asp Gly Ala
                    325                     330                     335
Ile Cys Pro Leu Glu Glu Leu Cys Asp Val Ser His Gln Tyr Gly Ala
                340                     345                     350
Leu Thr Phe Val Asp Glu Val His Ala Val Gly Leu Tyr Gly Ser Arg
            355                     360                     365
Gly Ala Gly Ile Gly Glu Arg Asp Gly Ile Met His Lys Ile Asp Ile
        370                     375                     380
Ile Ser Gly Thr Leu Gly Lys Ala Phe Gly Cys Val Gly Gly Tyr Ile
385                     390                     395                     400
Ala Ser Thr Arg Asp Leu Val Asp Met Val Arg Ser Tyr Ala Ala Gly
                    405                     410                     415
Phe Ile Phe Thr Thr Ser Leu Pro Pro Met Val Leu Ser Gly Ala Leu
                420                     425                     430
Glu Ser Val Arg Leu Leu Lys Gly Glu Glu Gly Gln Ala Leu Arg Arg
            435                     440                     445
Ala His Gln Arg Asn Val Lys His Met Arg Gln Leu Leu Met Asp Arg
        450                     455                     460
Gly Leu Pro Val Ile Pro Cys Pro Ser His Ile Ile Pro Ile Arg Val
465                     470                     475                     480
Gly Asn Ala Ala Leu Asn Ser Lys Leu Cys Asp Leu Leu Leu Ser Lys
                485                     490                     495
```

```
His Gly Ile Tyr Val Gln Ala Ile Asn Tyr Pro Thr Val Pro Arg Gly
            500                 505                 510

Glu Glu Leu Leu Arg Leu Ala Pro Ser Pro His His Ser Pro Gln Met
        515                 520                 525

Met Glu Asp Phe Val Glu Lys Leu Leu Leu Ala Trp Thr Ala Val Gly
    530                 535                 540

Leu Pro Leu Gln Asp Val Ser Val Ala Ala Cys Asn Phe Cys Arg Arg
545                 550                 555                 560

Pro Val His Phe Glu Leu Met Ser Glu Trp Glu Arg Ser Tyr Phe Gly
                565                 570                 575

Asn Met Gly Pro Gln Tyr Val Thr Thr Tyr Ala
            580                 585
```

(2) INFORMATION FOR SEQ ID NO:25:

(i) SEQUENCE CHARACTERISTICS:
        (A) LENGTH: 342 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:25:

```
Met His Thr Ala Glu Phe Leu Glu Thr Glu Pro Thr Glu Ile Ser Ser
1               5                   10                  15

Val Leu Ala Gly Gly Tyr Asn His Pro Leu Leu Arg Gln Trp Gln Ser
            20                  25                  30

Glu Arg Gln Leu Thr Lys Asn Met Leu Ile Phe Pro Leu Phe Ile Ser
        35                  40                  45

Asp Asn Pro Asp Asp Phe Thr Glu Ile Asp Ser Leu Pro Asn Ile Asn
    50                  55                  60

Arg Ile Gly Val Asn Arg Leu Lys Asp Tyr Leu Lys Pro Leu Val Ala
65                  70                  75                  80

Lys Gly Leu Arg Ser Val Ile Leu Phe Gly Val Pro Leu Ile Pro Gly
                85                  90                  95

Thr Lys Asp Pro Val Gly Thr Ala Ala Asp Asp Pro Ala Gly Pro Val
            100                 105                 110

Ile Gln Gly Ile Lys Phe Ile Arg Glu Tyr Phe Pro Glu Leu Tyr Ile
        115                 120                 125

Ile Cys Asp Val Cys Leu Cys Glu Tyr Thr Ser His Gly His Cys Gly
    130                 135                 140

Val Leu Tyr Asp Asp Gly Thr Ile Asn Arg Glu Arg Ser Val Ser Arg
145                 150                 155                 160

Leu Ala Ala Val Ala Val Asn Tyr Ala Lys Ala Gly Ala His Cys Val
                165                 170                 175

Ala Pro Ser Asp Met Ile Asp Gly Arg Ile Arg Asp Ile Lys Arg Gly
            180                 185                 190

Leu Ile Asn Ala Asn Leu Ala His Lys Thr Phe Val Leu Ser Tyr Ala
        195                 200                 205

Ala Lys Phe Ser Gly Asn Leu Tyr Gly Pro Phe Arg Asp Ala Ala Cys
    210                 215                 220

Ser Ala Pro Ser Asn Gly Asp Arg Lys Cys Tyr Gln Leu Pro Pro Ala
225                 230                 235                 240

Gly Arg Gly Leu Ala Arg Arg Ala Leu Glu Arg Asp Met Ser Glu Gly
                245                 250                 255
```

-continued

```
Ala Asp Gly Ile Ile Val Lys Pro Ser Thr Phe Tyr Leu Asp Ile Met
            260                 265                 270

Arg Asp Ala Ser Glu Ile Cys Lys Asp Leu Pro Ile Cys Ala Tyr His
            275                 280                 285

Val Ser Asp Glu Tyr Ala Met Leu His Ala Ala Glu Lys Gly Val
            290                 295                 300

Val Asp Leu Lys Thr Ile Ala Phe Glu Ser His Gln Gly Phe Leu Arg
305                 310                 315                 320

Ala Gly Ala Arg Leu Ile Ile Thr Tyr Leu Ala Pro Glu Phe Leu Asp
            325                 330                 335

Trp Leu Asp Glu Glu Asn
            340

(2) INFORMATION FOR SEQ ID NO:26:

(i) SEQUENCE CHARACTERISTICS:
        (A) LENGTH: 330 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:26:

Met Gln Pro Gln Ser Val Leu His Ser Gly Tyr Phe His Pro Leu Leu
1                   5                  10                  15

Arg Ala Trp Gln Thr Ala Thr Thr Thr Leu Asn Ala Ser Asn Leu Ile
            20                  25                  30

Tyr Pro Ile Phe Val Thr Asp Val Pro Asp Asp Ile Gln Pro Ile Thr
            35                  40                  45

Ser Leu Pro Gly Val Ala Arg Tyr Gly Val Lys Arg Leu Glu Glu Met
        50                  55                  60

Leu Arg Pro Leu Val Glu Gly Leu Arg Cys Val Leu Ile Phe Gly
65                  70                  75                  80

Val Pro Ser Arg Val Pro Lys Asp Glu Arg Gly Ser Ala Ala Asp Ser
            85                  90                  95

Glu Glu Ser Pro Ala Ile Glu Ala Ile His Leu Leu Arg Lys Thr Phe
            100                 105                 110

Pro Asn Leu Leu Val Ala Cys Asp Val Cys Leu Cys Pro Tyr Thr Ser
            115                 120                 125

His Gly His Cys Gly Leu Leu Ser Glu Asn Gly Ala Phe Arg Ala Glu
            130                 135                 140

Glu Ser Arg Gln Arg Leu Ala Glu Val Ala Leu Ala Tyr Ala Lys Ala
145                 150                 155                 160

Gly Cys Gln Val Val Ala Pro Ser Asp Met Met Asp Gly Arg Val Glu
            165                 170                 175

Ala Ile Lys Glu Ala Leu Met Ala His Gly Leu Gly Asn Arg Val Ser
            180                 185                 190

Val Met Ser Tyr Ser Ala Lys Phe Ala Ser Cys Phe Tyr Gly Pro Phe
            195                 200                 205

Arg Asp Ala Ala Lys Ser Ser Pro Ala Phe Gly Asp Arg Arg Cys Tyr
            210                 215                 220

Gln Leu Pro Pro Gly Ala Arg Gly Leu Ala Leu Arg Ala Val Asp Arg
225                 230                 235                 240

Asp Val Arg Glu Gly Ala Asp Met Leu Met Val Lys Pro Gly Met Pro
            245                 250                 255
```

```
Tyr Leu Asp Ile Val Arg Glu Val Lys Asp Lys His Pro Asp Leu Pro
            260                 265                 270

Leu Ala Val Tyr His Val Ser Gly Glu Phe Ala Met Leu Trp His Gly
            275                 280                 285

Ala Gln Ala Gly Ala Phe Asp Leu Lys Ala Ala Val Leu Glu Ala Met
            290                 295                 300

Thr Ala Phe Arg Arg Ala Gly Ala Asp Ile Ile Ile Thr Tyr Tyr Thr
305                 310                 315                 320

Pro Gln Leu Leu Gln Trp Leu Lys Glu Glu
                325                 330

(2) INFORMATION FOR SEQ ID NO:27:

(i) SEQUENCE CHARACTERISTICS:
        (A) LENGTH: 330 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:27:

Met His His Gln Ser Val Leu His Ser Gly Tyr Phe His Pro Leu Leu
1                   5                   10                  15

Arg Ala Trp Gln Thr Thr Pro Ser Thr Val Ser Ala Thr Asn Leu Ile
            20                  25                  30

Tyr Pro Ile Phe Val Thr Asp Val Pro Asp Val Gln Pro Ile Ala
            35                  40                  45

Ser Leu Pro Gly Val Ala Arg Tyr Gly Val Asn Gln Leu Glu Glu Met
50                  55                  60

Leu Arg Pro Leu Val Glu Ala Gly Leu Arg Cys Val Leu Ile Phe Gly
65                  70                  75                  80

Val Pro Ser Arg Val Pro Lys Asp Glu Gln Gly Ser Ala Ala Asp Ser
            85                  90                  95

Glu Asp Ser Pro Thr Ile Glu Ala Val Arg Leu Leu Arg Lys Thr Phe
            100                 105                 110

Pro Thr Leu Leu Val Ala Cys Asp Val Cys Leu Cys Pro Tyr Thr Ser
            115                 120                 125

His Gly His Cys Gly Leu Leu Ser Glu Asn Gly Ala Phe Leu Ala Glu
130                 135                 140

Glu Ser Arg Gln Arg Leu Ala Glu Val Ala Leu Ala Tyr Ala Lys Ala
145                 150                 155                 160

Gly Cys Gln Val Val Ala Pro Ser Asp Met Met Asp Gly Arg Val Glu
            165                 170                 175

Ala Ile Lys Ala Ala Leu Leu Lys His Gly Leu Gly Asn Arg Val Ser
            180                 185                 190

Val Met Ser Tyr Ser Ala Lys Phe Ala Ser Cys Phe Tyr Gly Pro Phe
            195                 200                 205

Arg Asp Ala Ala Gln Ser Ser Pro Ala Phe Gly Asp Arg Arg Cys Tyr
210                 215                 220

Gln Leu Pro Pro Gly Ala Arg Gly Leu Ala Leu Arg Ala Val Ala Arg
225                 230                 235                 240

Asp Ile Gln Glu Gly Ala Asp Ile Leu Met Val Lys Pro Gly Leu Pro
            245                 250                 255

Tyr Leu Asp Met Val Gln Glu Val Lys Asp Lys His Pro Glu Leu Pro
            260                 265                 270
```

-continued

```
Leu Ala Val Tyr Gln Val Ser Gly Glu Phe Ala Met Leu Trp His Gly
            275                 280                 285

Ala Lys Ala Gly Ala Phe Asp Leu Arg Thr Ala Val Leu Glu Ser Met
290                 295                 300

Thr Ala Phe Arg Arg Ala Gly Ala Asp Ile Ile Ile Thr Tyr Phe Ala
305                 310                 315                 320

Pro Gln Leu Leu Lys Trp Leu Lys Glu Glu
                325                 330
```

(2) INFORMATION FOR SEQ ID NO:28:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:28:

```
Thr Asp Leu Ile Gln Arg Pro Arg Arg Leu Arg Lys Ser Pro Ala Leu
1               5                   10                  15

Pro Arg Met Phe Glu Glu Thr Thr Leu Ser Leu Asn Asp Leu Val Leu
            20                  25                  30

Pro Ile Phe Val Glu Glu Glu Ile Asp Asp Tyr Lys Ala Val Glu Ala
            35                  40                  45

Met Pro Gly Val Met Arg Ile Pro Glu Lys His Leu Ala Arg Glu Ile
50                  55                  60

Glu Arg Ile Ala Asn Ala Gly Ile Arg Ser Val Met Thr Phe Gly Ile
65                  70                  75                  80

Ser His His Thr Asp Glu Thr Gly Glu Arg Ala Trp Arg Glu Asp Gly
            85                  90                  95

Leu Val Ala Arg Met Ser Arg Ile Cys Lys Gln Thr Val Pro Glu Met
            100                 105                 110

Ile Val Met Ser Asp Thr Cys Phe Cys Glu Tyr Thr Ser His Gly His
            115                 120                 125

Cys Gly Val Leu Cys Glu His Gly Val Asp Asn Asp Ala Thr Leu Glu
130                 135                 140

Asn Leu Gly Lys Gln Ala Val Val Ala Ala Ala Gly Ala Asp Phe
145                 150                 155                 160

Ile Ala Pro Ser Ala Ala Met Asp Gly Gln Val Gln Ala Ile Arg Gln
            165                 170                 175

Ala Leu Asp Ala Ala Gly Phe Lys Asp Thr Ala Ile Met Ser Tyr Ser
            180                 185                 190

Thr Lys Phe Ala Ser Ser Phe Tyr Gly Pro Phe Arg Glu Ala Ala Gly
            195                 200                 205

Ser Ala Leu Lys Gly Asp Arg Lys Ser Tyr Gln Met Asn Pro Met Asn
210                 215                 220

Arg Ala Glu Gly Ile Ala Glu Tyr Leu Leu Asp Glu Ala Gln Gly Ala
225                 230                 235                 240

Asp Cys Leu Met Val Lys Pro Ala Gly Ala Tyr Leu Asp Ile Val Arg
            245                 250                 255

Glu Leu Arg Glu Arg Thr Glu Leu Pro Ile Gly Ala Tyr Gln Val Ser
            260                 265                 270

Gly Glu Tyr Ala Met Ile Lys Phe Ala Ala Leu Ala Gly Ala Ile Asp
            275                 280                 285
```

```
Glu Glu Lys Val Val Leu Glu Ser Leu Gly Ser Ile Lys Arg Ala Gly
    290                 295                 300

Ala Asp Leu Ile Phe Ser Tyr Phe Ala Leu Asp Leu Ala Glu Lys Lys
305                 310                 315                 320

Ile Leu Arg (2) INFORMATION FOR SEQ ID NO:29:

(i) SEQUENCE CHARACTERISTICS:
        (A) LENGTH: 398 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:29:

His Thr Phe Val Asp Leu Lys Ser Pro Phe Thr Leu Ser Asn Tyr Leu
 1               5                  10                  15

Ser Phe Ser Ser Ser Lys Arg Arg Gln Pro Pro Ser Leu Phe Thr Val
                20                  25                  30

Arg Ala Ser Asp Ser Asp Phe Glu Ala Ala Val Val Ala Gly Lys Val
            35                  40                  45

Pro Glu Ala Pro Pro Val Pro Pro Thr Pro Ala Ser Pro Ala Gly Thr
50                  55                  60

Pro Val Val Pro Ser Leu Pro Ile Gln Arg Arg Pro Arg Arg Asn Arg
65                  70                  75                  80

Arg Ser Pro Ala Leu Arg Ser Ala Phe Gln Glu Thr Thr Leu Ser Pro
                85                  90                  95

Ala Asn Phe Val Tyr Pro Leu Phe Ile His Glu Gly Glu Glu Asp Thr
                100                 105                 110

Pro Ile Gly Ala Met Pro Gly Cys Tyr Arg Leu Gly Trp Arg His Gly
                115                 120                 125

Leu Leu Glu Glu Val Ala Lys Ala Arg Asp Val Gly Val Asn Ser Val
    130                 135                 140

Val Leu Phe Pro Lys Ile Pro Asp Ala Leu Lys Thr Pro Thr Gly Asp
145                 150                 155                 160

Glu Ala Tyr Asn Glu Asp Gly Leu Val Pro Arg Ser Ile Arg Leu Leu
                165                 170                 175

Lys Asp Lys Tyr Pro Asp Leu Ile Ile Tyr Thr Asp Val Ala Leu Asp
                180                 185                 190

Pro Tyr Ser Ser Asp Gly His Asp Gly Ile Val Arg Glu Asp Gly Val
                195                 200                 205

Ile Met Asn Asp Glu Thr Val His Gln Leu Cys Lys Gln Ala Val Ala
    210                 215                 220

Gln Ala Arg Ala Gly Ala Asp Val Val Ser Pro Ser Asp Met Met Asp
225                 230                 235                 240

Gly Arg Val Gly Ala Met Arg Val Ala Leu Asp Ala Glu Gly Phe Gln
                245                 250                 255

His Val Ser Ile Met Ser Tyr Thr Ala Lys Tyr Ala Ser Ser Phe Tyr
                260                 265                 270

Gly Pro Phe Arg Glu Ala Leu Asp Ser Asn Pro Arg Phe Gly Asp Lys
                275                 280                 285

Lys Thr Tyr Gln Met Asn Pro Ala Asn Tyr Arg Glu Ala Leu Thr Glu
    290                 295                 300
```

```
Met Arg Glu Asp Glu Ser Glu Gly Ala Asp Ile Leu Leu Val Lys Pro
305                 310                 315                 320

Gly Leu Pro Tyr Leu Asp Ile Ile Arg Leu Leu Arg Asp Asn Ser Pro
            325                 330                 335

Leu Pro Ile Ala Ala Tyr Gln Val Ser Gly Glu Tyr Ser Met Ile Lys
            340                 345                 350

Ala Gly Gly Ala Leu Lys Met Ile Asp Glu Glu Lys Val Met Met Glu
        355                 360                 365

Ser Leu Leu Cys Leu Arg Arg Ala Gly Ala Asp Ile Ile Leu Thr Tyr
    370                 375                 380

Phe Ala Leu Gln Ala Ala Arg Thr Leu Cys Gly Glu Lys Arg
385                 390                 395
```

(2) INFORMATION FOR SEQ ID NO:30:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:30:

```
Met Ser Gln Ser Phe Asn Arg His Arg Arg Leu Arg Thr Ser Lys Ala
1               5                   10                  15

Met Arg Glu Met Val Lys Glu Thr Arg Leu His Pro Ser Asp Phe Ile
            20                  25                  30

Tyr Pro Ile Phe Val Val Glu Gly Leu Glu Gly Lys Lys Ala Val Pro
            35                  40                  45

Ser Met Pro Asp Val His His Val Ser Leu Asp Leu Leu Lys Asp Glu
50                  55                  60

Val Ala Glu Leu Val Lys Leu Gly Ile Gln Ser Val Ile Val Phe Gly
65                  70                  75                  80

Ile Pro Glu Glu Lys Asp Asp Cys Gly Thr Gln Ala Tyr His Asp His
                85                  90                  95

Gly Ile Val Gln Lys Ala Ile Thr Glu Ile Lys Glu His Phe Pro Glu
            100                 105                 110

Met Val Val Val Ala Asp Thr Cys Leu Cys Glu Tyr Thr Asp His Gly
            115                 120                 125

His Cys Gly Leu Val Lys Asp Gly Val Ile Leu Asn Asp Glu Ser Leu
        130                 135                 140

Glu Leu Leu Ala Gln Thr Ala Val Ser Gln Ala Lys Ala Gly Ala Asp
145                 150                 155                 160

Ile Ile Ala Pro Ser Asn Met Met Asp Gly Phe Val Thr Val Ile Arg
                165                 170                 175

Glu Ala Leu Asp Lys Glu Gly Phe Val Asn Ile Pro Ile Met Ser Tyr
            180                 185                 190

Ala Val Lys Tyr Ser Ser Glu Phe Tyr Gly Pro Phe Arg Asp Ala Ala
            195                 200                 205

Asn Ser Thr Pro Gln Phe Gly Asp Arg Lys Thr Tyr Gln Met Asp Pro
210                 215                 220

Ala Asn Arg Met Glu Ala Leu Arg Glu Ala Gln Ser Asp Val Glu Glu
225                 230                 235                 240

Gly Ala Asp Phe Leu Ile Val Lys Pro Ser Leu Ser Tyr Met Asp Ile
                245                 250                 255
```

```
Met Arg Asp Val Lys Asn Glu Phe Thr Leu Pro Leu Val Ala Tyr Val
            260                 265                 270

Ser Gly Glu Tyr Ser Met Val Lys Ala Ala Ala Gln Asn Gly Trp Ile
            275                 280                 285

Lys Glu Lys Glu Ile Val Leu Glu Ile Leu Thr Ser Met Lys Arg Ala
            290                 295                 300

Gly Ala Asp Leu Ile Ile Thr Tyr His Ala Lys Asp Ala Ala Lys Trp
305                 310                 315                 320

Leu Ala Glu (2) INFORMATION FOR SEQ ID NO:31:

(i) SEQUENCE CHARACTERISTICS:
        (A) LENGTH: 424 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:31:

Met Met Ala Ser Thr Phe Asn Ile Pro Cys Asn Ala Gly Thr Ile Lys
1               5                   10                  15

Asn Phe Asn Asn Ser Gln Arg Asn Leu Gly Phe Ser Ser Asn Leu Gly
            20                  25                  30

Ile Asn Phe Ala Lys Thr Arg Phe Ser Asn Cys Gly Asp Ser Gly Arg
            35                  40                  45

Ile Pro Ser Gln Leu Val Val Arg Ala Ser Glu Arg Arg Asp Asn Leu
50                  55                  60

Thr Gln Gln Lys Thr Gly Leu Ser Ile Glu Glu Cys Glu Ala Ala Val
65                  70                  75                  80

Val Ala Gly Asn Ala Pro Ser Ala Pro Pro Val Pro Pro Thr Pro Lys
            85                  90                  95

Ala Pro Ser Gly Thr Pro Ser Val Ser Pro Leu Ser Leu Gly Arg Arg
            100                 105                 110

Pro Arg Arg Asn Arg Thr Ser Pro Val Phe Arg Ala Ala Phe Gln Glu
            115                 120                 125

Thr Thr Leu Ser Pro Ala Asn Val Val Tyr Pro Leu Phe Ile His Glu
            130                 135                 140

Gly Glu Glu Asp Thr Pro Ile Gly Ala Met Pro Gly Cys Tyr Arg Leu
145                 150                 155                 160

Gly Trp Arg His Gly Leu Val Glu Val Ala Lys Ala Arg Asp Val
            165                 170                 175

Val Val Asn Ser Ile Val Val Phe Pro Lys Pro Asp Ala Leu Lys Ser
            180                 185                 190

Pro Thr Gly Asp Glu Ala Tyr Asn Glu Asn Gly Leu Val Pro Arg Thr
            195                 200                 205

Ile Arg Met Leu Lys Asp Lys Phe Pro Asp Leu Ile Ile Tyr Thr Asp
            210                 215                 220

Val Ala Leu Asp Pro Tyr Tyr Asp Gly His Asp Gly Ile Val Thr
225                 230                 235                 240

Gln His Gly Val Ile Met Asn Asp Glu Thr Val His Gln Leu Cys Lys
            245                 250                 255

Gln Ala Val Ala Gln Ala Arg Ala Gly Ala Asp Val Val Ser Pro Ser
            260                 265                 270

Asp Met Met Asp Gly Arg Val Gly Ala Ile Arg Ala Ala Leu Asp Ala
```

```
                275                 280                 285
Glu Gly Tyr Ser Asn Val Ser Ile Met Ser Tyr Thr Ala Lys Tyr Ala
    290                 295                 300
Ser Ser Phe Tyr Pro Arg Phe Gly Asp Lys Lys Thr Tyr Gln Met Asn
305                 310                 315                 320
Pro Ala Asn Tyr Arg Glu Ala Leu Ile Glu Thr Gln Glu Asp Glu Ser
                325                 330                 335
Glu Gly Ala Asp Ile Leu Leu Val Lys Pro Gly Leu Pro Tyr Leu Asp
                340                 345                 350
Ile Ile Arg Leu Leu Arg Asp Asn Ser Asp Leu Pro Ile Ala Ala Tyr
                355                 360                 365
Gln Val Ser Gly Glu Tyr Ser Met Ile Lys Ala Gly Val Leu Lys
    370                 375                 380
Met Ile Asp Glu Glu Lys Val Met Leu Glu Ser Leu Leu Cys Leu Arg
385                 390                 395                 400
Arg Ala Gly Ala Asp Ile Ile Leu Thr Tyr Phe Ala Leu Gln Ala Ala
                405                 410                 415
Arg Cys Leu Cys Gly Glu Lys Arg
            420
```

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:32:

ATGCATCTGG AAACGCAACC CTGA                                            24

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:33:

ATGCATTCTA CGCCAGGACC GAGC                                            24

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:34:

TGGTGTACAG GGGCATAAAA T                                                    21

(2) INFORMATION FOR SEQ ID NO:35:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:35:

```
                                                  -continued
ATTTAAATCC AGTTGTGTAT ATAGAGGATT GTGG                                           34

(2) INFORMATION FOR SEQ ID NO:36:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (xi) SEQUENCE DESCRIPTION: SEQ ID NO:36:

ATTTAAATGA TGAGGAGCTC CCTTGTGCTG                                                30

(2) INFORMATION FOR SEQ ID NO:37:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (xi) SEQUENCE DESCRIPTION: SEQ ID NO:37:

TTAATTAACT AGAGTCGACC CAGCCGCGC                                                 29

(2) INFORMATION FOR SEQ ID NO:38:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (xi) SEQUENCE DESCRIPTION: SEQ ID NO:38:

GCATATTTAA ATGATGTCCT TTTCTAATCT CGT                                            33

(2) INFORMATION FOR SEQ ID NO:39:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:39:

ATATTAATTA ATCCATCTAG CTAAATCATT                                                30
```

1. A method for producing a secreted hemoprotein, comprising:
   (a) introducing into a filamentous fungal cell,
      (i) one or more first control sequences, wherein the one or more first control sequences, after introduction, are operably linked to one or more first nucleic acid sequences encoding one or more heme biosynthetic enzymes, wherein the first nucleic acid sequences are endogenous to the filamentous fungal cell; and/or
      (ii) one or more copies of one or more second nucleic acid sequences encoding one or more heme biosynthetic enzymes operably linked to one or more second control sequences which direct the expression of the second nucleic acid sequences;
   (b) cultivating the filamentous fungal cell in a nutrient medium suitable for production of the secreted hemoprotein and the heme biosynthetic enzymes; and
   (c) recovering the secreted hemoprotein from the nutrient medium of the filamentous fungal cell.

2. The method of claim 1, wherein one or more first control sequences are introduced into the filamentous fungal cell.

3. The method of claim 2, wherein the first control sequences are selected from the group consisting of a leader, polyadenylation sequence, promoter, propeptide coding region, signal peptide coding region, and transcription terminator.

4. The method of claim 2, wherein the one or more first control sequences are obtained from a filamentous fungal strain.

5. The method of claim 1, wherein one or more copies of one or more second nucleic acid sequences encoding one or more heme biosynthetic enzymes operably linked to one or more second control sequences which direct the expression of the second nucleic acid sequences are introduced into the filamentous fungal cell.

6. The method of claim 5, wherein the one or more second nucleic acid sequences are obtained from a filamentous fungal strain.

7. The method of claim 5, wherein the one or more second nucleic acid sequences encode a 5-aminolevulinic acid synthase.

8. The method of claim 7, wherein the one or more second nucleic acid sequences encode the 5-aminolevulinic acid synthase having an amino acid sequence set forth in SEQ ID NO:2.

9. The method of claim 8, wherein the one or more second acid sequences have a nucleic acid sequence set forth in SEQ ID NO: 1.

10. The method of claim 5, wherein the one or more second nucleic acid sequences encode a porphobilinogen synthase.

11. The method of claim 10, wherein the one or more second nucleic acid sequences encode the porphobilinogen synthase having an amino acid sequence set forth in SEQ ID NO:4.

12. The method of claim 11, wherein the porphobilinogen synthase has a nucleic acid sequence set forth in SEQ ID NO:3.

13. The method of claim 5, wherein the one or more second nucleic acid sequences encode a porphobilinogen deaminase.

14. The method of claim 5, wherein the one or more second nucleic acid sequences encode an uroporphyrinogen synthase.

15. The method of claim 5, wherein the one or more second nucleic acid sequences encode an uroporphyrinogen decarboxylase.

16. The method of claim 5, wherein the one or more second nucleic acid sequences encode a coproporphyrinogen III oxidase.

17. The method of claim 5, wherein the one or more second nucleic acid sequences encode a protoporphyrinogen IX oxidase.

18. The method of claim 5, wherein the one or more second nucleic acid sequences encode a ferrochelatase.

19. The method of claim 1, wherein one or more copies of the control sequences and one or more copies of the second nucleic acid sequence are introduced into the filamentous fungal cell.

20. The method of claim 1, further comprising introducing into the filamentous fungal cell before step a or step b one or more copies of a third nucleic acid sequence encoding the secreted hemoprotein.

21. The method of claim 1, further comprising introducing into the nutrient medium, a source of heme or heme analog.

22. The method of claim 1, further comprising introducing into the nutrient medium, a source of iron.

23. The method of claim 1, wherein the secreted hemoprotein is an oxidoreductase.

24. The method of claim 23, wherein the oxidoreductase is a catalase, oxidase, oxygenase, haloperoxidase, or peroxidase.

25. The method of claim 24, wherein the oxidoreductase is a catalase.

26. The method of claim 24, wherein the oxidoreductase is an oxidase.

27. The method of claim 24, wherein the oxidoreductase is an oxygenase.

28. The method of claim 24, wherein the oxidoreductase is a haloperoxidase.

29. The method of claim 24, wherein the oxidoreductase is a peroxidase.

30. The method of claim 29, wherein the peroxidase is obtained from a species of Coprinus, Arthromyces, or Phanerochaete.

31. The method of claim 30, wherein the peroxidase is obtained from a Coprinus strain.

32. The method of claim 31, wherein the peroxidase is obtained from a *Coprinus cinereus* strain.

33. The method of claim 31, wherein the peroxidase is obtained from a *Coprinus macrorhizus* strain.

34. The method of claim 1, wherein the secreted hemoprotein is native to the filamentous fungal cell.

35. The method of claim 1, wherein the secreted hemoprotein is foreign to the filamentous fungal cell.

36. The method of claim 1, wherein the filamentous fungal cell is a cell of a species of Acremonium, Aspergillus, Fusarium, Humicola, Myceliophthora, Mucor, Neurospora, Penicillium, Thielavia, Tolypocladium, or Trichoderma.

37. The method of claim 36, wherein the filamentous fungal cell is an Aspergillus cell.

38. The method of claim 37, wherein the Aspergillus cell is an *Aspergillus oryzae* cell.

39. The method of claim 37, wherein the Aspergillus cell is an *Aspergillus niger* cell.

* * * * *